US008557241B2

(12) United States Patent
Sigal et al.

(10) Patent No.: US 8,557,241 B2
(45) Date of Patent: Oct. 15, 2013

(54) SECRETED/CELL BOUND POXVIRUS PROTEINS AND METHODS OF USE THEREOF AS VACCINES AND ANTI-VIRAL AGENTS

(75) Inventors: Luis J. Sigal, Glenside, PA (US); Ren-Huan Xu, Jenkintown, PA (US)

(73) Assignee: The Institute for Cancer Research, Philadelphia, PA (US)

( * ) Notice: Subject to any disclaimer, the term of this patent is extended or adjusted under 35 U.S.C. 154(b) by 123 days.

(21) Appl. No.: 12/787,792

(22) Filed: May 26, 2010

(65) Prior Publication Data

US 2010/0254981 A1    Oct. 7, 2010

Related U.S. Application Data

(63) Continuation-in-part of application No. PCT/US2008/084929, filed on Nov. 26, 2008.

(60) Provisional application No. 60/990,151, filed on Nov. 26, 2007.

(51) Int. Cl.
*A61K 39/42* (2006.01)
*C07K 16/08* (2006.01)

(52) U.S. Cl.
USPC .......... 424/133.1; 424/147.1; 530/387.3; 530/388.3; 530/389.4

(58) Field of Classification Search
None
See application file for complete search history.

(56) References Cited

U.S. PATENT DOCUMENTS

| | | | |
|---|---|---|---|
| 6,982,156 B2 * | 1/2006 | Rosengard | 424/159.1 |
| 2002/0071849 A1 | 6/2002 | Smith et al. | |
| 2006/0029612 A1 | 2/2006 | Palmer et al. | |
| 2006/0099224 A1 | 5/2006 | Kirn | |
| 2006/0159699 A1 | 7/2006 | Howley et al. | |
| 2007/0207526 A1 | 9/2007 | Coit et al. | |
| 2011/0027282 A1 * | 2/2011 | Kotenko et al. | 424/139.1 |

OTHER PUBLICATIONS

Alcami, Nature Reviews Immunology 3:36-50, 2003.*
Alcami et al (Journal of Virology 74:1230-11239, 2000).*
Esposito, et al. GenBank Direction Submission, Accession No. ABF23761. Aug. 19, 2006.
Esposito, et al. GenBank Direction Submission, Accession No. ABF23769. Aug. 19, 2006.
Likos, et al. GenBank Direction Submission, Accession No. AAY97783. Sep. 28, 2005.
Likos, et al. GenBank Direction Submission, Accession No. AAY97599. Sep. 28, 2005.

* cited by examiner

*Primary Examiner* — Mary E Mosher
(74) *Attorney, Agent, or Firm* — Dann, Dorfman, Herrell & Skillman; Kathleen D. Rigaut

(57) ABSTRACT

Compositions and methods for the treatment and prevention of pox virus infections are disclosed.

3 Claims, 20 Drawing Sheets

Figure 1C

Antigen: Rec eIFN-α bp

Anti-sera
- Rev166
- VACV
- Δ166
- Naïve

Figure 5E anti-Rev166 (μl/well)  anti-Δ166 (μl/well)

Figure 5F

|   | 1 | 2 | 3 | 4 | 5 |
|---|---|---|---|---|---|
| VSV | Yes | No | Yes | Yes | Yes |
| Human IFNα | No | Yes | Yes | Yes | Yes |
| T1-IFNbp-VARV | No | No | No | Yes | Yes |
| MB-mAb | No | No | No | No | Yes |

Figure 8D

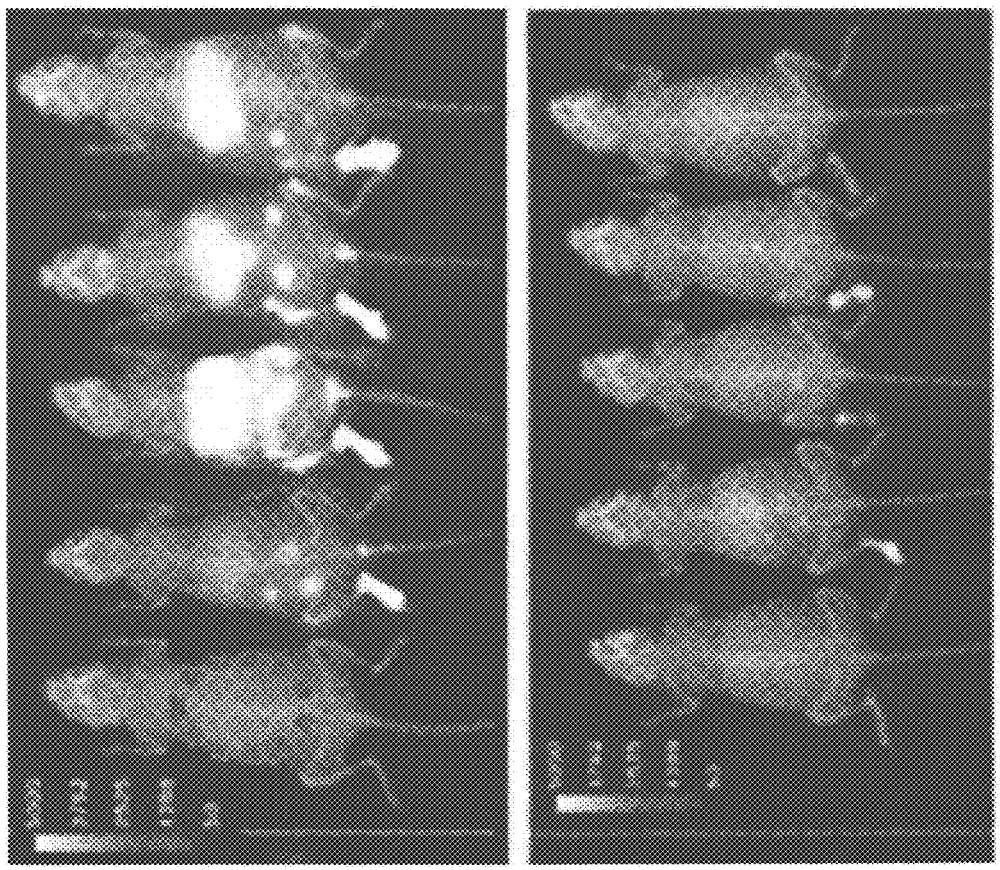

SECRETED/CELL BOUND POXVIRUS PROTEINS AND METHODS OF USE THEREOF AS VACCINES AND ANTI-VIRAL AGENTS

This application is a continuation-in-part of PCT/US08/84929 filed Nov. 26, 2008 which in turn claims priority under 35 U.S.C. §119(e) to U.S. Provisional Application 60/990,151 filed Nov. 26, 2007, the entire disclosure of each being incorporated by reference herein.

Pursuant to 35 U.S.C. §202(c) it is acknowledged that the U.S. Government has rights in the invention described, which was made in part with funds from the National Institutes of Health, Grant Number RO1A1065544.

FIELD OF THE INVENTION

This invention relates to the fields of drug discovery and vaccine production. More specifically, the invention provides materials and methods for developing effective anti-viral agents.

BACKGROUND OF THE INVENTION

Several publications and patent documents are cited throughout the specification in order to describe the state of the art to which this invention pertains. Each of these citations is incorporated by reference herein as though set forth in full.

The poxviridae comprise a large family of complex DNA viruses that replicate in the cytoplasm of vertebrate and invertebrate cells. In humans, smallpox was by far the most important poxvirus infection. The causative agent of smallpox is the variola virus, a member of the genus Orthopoxvirus. Vaccinia virus, also a member of the genus Orthopoxvirus in the family of Poxviridae, was used as live vaccine to immunize against smallpox. Successful worldwide vaccination with Vaccinia virus culminated in the eradication of variola virus (The global eradication of smallpox. Final report of the global commission for the certification of smallpox eradication; History of Public Health, No. 4, Geneva: World Health Organization, 1980). However, smallpox or smallpoxlike diseases still pose a major potential health problem. Additionally, certain pox virus infections cause great damage to livestock and wild life populations and are often require costly eradication procedures.

By inducing an anti-viral state in cells (1) and modulating the immune response (2), IFNs are major mediators of the anti-viral defense (3). Thus, the interferon (IFN) pathway is one of the most frequent targets of immune response modifiers (IRMs) encoded by viruses (1, 4) including OPVs (5). Type I IFN-α and -β signal through a common receptor (IFN-α/βR) which is expressed at the surface of the majority of cells (6). Most OPVs encode a high affinity type I IFN binding protein (bp) supposed to inhibit type I IFN signaling by sequestering Type I IFNs away from the IFN-α/βR (7-11). In the case of ECTV, the Type I IFN by is encoded in gene EVM166 and binds with high affinity to mouse IFN-α but, surprisingly, not-β (7) (herein eIFN-α bp). While it is presumed that IRMs are important for OPV virulence, only a few studies have been performed in vivo with OPVs in their natural hosts. Studying the role of IRMs in natural hosts is essential to understand virus virulence, define new targets of anti-viral therapies, and test the possibility of using secreted IRMs as targets of subunit anti-viral vaccines.

SUMMARY OF THE INVENTION

In accordance with the present invention, an anti-pox vaccine is provided. An exemplary vaccine comprises a SPVP in a biologically compatible medium, which upon administration to a patient, induces an immune response which is effective in attenuating pox virus infection. The vaccine may optionally comprise a pharmaceutical adjuvant.

Suitable SPVP for use as immunogens include, without limitation, viral interferon binding proteins, viral c-type lectins, viral chemokines, viral complement binding proteins, viral interleukin-1 receptor binding proteins, viral interleukin-18 binding proteins, viral interferon gamma receptor binding proteins, viral interferon α/β receptor binding proteins, viral semaphorins and viral TNF receptor binding proteins. The sequences encoding the SPVPs of the invention and their cognate pox viruses are provided in Tables I-XI. In a particularly preferred embodiment, the SPVP is an interferon a binding protein and is listed in table IX.

Also encompassed by the present invention are methods for inhibiting infection with a pox virus that expresses a SPVP. An exemplary method entails administering an SPVP containing vaccine as described above which is effective to attenuate pox infection in the subject.

In an alternative embodiment, methods for prevention and/or treatment of a pox virus infection comprising passive infusion of neutralizing anti-pox virus antibodies or functional fragments thereof are also disclosed. Such functional fragments can include a single chain Fv antibody molecule, a diabody, a tribody, a tetrabody, a recombinantly produced IgG, Fab, Fab', F(ab')$_2$, F(v), scFv, scFv$_2$, scFv-Fc, minibody, a bispecific antibody, an Affibody®, and a peptabody. In a preferred embodiment of this aspect of the invention, the antibodies block the action of a virally encoded immune response modifier protein. In a particularly preferred embodiment the antibody blocks the action of an interferon binding protein.

BRIEF DESCRIPTION OF THE DRAWINGS

FIG. 1. Generation of Δ166 and Rev166. FIG. 1b) As in a) but the process was reversed and non-fluorescent plaques were selected to obtain Rev166. FIG. 1c) Micrograph of WT and Δ166 plaques showing the fluorescence of Δ166.

FIG. 2. eIFN-α bp is essential for ECTV virulence.

FIG. 4. eIFN-α bp affects adaptive and innate immunity.

FIG. 5. eIFN-α bp is a natural target of the antibody response. FIG. 5e) Mice were inoculated i.v. with 50 µg Rec eIFN-α bp immediately and 3 days PI with ECTV Δ166. A group of control infected mice received PBS instead of Rec eIFN-α bp while a second control group received Rec eIFN-α bp but remained uninfected. Survival was monitored. FIG. 5f) MEFs were treated for 24 hours with 20 IU IFN-α in the presence or the absence of the indicated amounts of Rec eIFN-α bp and/or sera from ECTV Δ166 or Rev166 immune mice. MEFs were next infected with VSV, incubated for 24 hours and then fixed and stained with crystal violet.

FIG. 6a) Balb/c mice were immunized and boosted twice with Rec eIFN-α bp or control recombinant human HER2/neu produced in E. coli. As additional controls, Balb/c mice were infected with Δ166 and B6 mice with Rev166. Three weeks after the last boost or infection, sera was collected and anti-eIFN-Δ by was determined by ELISA. FIG. 6b) The immunized mice in a were challenged with 300 PFU WT ECTV and survival was monitored. Data corresponds to 5 mice/group and is representative of 3 identical experiments.

DETAILED DESCRIPTION OF THE INVENTION

Figure 1A:
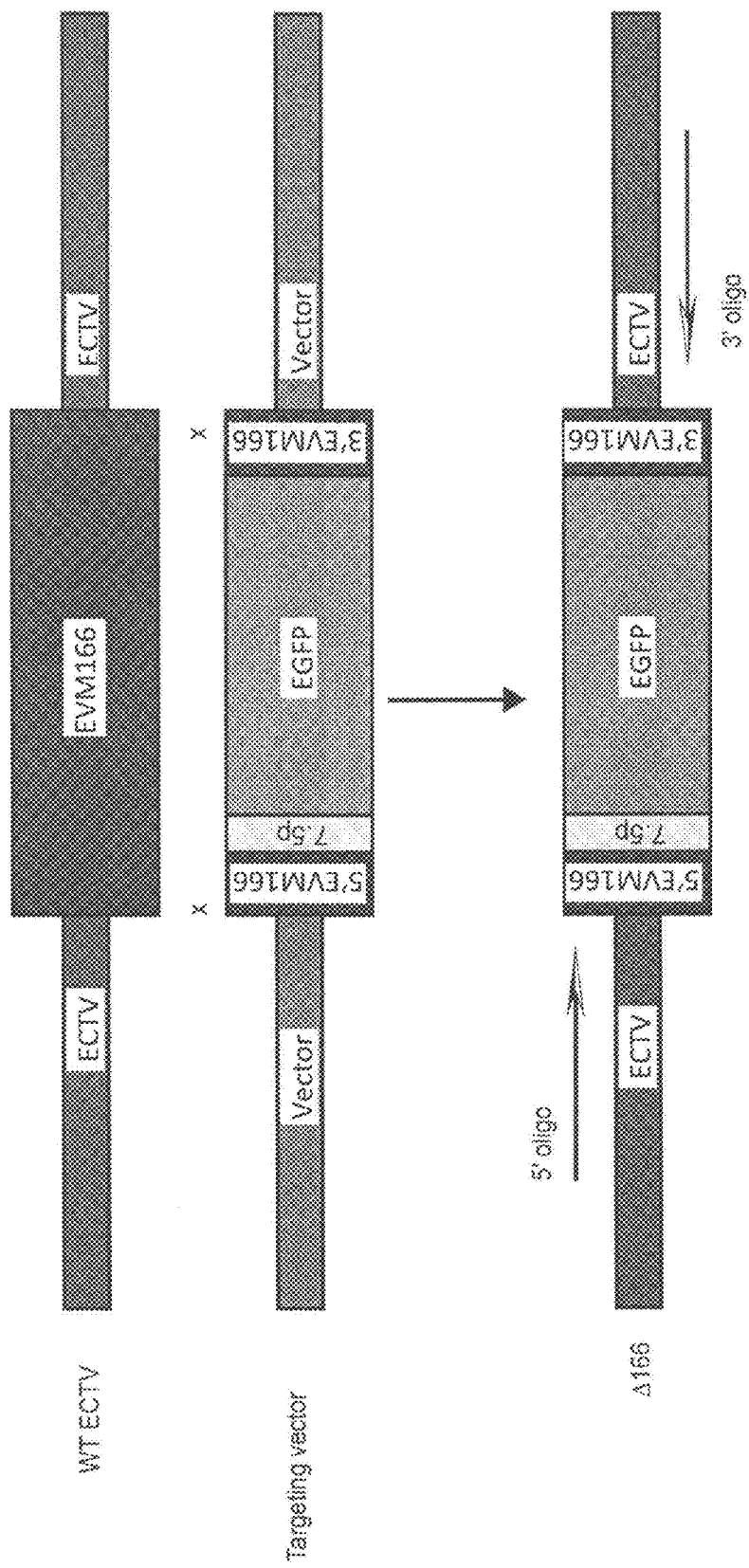
FIG. 1a, FIG. 1b) Schematic representation of the strategies to generate Δ166 and Rev166 (not to scale) FIG. 1a) A construct consisting of EGFP (green) controlled by the early/late4 7.5 OPV promoter (yellow) and flanked by the 5' and 3' 300 by of EVM166 (dark blue) was introduced into plasmid Bluescript II KS+ (orange). This targeting vector was used to generate Δ166 by homologous recombination with WT ECTV as indicated. Recombinant plaques were selected by green fluorescence. The correct insertion of EGFP was determined by sequencing using oligos (arrows) corresponding to ECTV sequences flanking EVM166 (light blue).

Non-living anti-viral vaccines traditionally target proteins expressed at the surface of the virion with the hope of preventing infection through neutralizing antibodies. Orthopoxviruses (OPVs) including variola virus (VARV, agent of smallpox) and the murine equivalent ectromelia virus (ECTV, agent of mousepox) encode immune response modifiers (IRMs) thought to increase virulence by decreasing the host immune response. Here we show that one of these IRMs, the interferon alpha binding protein of ECTV (eIFN-α bp), is absolutely essential for ECTV virulence and is a natural target of the antibody response. Strikingly, we demonstrate that immunization with recombinant eIFN-α bp protects mice from lethal mousepox. Together, this work has important implications for our understanding of the role of type I IFNs in OPV infections, the role of IRMs in OPV virulence, and the mechanisms whereby the smallpox vaccine protects. Furthermore, these experiments provide a rationale for the use of virulence factors as targets of antiviral vaccines.

While attenuation of mouse pox infection is described herein, this approach may be extrapolated to immunize humans and animals against other pox virus infections. As mentioned above, each pox virus expresses SPVP which could be employed as a target to induce viral immunity or resistance. Tables I-XI provide a listing of ortholog genes from many poxviruses that are secreted virulence factors and thus may be employed in the methods described herein. The function of the factor is indicated in the title and names of the virus and gene number are also provided. For example, other such SPVP include without limitation, CC-lectin like, CD47-like, complement-binding, Il-1β receptor, Il-18 binding protein, interferon gamma receptor, interferon beta receptor, semaphorin, and TNF receptor. See Tables I-XI.

Definitions

The term "SPVP" as used herein refers to a non-structural, secreted viral proteins that may or may not bind to the surface of cells during active infection. SPVP are frequently immune response modifiers and often contribute to viral virulence.

As defined herein, the term "attenuated" means a virus which is immunologically related to the wild type pox virus (i.e., the virulent virus) but which is not itself pathogenic and does not produce a "classical pox disease," and is not a wild type virus. An attenuated measles virus is replication-competent, in that it is capable of infecting and replicating in a host cell without additional viral functions supplied by, for example, a helper virus or a plasmid expression construct encoding such additional functions. When referring to viral infection in a subject, "attenuate" means inhibition of infection or decreasing viral load in the subject.

As used herein, the terms "wild-type" or "wild-type virus" refer to the characteristics of a pox virus as it is found in nature which is pathogenic.

As used herein, the term "patient" or "subject" refers to an organism to which viruses of the invention can be administered. Preferably, a patient is a bird or a mammal, e.g., a human, primate, livestock animal, or a rodent.

As used herein, the term "biological fluid" refers to any extracellular bodily fluid, including but not limited to blood, urine, saliva, interstitial fluid, lymph, and cerebrospinal fluid.

An "immune response" signifies any reaction produced by an antigen, such as a viral antigen, in a host having a functioning immune system. Immune responses may be either humoral in nature, that is, involve production of immunoglobulins or antibodies, or cellular in nature, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems. Such immune responses may be important in protecting the host from disease and may be used prophylactically and therapeutically.

An "antibody" or "antibody molecule" is any immunoglobulin, including antibodies and fragments thereof, that binds to a specific antigen. The term includes polyclonal, monoclonal, chimeric, single domain (Dab) and bispecific antibodies. As used herein, antibody or antibody molecule contemplates recombinantly generated intact immunoglobulin molecules and immunologically active portions of an immunoglobulin molecule such as, without limitation: Fab, Fab', F(ab')$_2$, F(v), scFv, scFv$_2$, scFv-Fc, minibody, diabody, tetrabody, single variable domain (e.g., variable heavy domain, variable light domain), bispecific, Affibody® molecules (Affibody, Bromma, Sweden), and peptabodies (Terskikh et al. (1997) PNAS 94:1663-1668). Dabs can be composed of a single variable light or heavy chain domain. In a certain embodiment of the invention, the variable light domain and/or variable heavy domain specific for an immune response modifier protein are inserted into the backbone of the above mentioned antibody constructs. Methods for recombinantly producing antibodies are well-known in the art. For example, commercial vectors comprising constant genes to make IgGs from scFvs are provided by Lonza Biologics (Slough, United Kingdom).

"Fv" is an antibody fragment which contains an antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although often at a lower affinity than the entire binding site.

"Single-chain Fv" or "scFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the scFv to form the desired structure for antigen binding. For a review of scFv see, for example, Pluckthun, A. in The Pharmacology of Monoclonal Antibodies, vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) on the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Holliger et al., (1993) Proc. Natl. Acad. Sci. USA, 90: 6444-6448.

With respect to antibodies, the term "immunologically specific" refers to antibodies that bind to one or more epitopes of a protein or compound of interest, but which do not substantially recognize and bind other molecules in a sample containing a mixed population of antigenic biological molecules.

As used herein, the term "administering systemically" refers to exposure of the cells of an organism to an attenuated pox virus via the circulatory system of the patient, such as by intravenous injection or the use of a medical access device, such as a catheter.

As used herein, the term "recombinant virus" or "modified virus" refers to a virus or viral polypeptide which is altered by genetic engineering, by modification or manipulation of the genetic material encoding that polypeptide, or found in the virus such that it is not identical to the naturally occurring virus or polypeptide.

According to the methods of the subject invention, the anti-pox vaccine compositions described herein are administered to susceptible hosts, in an effective amount and manner to induce protective immunity against subsequent challenge or infection of the host by the cognate pox virus. The vaccines, comprising SPVP or attenuated virus, are typically administered parenterally, by injection, for example, either subcutaneously, intraperitoneally, or intramuscularly. Other suitable modes of administration include oral or nasal administration. Usually, the vaccines are administered to a host at least two times, with an interval of one or more weeks between each administration. However, other regimens for the initial and booster administrations of the vaccine are contemplated, and may depend on the judgment of the practitioner and the particular host animal being treated.

In an alternative embodiment, the anti-pox vaccine is administered to the patient in a biologically compatible solution or a pharmaceutically acceptable delivery vehicle, by administration either directly into cells or systemically (e.g., intravenously). Suitable pharmaceutical formulations, in part, depend upon the use or the route of entry, for example transdermal, or by injection. Such forms should not prevent the composition or formulation from reaching a target cell (i.e., a cell to which the virus is desired to be delivered to) or exerting its effect. For example, pharmacological compositions injected into the blood stream should be soluble. The anti-pox vaccines described herein may optionally also contain a viral structural protein preparation to facilitate the mounting of a robust immune response. Suitable proteins for this purpose, include, without limitation, A33R, B5R and L1R from vaccinia and orthologs thereof present in other poxviruses.

While dosages administered will vary from patient to patient (e.g., depending upon the size of the patient), a "therapeutically effective dose" will be determined by setting as a lower limit, the concentration of virus proven to be safe as a vaccine (e.g., $10^3$ pfu) and escalating to higher doses of up to $10^{12}$ pfu, while monitoring for a reduction in viral load along with the presence of any deleterious side effects. Escalating dose studies are routine in the art (see, e.g., Nies and Spielberg, "Principles of Therapeutics," In Goodman & Gilman's The Pharmacological Basis of Therapeutics, eds. Hardman, et al., McGraw-Hill, NY, 1996, pp 43 62).

In a preferred embodiment, SPVP will be infused into the patient in a biologically compatible medium. Thus, the SPVP is delivered systemically via injection in an amount effective to generate an antibody response to the molecule. Alternatively, an intravenous delivery device designed for administration of multiple doses of a medicament may be employed for this purpose. Such devices include, but are not limited to, winged infusion needles, peripheral intravenous catheters, midline catheters, peripherally inserted central catheters (PICC), and surgically placed catheters or ports (see, e.g., U.S. Pat. No. 6,012,034).

In preferred embodiments of the invention, a composition comprising an attenuated pox virus is delivered in a therapeutically effective dose in the range of from about $10^3$ pfu to about $10^{12}$ pfu. In one embodiment of the invention, the dose range is $10^5$ to $10^7$ pfu. In some embodiments, the therapeutically effective dose is provided in repeated doses. Repeat doses (using the same, or further modified virus) can be administered by the same route as initially used or by another route. A therapeutically effective dose can be delivered in several discrete doses (e.g., days or weeks apart) and in one embodiment of the invention, one to about twelve doses are provided. Alternatively, a therapeutically effective dose of attenuated pox virus is delivered by a sustained release formulation.

The vaccine compositions of the subject invention can be prepared by procedures well known in the art. For example, the vaccines are typically prepared as injectables, e.g., liquid solutions or suspensions for subcutaneous administration. The vaccines are administered in a manner that is compatible with dosage formulation, and in such amount as will be therapeutically effective and immunogenic in the recipient. The optimal dosages and administration patterns for a particular vaccine formulation can be readily determined by a person skilled in the art.

SPVP or attenuated viruses are typically combined with an adjuvant just prior to administration. Adjuvants used in the vaccine formulations typically were either threonyl muramyl dipeptide (MDP) (Byars et al., 1987) or a combination of Freund's complete and incomplete adjuvants. A variety of other adjuvants suitable for use with the methods and vaccines of the subject invention, such as alum, are well known in the art and are contemplated for use with the subject invention.

Finally, as demonstrated herein, neutralizing anti-SPVP antibodies can be generated for passive infusion into a patient. In this embodiment, antibodies which neutralize the pox virus are produced in large quantities and an effective amount of the same infused into the subject to be treated to prevent or treat pox virus infections. Methods for passive infusion of antibodies into human patients are well known to the skilled clinician. The passive transfer of antibodies in the form of whole plasma or fractionated preparations, such as gammaglobulins, has been used for both the prophylaxis and treatment of infection in patients with primary immunodeficiency, as well as infections associated with transplantation, chronic leukemia, premature birth, and surgery (See Berkman, S A, et al., Ann. Intern. Med. 112:278, 1990; Ziegler, E J, et al., New England J. of Med. 307;1225, 1982; Gordon, D S, Am. J. Med. 83:1m 1987, [suppl. 4A]; Winston, D J, et al., Ann. Intern. Med. 106:12, 1987; The National Institute of Child Health and Human Development Intravenous Immunoglobulin Study Group, New England J. of Med. 325:73, 1991). Hyperimmune antibodies directed against a single organism passively transferred to recipients has been particularly useful in the treatment of cytomegalovirus, hepatitis B, tetanus, vaccinia, and herpes (Orenstein, W A, et al., J. Pedicat. 98:368, 1981; Snydman, D R, et al., New England J. of Med. 317:1049, 1987; Beasley, et al., Lancet 2:388, 1981). Accordingly, such treatment methods are encompassed by the present invention.

The following examples are provided to illustrate certain embodiments of the invention. They are not intended to limit the invention in any way.

EXAMPLE I

Most existing anti-viral recombinant vaccines are directed to target proteins that form part of the structure of the virus. Poxviruses encode proteins that are not part of the virus structure and are secreted into the extracellular milieu and sometimes bind to the surface of cells. Most of these proteins, referred to herein as SPVP, are immune response modifiers and involved in virus virulence. Accordingly, we hypothesized that if a SPVP were essential for virulence, anti-pox vaccines could be designed to induce antibodies to these essential proteins. The antibodies so produced should neutralize the function of the SPVP and prevent pox virus disease. To test this hypothesis we generated ectromelia virus (a poxvirus) deficient in the open reading frame of EVM166 (Δ166) that encodes for the SPVP interferon-alpha binding protein (IFN-α bp). Surprisingly, this deletion extremely attenuated the ability of the recombinant virus to infect mice. These data indicate that IFN-α binding protein is essential for poxvirus pathogenesis. We then produced recombinant IFN-α binding protein in E. coli and used this to immunize mice. We found that when immunized mice were infected with pathogenic ectromelia virus, they were protected from lethal disease. Thus, SPVP can serve as effective targets for anti-pox virus vaccines.

The following materials and methods are provided to facilitate the practice of the invention.

Mice: Balb/c mice were purchased from the National Cancer Institute (Frederick). RAG1-KO mice in a C57BL/6 background were originally purchased from Jackson laboratories and bred at FCCC. C57BL/6 mice were obtained from the FCCC colony. All mice were used in experiments when they were 5-8 weeks old. All protocols involving mice were approved by the FCCC Institutional Animal Use and Care Committee (IACUC).

Media and cells: were as previously described (12-15) except for mouse embryonic fibroblasts (MEF) that were prepared according to standard methods (37) from day 12-14 embryos and were maintained in DMEM containing 15% fetal bovine serum (FBS) and antibiotics.

Viruses and infections: Stocks of WT vaccinia virus (VACV) Western Reserve were produced in tissue culture as before (17, 21, 22, 26). Stocks of ectromelia virus (ECTV) were produced in A9 cells. For ECTV multi-step growth curves, BS-C-1 or A9 cells were infected with ECTV at an MOI of 0.01 for 1 hour. Unabsorbed virus was removed by washing the cells with PBS three times, and the cells were incubated at 37° C. 5% $CO_2$ in 3 ml of DMEM containing 2.5% FBS. At various times PI, supernatants and cells were harvested separately and virus titers were determined. All growth analyses were performed in triplicate. VACV and ECTV titers in stocks, tissues and cells were as before (17, 21, 22, 26). Vesicular Stomatitis Virus (VSV) Indiana strain was expanded in A9 cell and the viral yield was determined by a plaque assay on Vero cells. To generate Δ166, we used an adaptation of the method of homologous recombination (17). See FIG. 1. Briefly, a construct containing the 5' 300 by of ECTV EVM166 the early/late OPV 7.5 promoter, the complete sequence of enhanced GFP (EGFP) and the 3' 300 by of EVM166 in that order was cloned into plasmid Bluescript II SK+. This targeting vector was used to transfect mouse A9 cells using Lipofectamine 2000 as per manufacturer instructions (Invitrogen). The transfected cells were infected with wild type ECTV (Moscow strain, 0.3 pfu/cell) in 6 well plates. Two days later, transfected/infected A9 cells were harvested using a rubber policeman, frozen and thawed and different dilutions of cell lysates were used to infect BS-C-1 cells in 6 well plates. Two hours after infection, the cells were overlaid with media containing 0.5% agarose. Four days later, green-fluorescent plaques (FIG. 1b) were picked with a pipette tip and used to infect a new set of cells. The purification procedure was performed 5 times until all plaques were fluorescent. The viral DNA from ≈300 by downstream and upstream of EVM 166 was amplified by PCR, cloned and sequenced. An isolate with the correct sequence was expanded for subsequent experiments with the same methods as for WT virus. To generate Rev166, a procedure similar to that for Δ166 was used but the targeting vector contained the whole coding sequence of EVM166 and the target virus was Δ166. Non-fluorescent plaques were amplified (FIG. 1c). For mouse infections with ECTV, mice were inoculated with 300 PFU of the various ECTV in the left hind footpad in 50 μl PBS. It should be noted that in the past (26), we have used Balb/c mice from the FCCC stock where 20-40% survival was frequently observed with 3,000 PFU ECTV WT while the LD50 that we recently determined for Balb/c mice from NCI (and also from Jackson Laboratories) is ~0.1 PFU. The reason for this difference in susceptibility to lethal mousepox in Balb/c mice from different origins is unknown. Mice were monitored for signs of mousepox and death as described previously (17, 21, 22, 26). VACV infection was performed as before (17, 21, 22, 26). For NK cell depletions, mice were inoculated intraperitoneally with 10 μl of anti-Asialo GM1 antibody (Wako Pure Chemical Industries, Ltd.) 1 day before viral infection.

Flow cytometry: Performed as described previously (17, 21, 22, 26).

Production and use of Rec eIFN-α bp: The coding sequence for eIFN-α bp without the signal peptide (residues 1-31) was amplified by PCR from viral DNA and inserted into vector pET28 (Novagen) with a C-terminal His tag. Expression and refolding of Rec eIFN-α bp was as previously described for EVM135 (26) except that removal of urea was performed by serial dialysis overnight against 6, 4, 2, 1 and finally 0 M urea. To determine Abs to eIFN-α bp in sera from infected or immunized mice, 96-well bottom ELISA plates (Corning) were coated with 100 ng recombinant eIFN-α bp or lysates of VACV-infected cells ($1 \times 10^7$ PFU/ml) in 0.1 ml of PBS at 4° C. overnight. Plates were blocked for 2 h at 37° C. with PBS containing 1% BSA. Mice sera were serially diluted in PBS containing 0.5% BSA, 0.05% Tween 20, and 0.1 ml was added to each well. The plates were then incubated for 1 h at 37° C. and washed three times with PBST (PBS with 0.05% Tween 20). 0.1 ml of peroxidase-conjugated affinity purified goat anti-mouse IgG (γ chain specific, KPL) were added to each well at a dilution of 1: 2000, incubated for 0.5 h at 37° C., and then washed five times with PBST. 50 ul of SureBlue TMB 1-Component Microwell Peroxidase Substrate (KPL) was added to each well and the reaction stopped by addition of 0.1 ml 0.12 M HCl. The optical density (OD) at 450 nm was determined using a microplate spectrophotometer (μQuant, Bio-Tec). To determine binding of Rec eIFN-α bp to IFN-α, 96-well bottom ELISA plates were coated with 200 IU of recombinant mouse IFN-α and blocked as above. Serially diluted Rec eIFN-α bp protein or control EVM135 (26) in 0.1 ml of PBS were added to each well and incubated for 2 h at 37° C. After three washes with PBST, 0.1 ml of a 1/100 dilution in PBS of sera harvested from B6 mice infected three weeks previously with either Rev166 or Δ166 was added. The plates were incubated 0.5 hours at RT. This was followed by peroxidase-conjugated affinity purified goat anti-mouse IgG, substrate and optical density determination as above. To determine the biological activity of Rec eIFN-α bp in vitro, $2 \times 10^5$ MEF were seeded into 24-well-plates. The following day, different amounts of Rec eIFN-α bp were added for 2 h at 37° C. in 0.5 ml DMEM 10% FBS followed by the addition of the indicated amounts of mouse IFN-α or IFN-β. After overnight incubation, the cells were infected with $10^8$ PFU/well VSV in 0.5 ml of DMEM 2.5% FBS. After one hour incubation, the media was replaced with 1 ml of complete DMEM 10% FBS and the cells were incubated overnight. The cells were washed twice with PBS and the MEF monolayer was visualized by fixing with methanol and staining with 1% of crystal violet. To determine neutralization of the biological activity of Rec eIFN-α bp with immune sera, the assay was performed as above but the indicated amounts of heat-inactivated (56° C. 30 min) sera from infected (three weeks PI) or immunized (see below) mice were added to MEF in 0.5 ml DMEM 10 1 h before the addition of Rec eIFN-α bp. To determine the biological activity of Rec eIFN-α bp in vivo, mice were inoculated i.v. with 50 µg Rec IFN-α bp in 0.5 ml PBS immediately and 3 days PI with ECTV Δ166. A group of control infected mice received PBS instead of Rec eIFN-α bp while a second control group received Rec eIFN-α bp but remained uninfected. Mousepox and death was determined as previously described (17, 21, 22, 26). For immunizations, male Balb/c mice were immunized every other week, three times with 20 µg Rec eIFN-α bp or recombinant human HER2/neu emulsified in incomplete Freund's adjuvant (IFA). Both recombinant proteins were produced in *E. coli*. Three weeks after the last immunization, the mice were bled to determine Ab in serum and infected with WT ECTV two days later.

Statistics: Data was analyzed using Excel Analysis Tool Pack (Microsoft).

Results eIFN-α bp is Essential for ECTV Virulence

Figure 1B:
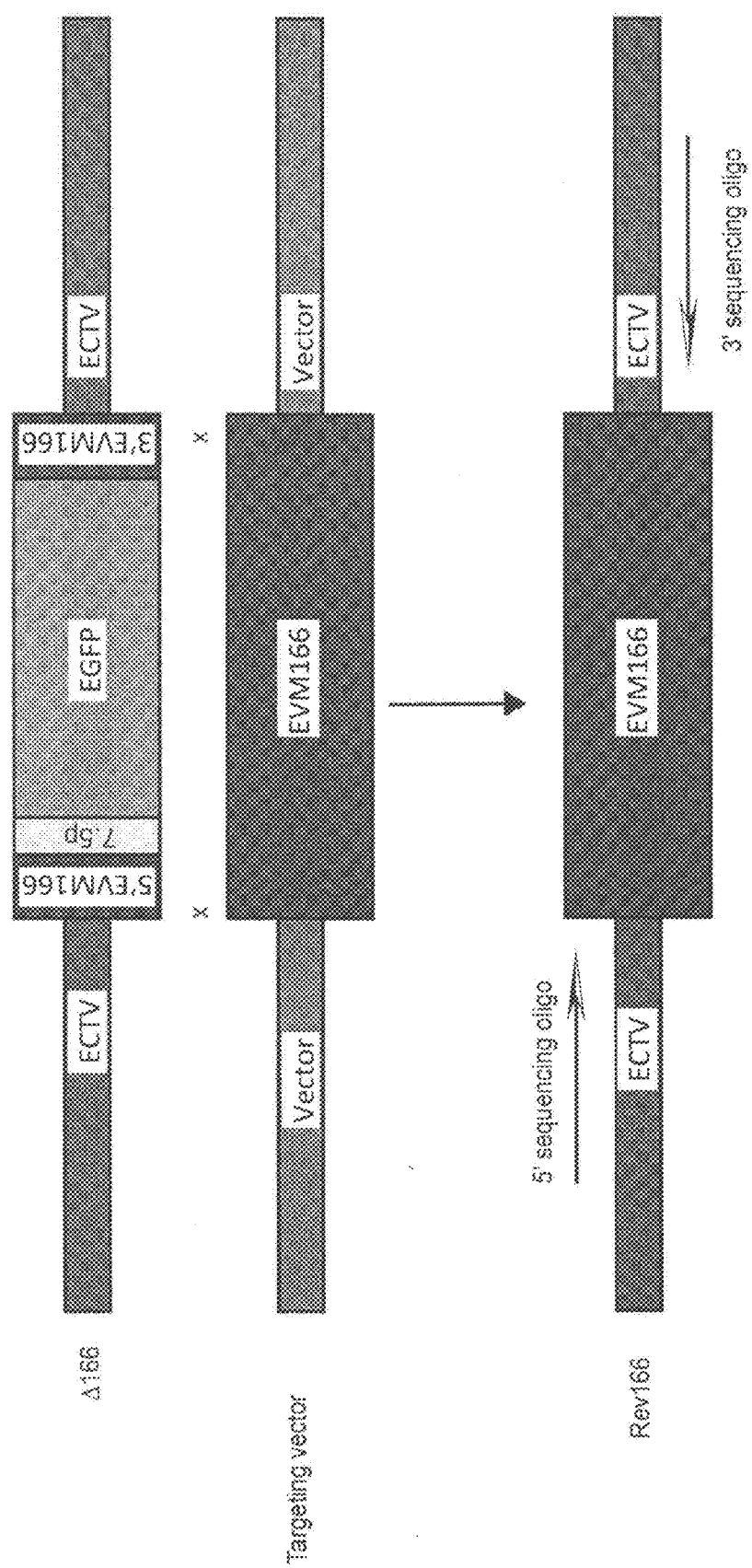
Figure 1C:
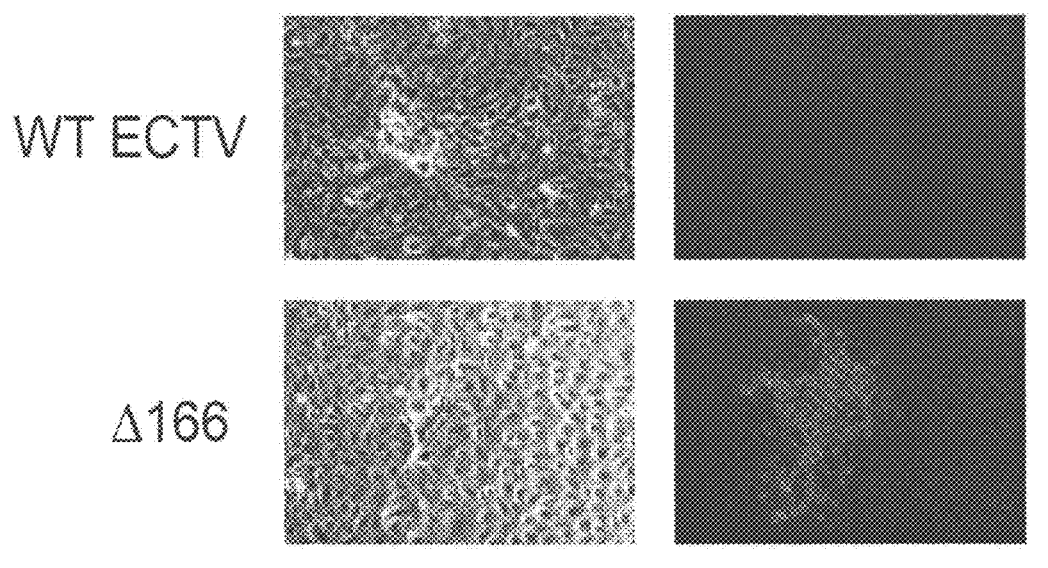
Figure 2A:
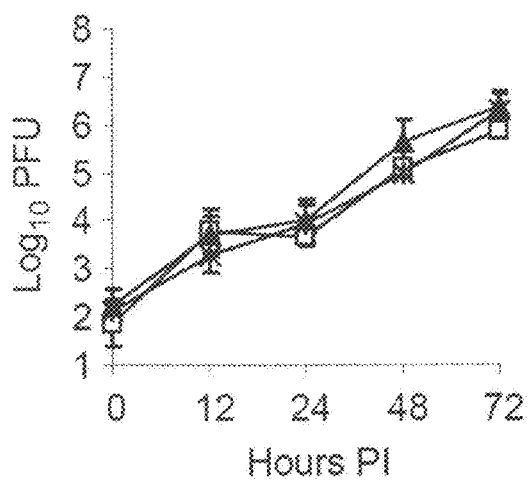
FIG. 2a) Mouse fibrosarcoma A9 cells were infected with 0.01 PFU/cell of the indicated viruses. Cell associated and free virus was determined at the indicated times after infection. Data points are means±SD of three replicate wells.

To elucidate the importance of the eIFN-α bp in ECTV virulence, we produced a mutant ECTV (Δ166) where EVM166 was replaced with enhanced green fluorescence protein (EGFP) (17) (FIG. 1a). In addition, as a control for any defects that Δ166 may had acquired in other loci during cloning, we also generated a revertant virus (Rev166) where EVM166 was reintroduced to its original location in Δ166 (FIG. 1b). In initial experiments to characterize the viruses we found that ECTV Δ166, Rev166 and WT produced similar amounts of infectious virus in multi-step growth curves as determined in mouse A9 cells (FIG. 2a) and also in monkey BSC-1 cells (not shown). This indicated that eIFN-α bp was not required for replication in tissue culture and is consisted with expectations for a non-structural secreted protein that does not play a role in DNA replication or virus assembly.

Figure 2B:
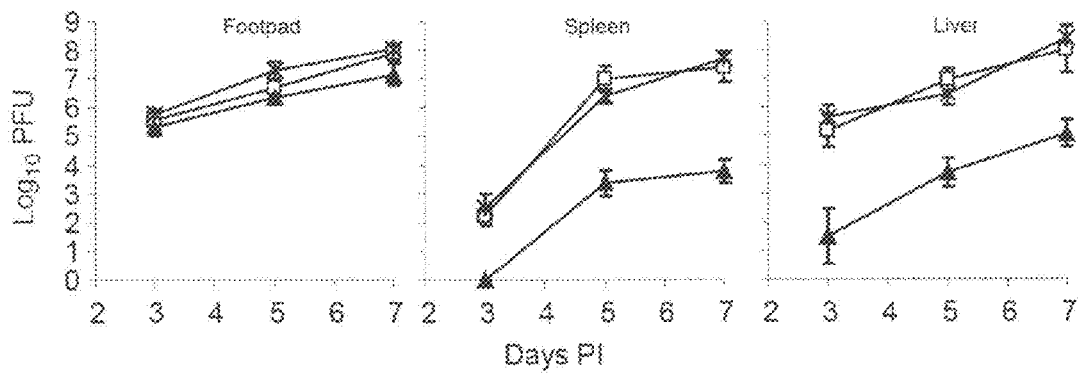
FIG. 2b) Balb/c mice were infected with 300 PFU of the indicated viruses. Virus titers in the infected footpad and spleen were determined at the indicated times. Data points are means±SD of three mice.

The natural route of ECTV entry is through microabrasions of the footpad (18). Via this route, it first multiplies at the site of entry followed by spread to and replication in the local draining lymph node (D-LN). From there, ECTV follows the efferent lymphatic vessels to reach the blood and then visceral organs such as the liver and the spleen (18). In mousepox susceptible strains such as Balb/c, WT ECTV reaches very high titers in these organs. Thus, to determine whether eIFN-α bp is important for efficient replication and spread in vivo, we infected Balb/c mice in the footpad with 300 plaque forming units (PFU) of ECTV Δ166, Rev166 or WT. Three, five, and seven days post infection (PI), we quantified virus loads in the infected footpad to determine local replication, and the spleen and liver to determine spread (FIG. 2b). The results showed that eIFN-α bp is not very important for replication at the initial site of infection because only minor differences in virus loads of the three viruses were found in the infected footpads at every time PI. However, the virus loads of Δ166 were ~$10^4$ and ~$10^3$ fold lower in spleen and liver, respectively, than those of WT or Rev166 indicating that eIFN-α bp is required for the efficient spread of ECTV to visceral organs.

Figure 2C:
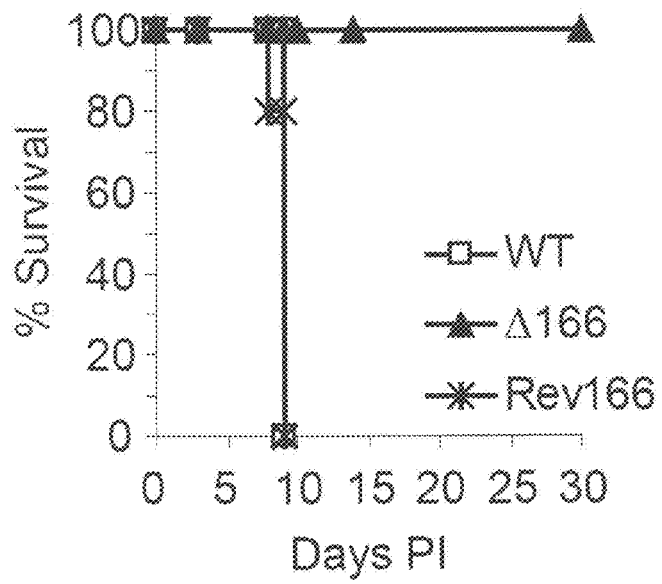
FIG. 2c) Balb/c mice were infected in the footpad with 300 PFU of the indicated viruses. Mice were observed for survival. Data corresponds to five mice/group.
Figure 3:
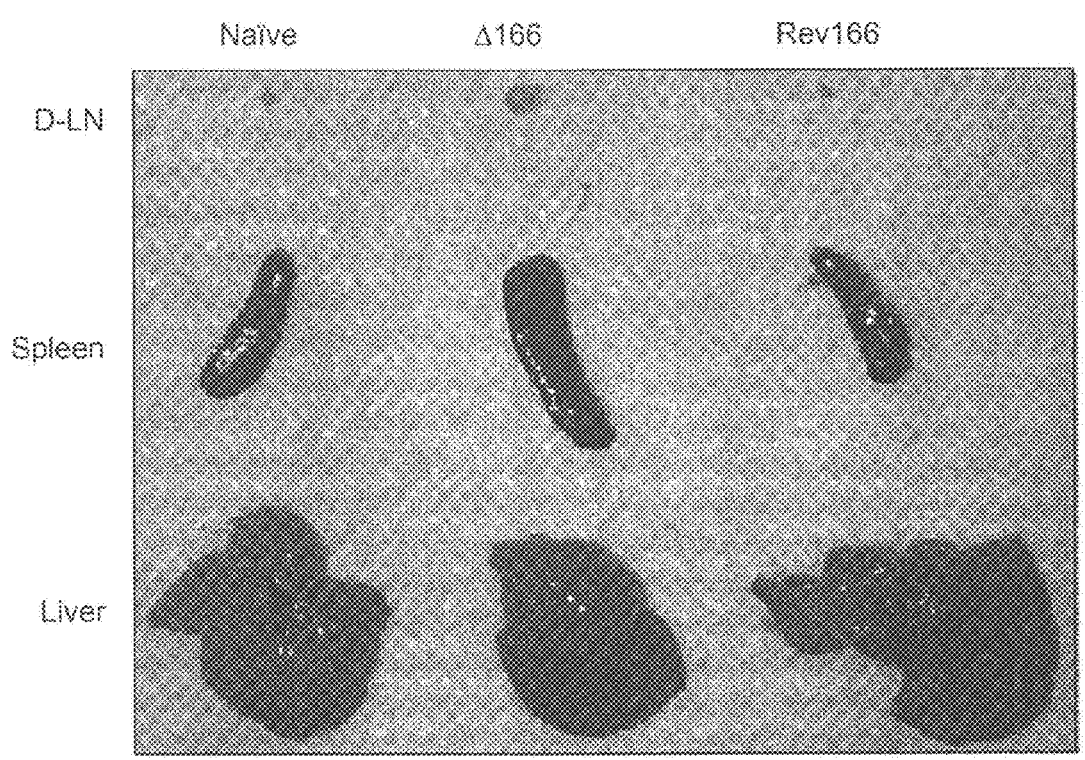
FIG. 3. Enlarged lymphoid organs and reduced liver pathology in Balb/c mice infected with D166. Mice were infected with the indicated viruses and organs harvested and photographed seven days PI.

In mousepox susceptible Balb/c mice, the massive replication of ECTV in the liver results in acute liver necrosis and death within 8-11 days PI. Any Balb/c mouse that survives this phase develops a typical skin exanthema and experiences weight loss of 25-30% of the initial body weight (14-17). Thus, to determine the role of eIFN-α bp in ECTV virulence we infected Balb/c mice with 300 PFU of ECTV Δ166, Rev 166 or WT. Strikingly, all of the mice infected with Δ166 survived while all of those infected with Rev166 or WT succumbed (FIG. 2c). Moreover, none of the mice infected with Δ166 demonstrated overt symptoms of mousepox or major weight loss (not shown). Consistent with these results, infection with Δ166 resulted in decreased anatomical pathology in organs. Macroscopic observation showed that, as expected, the D-LNs and spleen of mice infected with WT ECTV were reduced in size compared to naïve mice and their spleens and livers were necrotic. Conversely, the D-LNs and spleens of mice infected with Δ166 were enlarged and their livers had a normal appearance (FIG. 3). In additional experiments we found that the dose of ECTV WT or Rev166 that killed 50% (LD50) of Balb/c mice was 0.1 PFU while as little as 1 PFU resulted in the death of 100% of the mice (not shown). In contrast, no deaths were observed in Balb/c mice (n=5) infected with $10^7$ PFU Δ166, the maximum dose that our virus stock permitted. Thus, from these experiments we conclude that Δ166 is attenuated at least $10^8$ fold considering 0.1 PFU the LD50 for WT and Rev166, and >$10^7$ for Δ166. Because Rev166 was as virulent as WT, we also conclude that the only defect of Δ166 is in the production of eIFN-α bp. Together, this set of data demonstrates that eIFN-α bp is essential for ECTV virulence.

eIFN-α bp Decreases Innate and Adaptive Immunity

Figure 4A:
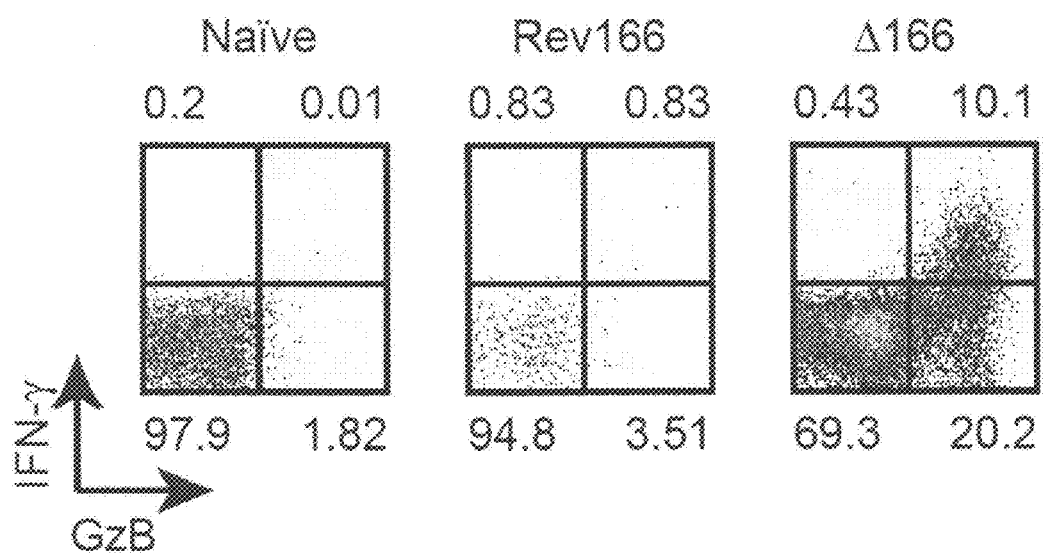
FIG. 4a) Mice were infected with the indicated viruses. Five days PI, anti-ECTV CD8+ T cell responses were determined in the popliteal draining lymph node (D-LN). Plots are gated on CD8+ cells. Data corresponds to a pool of three LN and is representative of three similar experiments.

We and others have shown that T cells are essential for the natural resistance of B6 mice to mousepox (18-21) and that a very strong T cell response can be detected in the D-LN of B6 mice 5 days PI (22). We have also recently shown that, in contrast to B6 mice, the T cell response to WT ECTV in the D-LN of mousepox-susceptible naïve Balb/c mice is almost undetectable (17). Interestingly, naïve Balb/c mice mounted a very strong $CD8^+$ T cell response to Δ166 but, as we showed previously, not to Rev166 (FIG. 4a). A similar observation was made for the $CD4^+$ T cell response (not shown). In addition, we also found an increase in the T cell response to Δ166 as compared to Rev166 in mousepox resistant B6 mice (not shown). Thus, one major effect of eIFN-α bp is to decrease the T cell response.

Figure 4B:
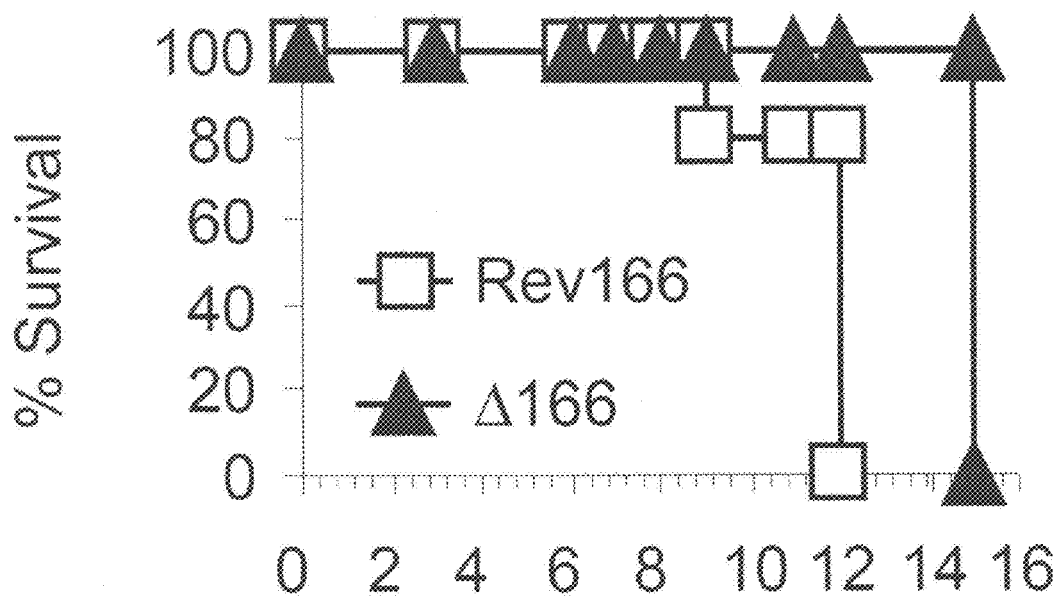
FIG. 4b) RAG-1 KO mice were infected with the indicated viruses and observed for survival. Data corresponds to five mice/group.
Figure 4C:
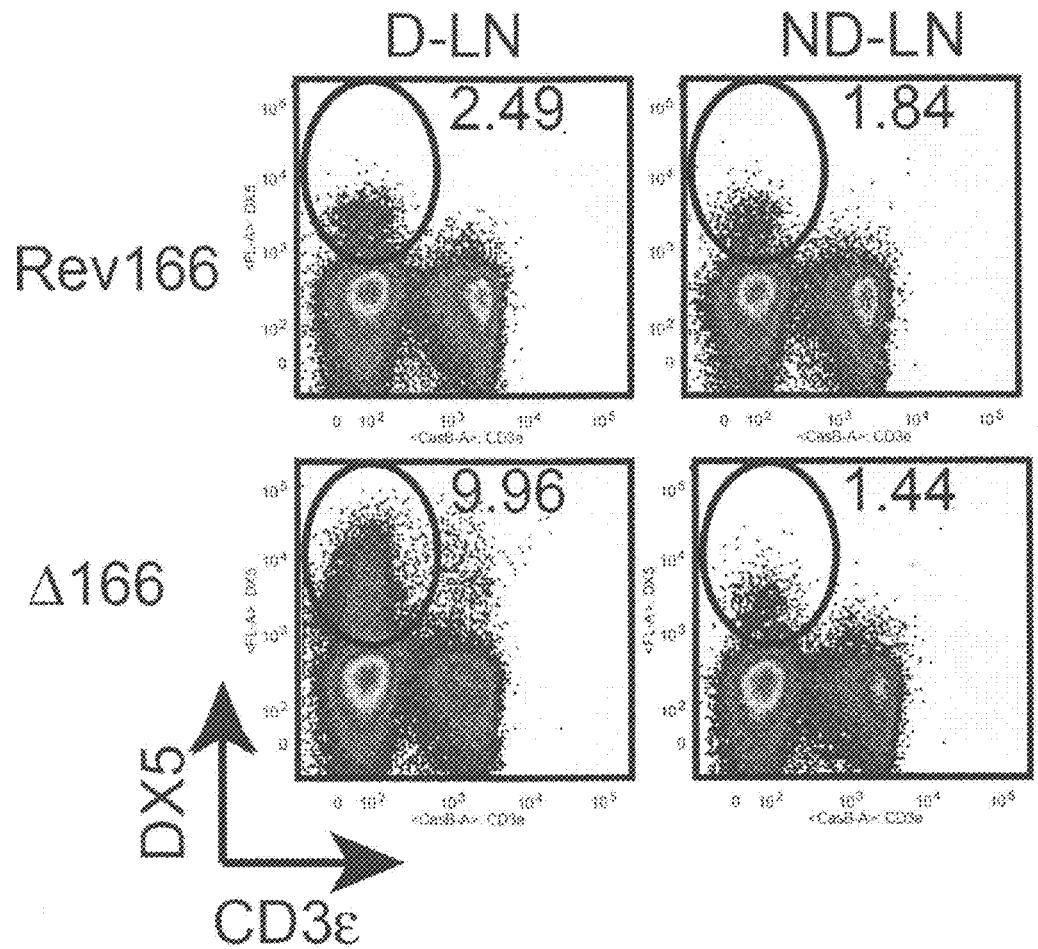
FIG. 4c) Balb/c mice were infected with the indicated viruses. Three days PI, cells from the D-LN and contralateral non-draining lymph node (ND-LN) were stained as indicated. Data corresponds to a pool of three LNs and is representative of two experiments.
Figure 4D:
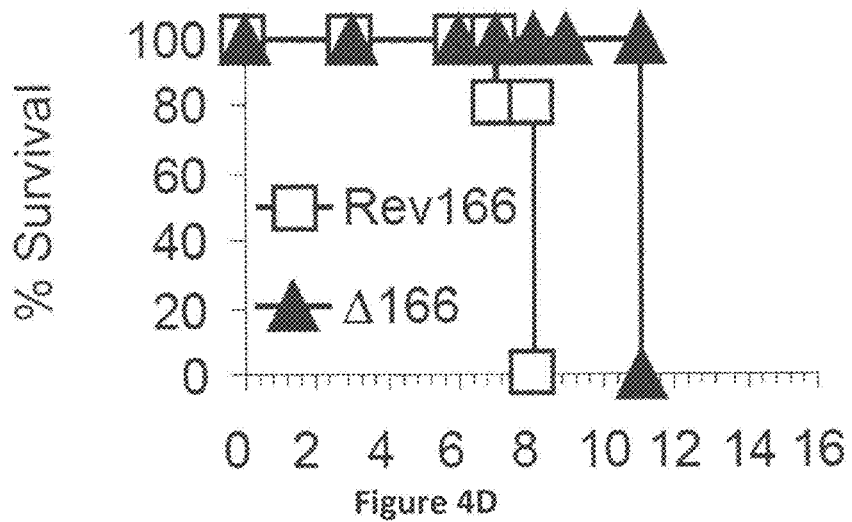
FIG. 4d) RAG-1 KO mice depleted of NK cells using anti-Asialo-GM1 antibody were infected with the indicated viruses and observed for survival. Data corresponds to five mice/group.

We next tested whether eIFN-α bp may also affect innate immunity. When RAG-1 KO mice (that lack adaptive immunity) were infected with Δ166, they succumbed to mousepox but several days later than those infected with Rev166 (FIG. 4b) indicating that in addition to adaptive immunity, eIFN-α bp affects innate immunity. We reasoned that NK cells might be one component of innate immunity affected by eIFN-α bp because NK cells are essential for resistance to mousepox (24, 25). In addition, recent experiments from the Buller laboratory (25) as well as our own experiments showed that on day 2 PI, ECTV recruits NK cells to the D-LN. ECTV Δ166 recruited in excess of four times more NK cells to the D-LN than Rev166 (FIG. 4c) or WT (not shown) indicating that one effect of eIFN-α bp on innate immunity is to reduce the recruitment of NK cells to the D-LN. However, eIFN-α bp must also affect components of innate immunity other than NK cells (e.g. macrophages and/or polymorphonuclear cells) because RAG-1 KO mice depleted of NK cells with anti-Asialo GM1 Ab and infected with ECTV Δ166, succumbed to mousepox later than those infected with Rev166 (FIG. 4d).

eIFN-α bp is a Natural Target of the Anti-OPV Ab Response

Infection with OPVs induces strong Ab response against multiple structural components of the virions (21, 24-26).

Figure 5A:
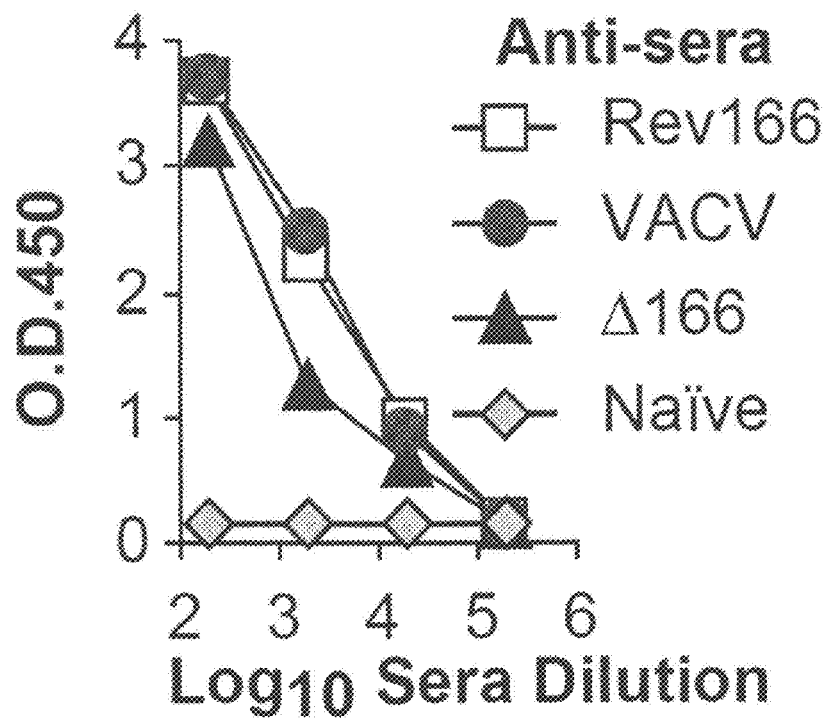
FIG. 5a) Sera from mice infected with the indicated viruses was tested for anti-ECTV antibodies in ELISA using virus particles (infected cell lysates) as antigen.
Figure 5B:
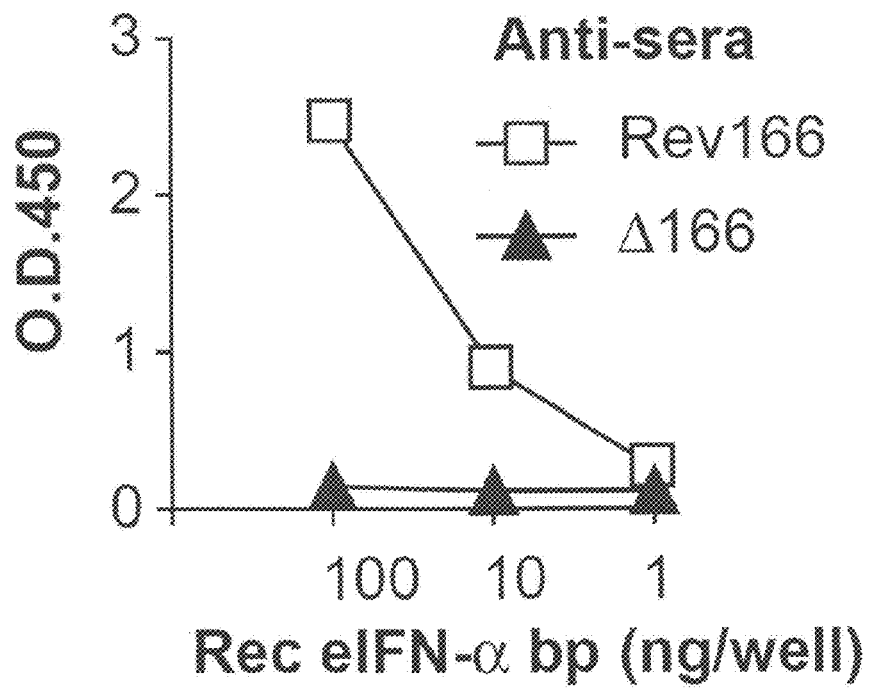
FIG. 5b) Wells of ELISA plates were covered with 200 IU of recombinant mouse IFN-α and treated with the following reagents in that order: the indicated amounts of Rec eIFN-α bp, sera from mice immune to ECTV Δ166 or Rev 166 as indicated, peroxidase labelled goat anti-mouse IgG, and TMB substrate.
Figure 5C:
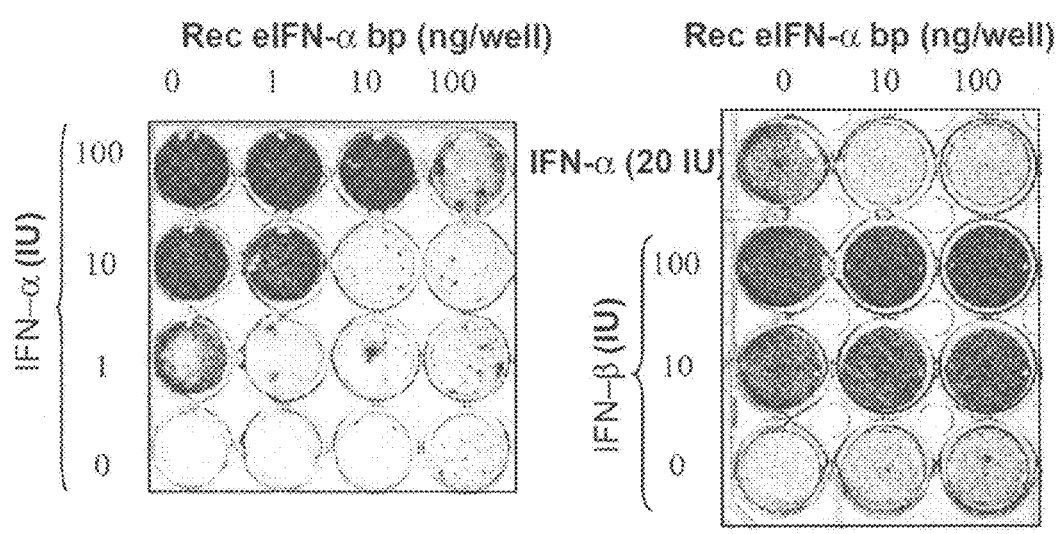
FIG. 5c) MEFs were incubated with the indicated amounts of IFN-α or -β for 24 h in the presence or in the absence of the indicated amounts of Rec eIFN-α bp. MEF were next infected with VSV and after additional 24 h, fixed and stained with 1% crystal violet.
Figure 5D:
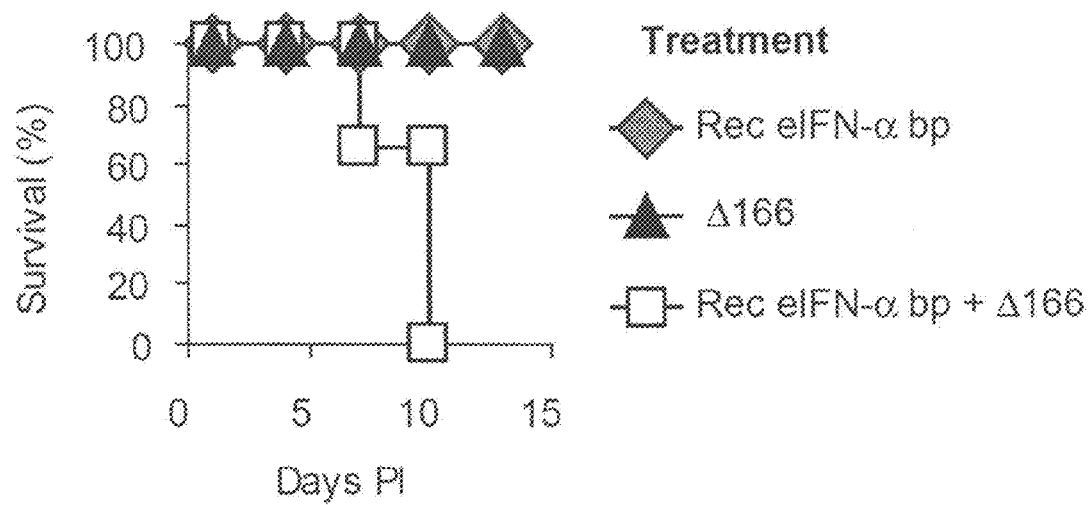
FIG. 5d) As in (a) but using Rec eIFN-α bp as antigen.

Consistent with this, anti-sera to ECTV WT, Δ166 or Rev166 contained Abs that recognized virions in cell lysates (FIG. 5a). However, whether secreted IRMs can also be targets of the Ab response, is not known. This question is important because Abs capable of blocking the function of IRMs essential for virus virulence could contribute to protective immunity. To elucidate whether eIFN-α bp is a natural target of the Ab response, we cloned and produced in E. coli recombinant His-tagged eIFN-α bp (Rec eIFN-α bp) which was recovered from inclusion bodies and purified by $Ni^{2+}$-affinity chromatography (not shown). After refolding, Rec eIFN-α bp bound IFN-α (FIG. 5b), inactivated IFN-α but not –β in tissue culture (FIG. 5c) and, more interestingly, complemented Δ166 in vivo: i.e. when Balb/c mice infected with Δ166 were also inoculated with Rec eIFN-α bp, they succumbed to mousepox (FIG. 5d) but not when inoculated with rec IFN-α bp alone. We next used Rec eIFN-α bp as antigen in ELISA to demonstrate that C57BL/6 mice that recovered from infection with Rev166 had high titer Abs to eIFN-α bp (FIG. 5e, squares) indicating that, indeed, eIFN-α bp is a natural target of anti-ECTV immunity. Sera from Balb/c mice that had been infected with vaccinia virus (VACV, the OPV used as the smallpox vaccine) also reacted with Rec eIFN-α bp (FIG. 5e, circles) indicating that VACV infection induces Abs to the eIFN-α bp homolog (B18R) and that Abs to the two proteins are cross-reactive. As expected, mice that had been infected with Δ166 did not have Abs to eIFN-α bp (FIG. 5e, triangles). Even more important, sera from mice that recovered from Rev166 but not from Δ166 infection had the capacity to block the biological activity of Rec eIFN-α bp in tissue culture (FIG. 5f) suggesting that Abs to eIFN-α bp may have protective effects in vivo.

Immunization with Recombinant eIFN-α bp Prevents Lethal Mousepox

Figure 6:
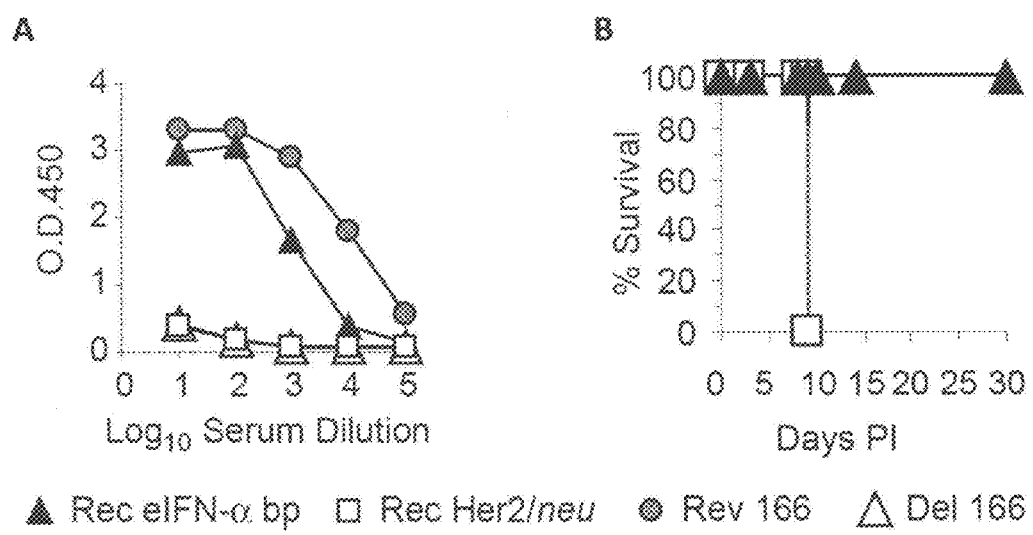
FIG. 6. Immunization with Rec eIFN-α bp protects from mousepox.

Given that eIFN-α bp is essential for ECTV virulence in Balb/c mice and that Abs can neutralize its effects in vitro, we next tested whether immunization with Rec eIFN-α by induced a protective immune response. As expected, sera from Rec eIFN-α bp immunized Balb/c mice had high Ab titers to eIFN-α bp (FIG. 6a) and also neutralized the biological activity of Rec eIFN-α bp but not ECTV infectivity in tissue culture (not shown). Strikingly, all Balb/c mice immunized with Rec eIFN-α bp and challenged with 300 PFU ECTV WT (i.e. $3 \times 10^3$ LD50) survived the infection with minimal weight loss (~10%), while all mice immunized with control Rec human Her2/neu perished (FIG. 6b). Thus, anti-eIFN-α bp antibodies protect from mousepox and Rec eIFN-α bp can be successfully used as a vaccine to prevent it.

Figure 7:
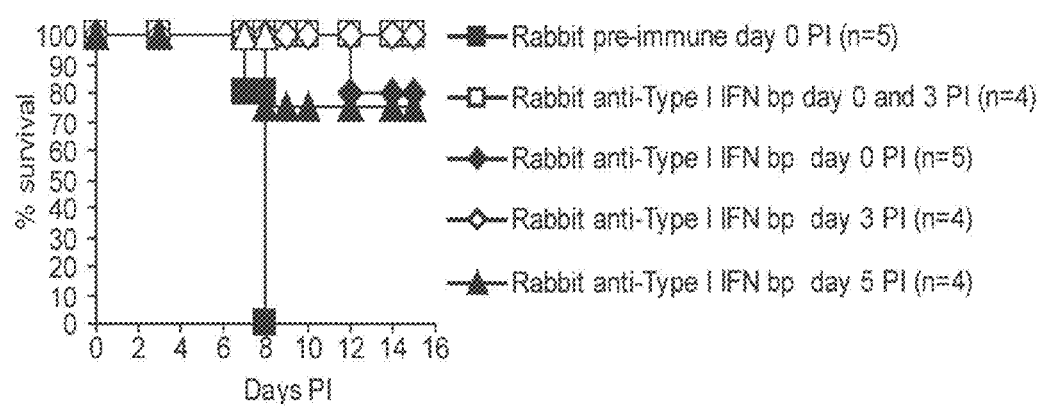
FIG. 7. Rabbit anti-IFN-α bp sera protects from mousepox pre- and post-exposure. BALB/c mice were infected with 3,000 PFU ECTV in the footpad, treated as indicated and survival monitored.

Immunization with Sera Obtained from Rabbits Exposed to Recombinant eIFN-α by Prevents Lethal Mousepox To test whether passive immunization with Abs to eIFN-α bp can protect from mousepox before and/or after exposure to ECTV, we immunized rabbits with Rec eIFN-α bp. ELISA experiments showed that their sera contained high titer Ab to the protein (not shown). To determine whether these rabbit Abs to eIFN-α bp can protect mice from mousepox either pre- or post-exposure, mice infected with ECTV (3000 PFU) were given 100 μl of the rabbit antisera twice on days 0 (before infection) and 3, or once on days 0, 3 or 5 PI. Mice receiving pre-immune sera served as a control. The data in FIG. 7 show that strong protection was achieved even for mice that received sera as late as day 5 PI. This data demonstrates that Abs to virulence factors can protect from OPV pre- and post-exposure.

We have also produced monoclonal Abs (mAbs) specific for the eIFN-α bp and tested one of them for protection. We found that one single dose of 1 mg mAb on day 2 PI protected 60% of the mice from mousepox and death and delayed death in the remaining 40% by 5-10 days (not shown). Thus, protection from viral infection can be obtained using a mAb directed against a target SPVP.

Figure 8A:
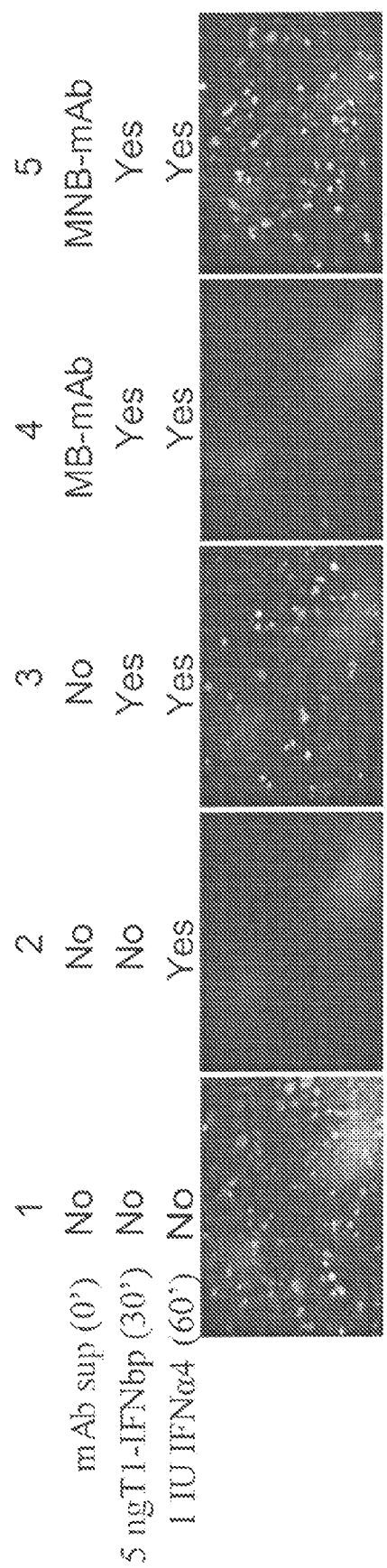
FIG. 8. Characterization of MB-mAb and MNB-mAb. Mabs were produced by fusing the splenocytes from mice immunized with recombinant T1-IFNbp-ECTV with SP2cells. Hybridomas producing anti-T1-IFNbp mAbs were selected using an ELISA assay. A) Identification of MB-mAb and MNB-mAb: MB- and MNB-mAb were identified in a biological assay where L cells were treated as indicated followed by infection with vesicular stomatits virus (VSV) expressing GFP. The cells were observed at the microscope 24 hours later. Results were as follows: Column 1: With no treatment, many cells were infected by the virus (many green cells). Column 2: Addition of IFNα prevented infection (no green cells). Column 3: Addition of recombinant T1-IFNbp-ECTV neutralized the activity of IFNα and the cells became infected again (many green cells). Column 4: Addition of MB-mAb prevented T1-IFNbp-ECTV from blocking IFNα (no green cells). Column 5: Addition of MNB-mAb did not prevent T1-IFNbp-ECTV from blocking IFNα. B) Both MB-mAb and MNB-mAb stain infected and uninfected cells in mixed cultures as the IFNbp will be elaborated from infected cells and bind to membranes of neighboring uninfected cells. L cells were infected with 0.1 PFU ECTV-GFP or ECTV-Δ166-GFP. The next day, the cells were stained with MB-mAb or MNB-mAb followed by anti-mouse Alexa647 and analyzed by FACS. In cultures infected with ECTV-GFP (left panels), both infected (GFP+, right quadrants) and uninfected cells (GFP-, left quadrants) were stained by both mAbs (all the cells were in the upper quadrants, T1-IFNbp+). As expected, when cultures were infected with the virus that lacks the T1-IFNbp (right panels), infected (GFP+, right quadrants) and uninfected cells (GFP-, left quadrants) did not stain with anti-T1-IFNbp (all cells in the lower quadrants, T1-IFNbp-). C) MB-mAb recognizes T1-IFN-bp-MPXV: Hela cells were incubated for 1 hour with recombinant EVM135 as a negative control (redlines/curves to the left in each panel), or, as indicated, with recombinant T1-IFNbp-VARV, supernatant of MPXV infected cells, supernatant of VACV infected cells, or recombinant T1-IFNbp-ECTV (blue lines/curves to the right in each panel). Cells were washed, incubated with MB-mAb, followed by anti-mouse IgG-FITC and analyzed by FACS. D) MB-mAb blocks the biological activity of T1-IFNbp-VARV. Hela cells were treated as indicated. Column 1: when cells where infected with VSV they were killed. Column 2: IFNα treatment did not affect the survival of uninfected cells. Column 3: IFNα protected cells from VSV. Column 4: T1-IFNbp-VARV neutralized the protective effects of IFNα. Column 5: MB-mAb blocked the T1-IFNbp-VARV restoring the protective effects of IFNα (not all the wells were adjacent as depicted). Identical results were obtained with supernatants from MPXV infected cells.
Figure 8B:
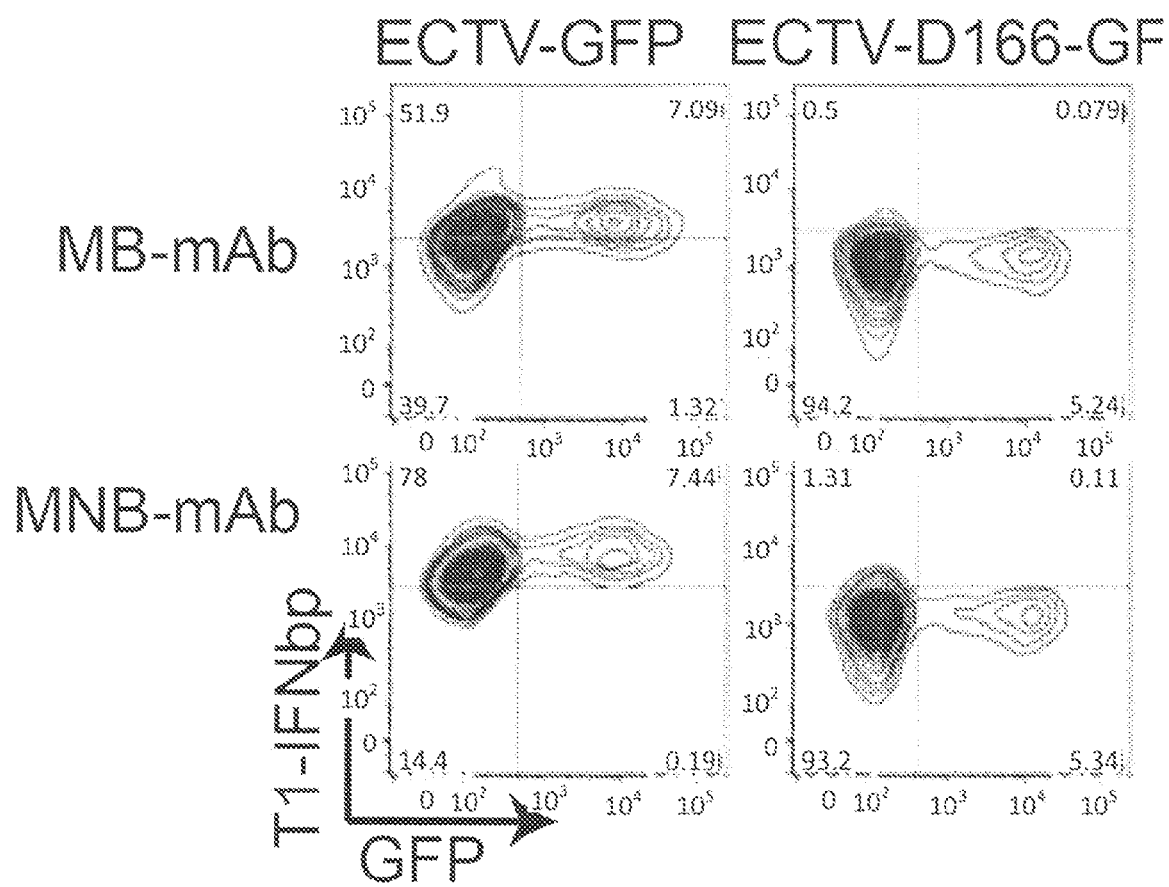
Figure 8C:
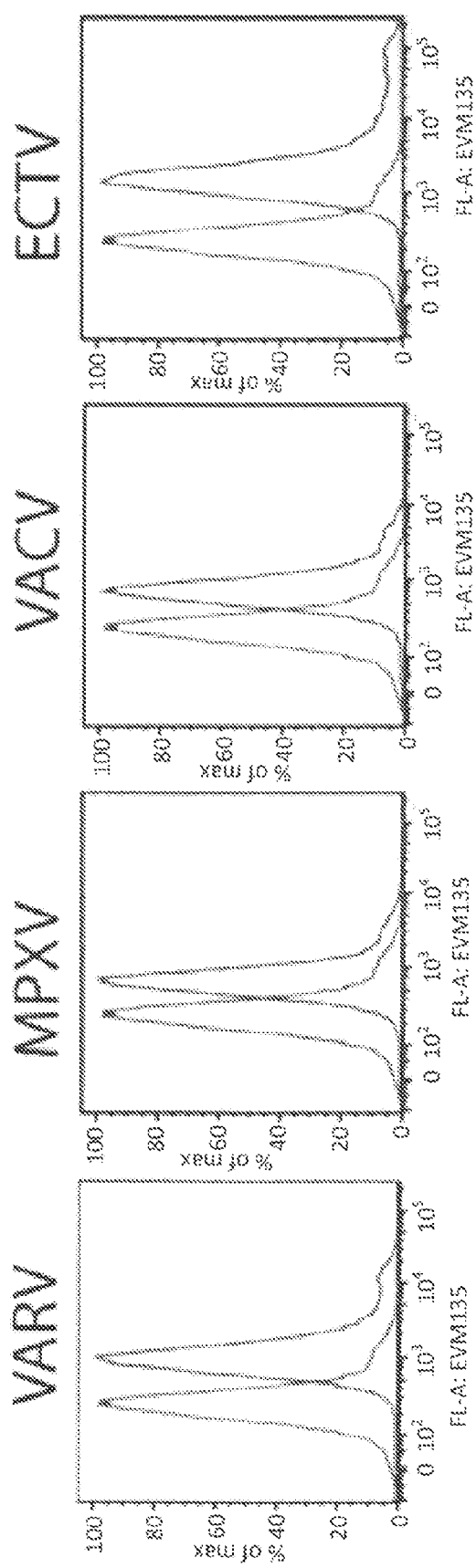

Passive Immunization with Anti-T1-IFNbp Antibodies Protects Against Mousepox by Blocking the Biological Function of T1-IFNbp To study the basis of the protective effect of anti-T1-IFNbp antibodies, we made mouse monoclonal antibodies (mAbs) against the T1-IFNbp and used a bioassay to identify a blocking (MB-mAb) and a non-blocking (MNB-mAb) (FIG. 8A). Both mAbs bound to the T1-IFNbp-ECTV as evidenced by staining cultures of infected cells (FIG. 8B). Importantly, MB-mAb (FIG. 8C) and MNB-mAb (not shown) recognized not only T1-IFNbp-ECTV but also T1-IFNbp-VARV, -MPXV and -VACV bound to the surface of cells. Moreover, MB-mAb blocked the biological activity of T1-IFNbp VARV (FIG. 8D) as well as T1-IFNbp-MPXV (not shown). The isotype of both mAbs was IgG1 (not shown), which is a poor activator of the complement cascade and ADCC.

Figure 9:
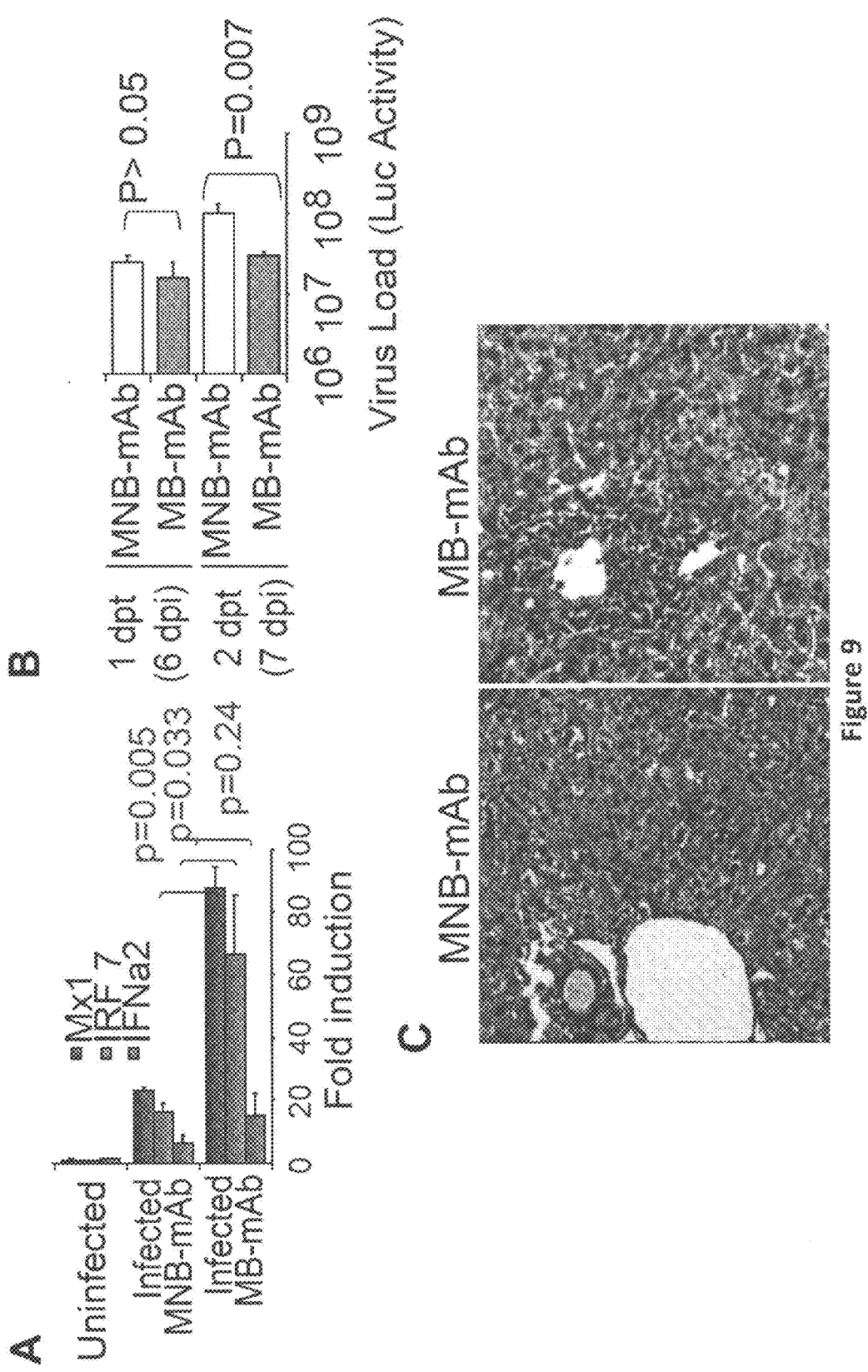
FIG. 9. MB-mAb treatment restores T1-IFN signaling in the liver and protects from lethal mouse pox late after infection. A) Mice were infected with 3,000 PFU ECTV-Luc or left uninfected. Five days post infection (dpi), mice were treated with the indicated mAbs and transcripts of the indicated genes were determined by qPCR one dpi. Indicated genes are as follows in descending order: "MX1" (myxovirus resistance 1), "IRF 7" (interferon regulatory factor 7), "IFNa2" (interferon alpha 2). B) Mice were infected with 3,000 PFU ECTV-Luc. Five dpi, mice were treated with the indicated mAbs. One or two dpt, the mice were sacrificed and virus loads in the liver were determined by Luc activity. C) Mice were infected with 3,000 PFU ECTV-Luc. Five dpi, mice were treated with the indicated mAbs. Two days post treatment (dpt), the livers were collected and sections stained by H & E. D) As in B), but analyzed two dpt the mice were inoculated IP with luciferase substrate, anesthetized and analyzed by whole body imaging using a Carestream in vivo imaging system (Rochester, N.Y.). Luciferase activity scale is on the right side of the figure. E) Mice were infected with WT-ECTV and treated as indicated 5 dpi. Survival was monitored. Statistics: Isotype control vs. MNB-mAb, P=0.4; Isotype Control vs. MN-mAb P=0.0006; MNB-mAb vs. MB-mAb, P=0.005 by Log-rank Mantel-Cox test.
Figure 9E:
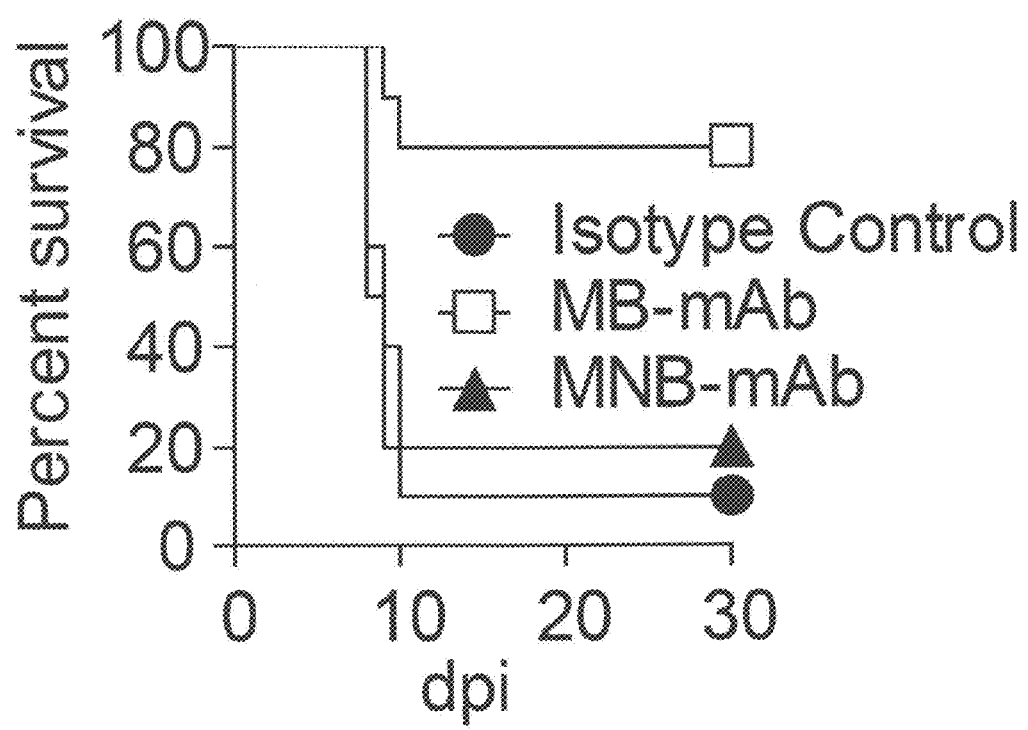

MB-mAb and MNB-mAb were compared for ability to protect against lethal mousepox using BALB/c mice infected with ECTV-Luc. Five days post infection (dpi) the mice were treated with MB-mAb and MNB-mAb, and their livers were collected 1 (day post treatment (dpt). We found that the mice treated with MB-mAb had a significant increase in the transcription of the ISGs Mx1 and IRF7 as compared with mice treated with MNB-mAb, even though there were no differences in the transcription of T1-IFN genes (only IFNα2 is shown, FIG. 9A), demonstrating that MB-mAb blocks the function of the T1-IFNbp in vivo and reestablishes T1-IFN signaling. Moreover, 1 dpt (6 dpi), the livers of mice treated with MB-mAb had marginal but significantly lower virus titers than the livers of mice treated with MNB-mAb, and this difference increased substantially 2 dpt, as detected by Luc activity in liver lysates (FIG. 9B). The differential effect on virus loads between MB-mAb and MNB-mAb 2 dpt can also be appreciated by in vivo whole animal imaging (FIG. 9C). Moreover, while the livers of mice treated with MNB-mAb were almost completely necrotic (indicated by the pink/bright areas lacking nuclei) and devoid of a mononuclear infiltrate, the livers of mice treated with MB-mAb showed only small areas of necrosis and had heavy infiltrates of mononuclear cells, in particular in the portal triad, which is indicative of an immune response (FIG. 9D). Finally, while mice treated with MNB-mAb succumbed to infection as readily as mice treated with control mouse IgG1, the mice treated with a single dose of MB-mAb 5 dpi were significantly protected from lethal mousepox while mice treated with MNB-mAb were not (FIG. 9E). Because MB-mAb protected while the MNB-mAb did not (even though both antibodies recognize T1-IFNbp at the surface of cells), these results demonstrate that protection is due to the blockade of the biological function of the T1-IFNbp and not to other immune mechanisms such as complement activation or antibody dependent cellular cytotoxicity (ADCC). These results are also consistent with the isotype of the mAbs, because IgG1 is not very effective in complement activation or ADCC. This is a desirable result because these two processes could induce immunopathology.

A MB-mAb to the T1-IFNbp-ECTV restores T-IFN signaling in the liver and is effective as a late therapy for an OPV disease. This MB-mAb is cross-reactive with T1-IFNbp-MPXV and T1-IFNbp-VARV. Together, these results provide supporting evidence that Abs that block T1-IFNbp-MPXV or T1-IFN-VARV can be effective as a therapy for MPXV VARY and other emerging OPV infections in humans or as a therapy for complications of smallpox vaccination.

Discussion

The data described here show that the eIFN-α bp of ECTV is absolutely essential for virulence. It is interesting to mention that a VACV lacking the EVM166 ortholog B18R was found to be only mildly attenuated in mice infected through the intranasal route (8). Of note, the exact reason for this attenuation was not clear because B18R has very low affinity for type I mouse IFNs (8). In addition, VACV is not a natural pathogen of the laboratory mouse and intranasal infection of mice with VACV does not reproduce the natural pathogenesis of OPV diseases. Thus, our demonstration that Δ166 is extremely attenuated further stresses the need to explore the role of virulence factors in animal species that have natural susceptibility to the virus in question. The finding that deletion of only one protein that is non-essential for virus replication results in a virus that is attenuated at least $10^8$-fold is very surprising and indicative of the important role of eIFN-α bp in ECTV virulence. In this regard, it has recently been shown that ECTV lacking the eIFN-γ by (EVM158) is only mildly attenuated because it spread substantially in vivo, and because it induced mousepox and some deaths in susceptible Balb/c mice even at doses of 500 PFU (28). Another important question is whether the type I IFN bp, which is conserved among most OPVs, is also essential for the virulence of other OPVs in their natural hosts or whether different IRMs will be essential for each virus-host interaction. This question will be more difficult to address as it requires matching viruses with natural hosts.

IFN-α and -β are known to use the same signaling pathway to induce the anti-viral state in cells (1). Because eIFN-α bp inactivates mouse IFN-α but not -β, and because no other IFN-β blocking activity was detected in supernatants of ECTV infected cells (7), the extreme attenuation of Δ166 is intriguing. Several possibilities could explain this conundrum, all of them enticing. One possibility is that besides IFN-α binding, the eIFN-α bp protein has a second function that is essential for virulence. This second function, however, would also have to be performed in the extracellular environment because inoculation of the recombinant protein rescued virulence of Δ166 and Abs to the eIFN-α bp induced by vaccination prevented mousepox following infection with WT ECTV. Another possibility is that IFN-β is not produced or produced in insufficient quantities during ECTV infection. Finally it is also possible that the in vivo anti-viral functions of IFN-α and -β are non-overlapping.

Because of the risks of emerging OPV infections and OPV weaponization, and because the VACV based vaccine is not safe by current standards, there is a considerable interest in developing novel anti-OPV vaccines (26, 28-35). Our work also indicates that deletion of IRMs from live vaccines may be a double edged-sword. On one hand, it may increase the safety of the vaccine. However, it is also very possible that these deletions will decrease vaccine efficacy because, as we now know, the type I IFN by of OPVs are a natural target of the Ab response and are crossreactive. Thus, it is very possible that Abs to type I IFN bp and other IRMs may substantially contribute to the protective effects induced by live VACV vaccination and one of the reasons why immunization with killed virions is not very effective at inducing protection (37).

Vaccines against pathogen-secreted proteins are in use for bacterial diseases (e.g. tetanus, anthrax). However, the use of secreted virulence factors as vaccines to prevent viral diseases is unheard of. Thus, our work here provides the framework for a novel approach to anti-viral vaccination. It could be argued that such an approach may not be useful because it prevents disease but does not provide sterilizing immunity, thus maintaining the possibility of virus spread. This argument can be contested, however, because one of the biggest successes in medical history, VACV immunization, does not provide sterilizing immunity either to humans or mice (16, 17). In the case of subunit vaccines against OPVs, all approaches thus far have focused on structural proteins with some success (26, 28-30, 32). Given the strong protection induced by Rec eIFN-α bp we now propose that combining essential IRMs and structural proteins in new vaccine formulations may be the best approach for an effective and safe subunit vaccine to OPVs and possibly other viruses. In addition, our experiments open the possibility that the type I IFN bp of OPVs could be used as a pharmacological target to prevent disease in individuals exposed or at risk of exposure to pathogenic OPVs.

We also describe antibody based reagents which can be optimized and optionally humanized, such as the blocking mAb (HB-mAb) to the OPV T1-IFNbp described above. These reagents will be tested in preclinical mouse and non-human primate (NHP) models as a late therapy for OPV infections in humans. Our data suggest that a HB-mAb that promiscuously blocks the activity of T1IFNbp from various OPVs will be an effective late therapy for VARV, MPXV and other emerging OPV infections in humans, and also in cases of smallpox vaccine complications. The demonstration that a MB-mAb to the T1IFNbp-ECTV can be used as an effective treatment against mousepox at relatively late stages of ECTV infection and our finding that the MB-mAb is promiscuous because it not only binds and blocks T1-IFNbp-ECTV but also T1-IFNbp-VARV, T1-IFNbp-MPXV and T1-IFNbp-VACV is particularly intriguing. These data provide the means to exploit these reagents in new and efficacious methods for the treatment of pox infection.

References and Notes

1. Sen, G. C. 2001. Viruses and interferons. *Annual review of microbiology* 55:255-281.
2. Stetson, D. B., and R. Medzhitov. 2006. Type I interferons in host defense. *Immunity* 25:373-381.
3. Vilcek, J. 2006. Fifty years of interferon research: aiming at a moving target. *Immunity* 25:343-348.
4. Grandvaux, N., B. R. tenOever, M. J. Servant, and J. Hiscott. 2002. The interferon antiviral response: from viral invasion to evasion. *Current opinion in infectious diseases* 15:259-267.
5. Seet, B. T., J. B. Johnston, C. R. Brunetti, J. W. Barrett, H. Everett, C. Cameron, J. Sypula, S. H. Nazarian, A. Lucas, and G. McFadden. 2003. Poxviruses and immune evasion. *Annu Rev Immunol* 21:377-423.
6. Theofilopoulos, A. N., R. Baccala, B. Beutler, and D. H. Kono. 2005. Type I interferons (alpha/beta) in immunity and autoimmunity. *Annu Rev Immunol* 23:307-336.
7. Smith, V. P., and A. Alcami. 2002. Inhibition of Interferons by Ectromelia Virus. *J. Virol.* 76:1124-1134.
8. Symons, J. A., A. Alcami, and G. L. Smith. 1995. Vaccinia virus encodes a soluble type I interferon receptor of novel structure and broad species specificity. *Cell* 81:551-560.
9. Alcami, A., J. A. Symons, and G. L. Smith. 2000. The vaccinia virus soluble alpha/beta interferon (IFN) receptor binds to the cell surface and protects cells from the antiviral effects of IFN. *J Virol* 74:11230-11239.
10. Colamonici, O. R., P. Domanski, S. M. Sweitzer, A. Larner, and R. M. Buller. 1995. Vaccinia virus B18R gene encodes a type I interferon-binding protein that blocks interferon alpha transmembrane signaling. *J Biol Chem* 270:15974-15978.
11. Chen, N., M. I. Danila, Z. Feng, R. M. Buller, C. Wang, X. Han, E. J. Lefkowitz, and C. Upton. 2003. The genomic sequence of ectromelia virus, the causative agent of mousepox. *Virology* 317:165-186.

12. Fang, M., H. Cheng, Z. Dai, Z. Bu, and L. J. Sigal. 2006. Immunization with a single extracellular enveloped virus protein produced in bacteria provides partial protection from a lethal orthopoxvirus infection in a natural host. *Virology* 345:231-243.

13. Fang, M., and L. J. Sigal. 2005. Antibodies and CD8+ T Cells Are Complementary and Essential for Natural Resistance to a Highly Lethal Cytopathic Virus. *J Immunol* 175:6829-6836.

14. Fang, M., and L. J. Sigal. 2006. Direct CD28 Costimulation is Required for CD8+ T Cell-Mediated Resistance to an Acute Viral Disease in a Natural Host. *J Immunol* 177:8027-8036.

15. Xu, R.-H., M. Fang, A. Klein-Szanto, and L. J. Sigal. 2007. Memory CD8+ T cells are gatekeepers of the lymph node draining the site of viral infection. *Proc Natl Acad Sci USA* 104:10992-10997.

16. Todaro, G. J., and H. Green. 1963. Quantitative studies of the growth of mouse embryo cells in culture and their development into established lines. *J Cell Biol* 17:299-313.

17. Johnston, J. B., and G. McFadden. 2004. Technical knockout: understanding poxvirus pathogenesis by selectively deleting viral immunomodulatory genes. *Cell Microbiol* 6:695-705.

18. Fenner, F. 1949. Mouse-pox; infectious ectromelia of mice; a review. *J Immunol* 63:341-373.

19. Esteban, D. J., and R. M. Buller. 2005. Ectromelia virus: the causative agent of mousepox. *J Gen Virol* 86:2645-2659.

20. Fenner, F. 1994. Mousepox (ectromelia). In Virus infections of rodents and lagomorphs. A. Osterhaus, editor Elsevier Science, Amsterdam; New York. 412.

21. Fenner, F., D. A. Henderson, I. Arita, Z. Jezek, D. Ladnyi, and W. H. Organization. 1988. Smallpox and its eradication. World Health Organization, Geneva. 1460 pp.

22. Blanden, R. V. 1971. Mechanisms of recovery from a generalized viral infection: mousepox. II. Passive transfer of recovery mechanisms with immune lymphoid cells. *J Exp Med* 133:1074-1089.

23. Buller, R. M., K. L. Holmes, A. Hugin, T. N. Frederickson, and H. C. Morse, 3rd. 1987. Induction of cytotoxic T-cell responses in vivo in the absence of CD4 helper cells. *Nature* 328:77-79.

24. Karupiah, G., R. M. Buller, N. Van Rooijen, C. J. Duarte, and J. Chen. 1996. Different roles for CD4+ and CD8+ T lymphocytes and macrophage subsets in the control of a generalized virus infection. *J Virol* 70:8301-8309.

25. Parker, A. K., S. Parker, W. M. Yokoyama, J. A. Corbett, and R. M. Buller. 2007. Induction of natural killer cell responses by ectromelia virus controls infection. *J Virol* 81:4070-4079.

26. Davies, D. H., D. M. Molina, J. Wrammert, J. Miller, S. Hirst, Y. Mu, J. Pablo, B. Unal, R. Nakajima-Sasaki, X. Liang, S. Crotty, K. L. Karem, I. K. Damon, R. Ahmed, L. Villarreal, and P. L. Felgner. 2007. Proteome-wide analysis of the serological response to vaccinia and smallpox. *Proteomics* 7:1678-1686.

27. Putz, M. M., C. M. Midgley, M. Law, and G. L. Smith. 2006. Quantification of antibody responses against multiple antigens of the two infectious forms of Vaccinia virus provides a benchmark for smallpox vaccination. *Nat Med* 12:1310-1315.

28. Sakala, I. G., G. Chaudhri, R. M. Buller, A. A. Nuara, H. Bai, N. Chen, and G. Karupiah. 2007. Poxvirus-encoded gamma interferon binding protein dampens the host immune response to infection. *Journal of virology* 81:3346-3353.

29. Hooper, J. W., D. M. Custer, C. S. Schmaljohn, and A. L. Schmaljohn. 2000. DNA vaccination with vaccinia virus L1R and A33R genes protects mice against a lethal poxvirus challenge. *Virology* 266:329-339.

30. Hooper, J. W., D. M. Custer, and E. Thompson. 2003. Four-gene-combination DNA vaccine protects mice against a lethal vaccinia virus challenge and elicits appropriate antibody responses in nonhuman primates. *Virology* 306:181-195.

31. Hooper, J. W., E. Thompson, C. Wilhelmsen, M. Zimmerman, M. A. Ichou, S. E. Steffen, C. S. Schmaljohn, A. L. Schmaljohn, and P. B. Jahrling. 2004. Smallpox DNA Vaccine Protects Nonhuman Primates against Lethal Monkeypox. *J Virol* 78:4433-4443.

32. Snyder, J. T., I. M. Belyakov, A. Dzutsev, F. Lemonnier, and J. A. Berzofsky. 2004. Protection against lethal vaccinia virus challenge in HLA-A2 transgenic mice by immunization with a single CD8+ T-cell peptide epitope of vaccinia and variola viruses. *J Virol* 78:7052-7060.

33. Fogg, C., S. Lustig, J. C. Whitbeck, R. J. Eisenberg, G. H. Cohen, and B. Moss. 2004. Protective immunity to vaccinia virus induced by vaccination with multiple recombinant outer membrane proteins of intracellular and extracellular virions. *J Virol* 78:10230-10237.

34. Fulginiti, V. A., A. Papier, J. M. Lane, J. M. Neff, and D. A. Henderson. 2003. Smallpox vaccination: a review, part II. Adverse events. *Clin Infect Dis* 37:251-271.

35. Edghill-Smith, Y., H. Golding, J. Manischewitz, L. R. King, D. Scott, M. Bray, A. Nalca, J. W. Hooper, C. A. Whitehouse, J. E. Schmitz, K. A. Reimann, and G. Franchini. 2005. Smallpox vaccine-induced antibodies are necessary and sufficient for protection against monkeypox virus. *Nat Med*

36. Earl, P. L., J. L. Americo, L. S. Wyatt, L. A. Eller, J. C. Whitbeck, G. H. Cohen, R. J. Eisenberg, C. J. Hartmann, D. L. Jackson, D. A. Kulesh, M. J. Martinez, D. M. Miller, E. M. Mucker, J. D. Shamblin, S. H. Zwiers, J. W. Huggins, P. B. Jahrling, and B. Moss. 2004. Immunogenicity of a highly attenuated MVA smallpox vaccine and protection against monkeypox. *Nature* 428:182-185.

37. Galmiche, M. C., J. Goenaga, R. Wittek, and L. Rindisbacher. 1999. Neutralizing and protective antibodies directed against vaccinia virus envelope antigens. *Virology* 254:71-80.

EXAMPLE II

While infection with mouse pox is exemplified in Example I, the compositions and methods described therein may be adapted for the treatment and prevention of other pox virus infections.

For example, humans could be immunized against small pox using a similar approach. The PBR Gene Record for the Variola virus strain Bangladesh 1974 (nur islam) is listed under VARV-BGD74_nur:glycoprotein. The targeted protein binds type-I interferons; similar to VACV-WR-200 and VACV-COP-B19R; which are immunoglobulin superfamily secreted proteins and host defense modulators. The amino acid sequence for the SPVP of this strain of small pox is provided at GenBank accession number: ABF23761. The availability of the sequence information for this protein facilitates the recombinant production and purification of large quantities thereof. SPVP antigens may be produced using any number of recombinant expression systems. The protein may be produced in E. coli, yeast, insect or mammalian cells using suitable expression vectors well known to the skilled artisan. Once the protein is purified, it may be used to immunize patients via subcutaneous injection of sufficient quantities in a biological carrier to generate a protective immune response via active immunization. Booster injections may also be administered as needed.

Alternatively, humanized monoclonal antibodies to the smallpox SPVP could be generated either via immunization of the XENOMOUSE® with the small pox SPVP or genetic engineering of the antigen binding regions on to a humanized antibody framework after production in a suitable host animal. Once the humanized antibodies are produced, suitable quantities may be passively administered to a human patient to treat and/or prevent small pox infection. Thus, humanized monoclonal antibodies to the SPVP listed herein or functional fragments thereof are also encompassed by the present invention.

Other preferred SPVP proteins from small pox and their GenBank accession numbers are listed below. The skilled person can readily adapt the protocols described above to generate a protective immune response to the SPVP listed.

PBR Gene Record for: VARV-BGD74_nur:CC-chemokine-binding protein
Virus: Variola virus strain Bangladesh 1974 (nur islam)
Protein function: similar to VACV-WR-218; VACV-COP-C23L:B29R; host defense modulator
GenBank accession number: ABF23769

PBR Gene Record for: VARV-BGD74_nur:Crm-B secreted TNF-alpha-receptor-like protein
Virus: Variola virus strain Bangladesh 1974 (nur islam)
Protein function: similar to VACV-WR-215; host defense modulator
GenBank accession number: ABF23768

PBR Gene Record for: VARV-BGD74_nur:IL-1-beta-inhibitor
Virus: Variola virus strain Bangladesh 1974 (nur islam)
Protein function: similar to part of VACV-WR-197; part of VACV-COP-B16R; host defense modulator
GenBank accession number: ABF23758

PBR Gene Record for: VARV-BGD74_nur:interferon-gamma receptor-like soluble protein
Virus: Variola virus strain Bangladesh 1974 (nur islam)
Protein function: similar to VACV-WR-190; VACV-COP-B8R; host defense modulator
GenBank accession number: ABF23752

It may also be desirable to actively or passively immunize a human patient against monkeypox. Suitable SPVP from monkeypox and their GenBank Accession numbers are provided below. As with the SPVP from smallpox, the SPVP from monkey pox can be employed in the methods described above to generate a robust immune response against this particular virus.

PBR Gene Record for: MPXV-USA_2003_039:192
Virus: Monkeypox virus strain USA_2003_039
Protein function: IFN-alpha-beta-receptor-like secreted glycoprotein
GenBank accession number: AAY97783

PBR Gene Record for: MPXV-USA_2003_039:001
Virus: Monkeypox virus strain USA_2003_039
Protein function: chemokine-binding protein
GenBank accession number: AAY97599

PBR Gene Record for: MPXV-USA_2003_039:002
Virus: Monkeypox virus strain USA_2003_039
Protein function: TNF-alpha-receptor-like protein
GenBank accession number: AAY97600

PBR Gene Record for: MPXV-USA_2003_039:189
Virus: Monkeypox virus strain USA_2003_039
Protein function: bifunctional IL-1-beta-inhibitor-prevents febrile response in VAC-mouse intranasal model
GenBank accession number: AAY97780

PBR Gene Record for: MPXV-USA_2003_039:183
Virus: Monkeypox virus strain USA_2003_039
Protein function: soluble interferon-gamma receptor-like protein
GenBank accession number: AAY97774

As discussed at length hereinabove, there are many different pox viruses which cause disease in both human and animal populations. Tables I-XI provide additional SPVP targets and the virus species and gene name for developing anti-pox vaccines against the cognate virus. Each of the SPVP listed can be utilized to stimulate an immune response and thereby treat or prevent invention with the cognate virus.

TABLE I

Viral Orthologous Clusters V2.0
(VOCs)
C-type lectins
Gene Results Table

| Genome name | Genus | Genome id | Ortholog Group Name | Ortholog Group ID | Gene number | Gene id | Genbank id | Genbank name |
|---|---|---|---|---|---|---|---|---|
| Bovine papular stomatitis virus strain BV-AR02 | Parapoxvirus | 1505 | C-type lectin-like EEV protein (Cop-A34R) | 374 | BPSV-AR02-110 | 43450 | 41018862 | 109 |
| Camelpox virus strain CMS | Orthopoxvirus | 1493 | C-type lectin-like EEV protein (Cop-A34R) | 374 | CMLV-CMS-194 | 41290 | 19718122 | 151R |
| Camelpox virus strain M96 | Orthopoxvirus | 1491 | C-type lectin-like EEV protein (Cop-A34R) | 374 | CMLV-M96-155 | 40861 | 18640387 | 153 |
| Canarypox virus strain ATCC VR111 | Avipoxvirus | 1506 | C-type lectin-like EEV protein (Cop-A34R) | 374 | CNPV-VR111-272 | 43745 | 40556210 | 272 |
| Cowpox virus strain Brighton Red | Orthopoxvirus | 1496 | C-type lectin-like EEV protein (Cop-A34R) | 374 | CPXV-BR-175 | 41874 | 20178532 | 169 |
| Cowpox virus strain GRI-90 | Orthopoxvirus | 1501 | C-type lectin-like EEV protein (Cop-A34R) | 374 | CPXV-GRI-159 | 42816 | 3051927 | A35R |
| Cowpox virus strain Germany 91-3 | Orthopoxvirus | 2214 | C-type lectin-like EEV protein (Cop-A34R) | 374 | CPXV-GER91-158 | 56533 | 90660391 | IEV and EEV outer membrane lectin-like glycoprotein 133 |
| Deepox virus strain W-1170-84 | Unclassified | 1516 | C-type lectin-like EEV protein (Cop-A34R) | 374 | DPV-W1170_84-131 | 45414 | 0 | 133 |
| Deepox virus strain W-848-83 | Unclassified | 1515 | C-type lectin-like EEV protein (Cop-A34R) | 374 | DPV-W848_83-131 | 45244 | 62637510 | 133 |
| Ectromelia virus strain Moscow | Orthopoxvirus | 1492 | C-type lectin-like EEV protein (Cop-A34R) | 374 | ECTV-Mos-140 | 41059 | 22164742 | 136 |
| Ectromelia virus strain Naval | Orthopoxvirus | 1499 | C-type lectin-like EEV protein (Cop-A34R) | 374 | ECTV-Nav-143 | 42398 | 0 | 156 |
| Fowlpox virus strain HP1-438 Munich | Avipoxvirus | 1509 | C-type lectin-like EEV protein (Cop-A34R) | 374 | FWPV-HP1_438-190 | 44263 | 41023482 | fp9.198 |
| Fowlpox virus strain Iowa | Avipoxvirus | 1476 | C-type lectin-like EEV protein (Cop-A34R) | 374 | FWPV-Iowa-200 | 37932 | 9634868 | 198 |
| Goatpox virus strain G20-LKV | Capripoxvirus | 1514 | C-type lectin-like EEV protein (Cop-A34R) | 374 | GTPV-G20LKV-122 | 45082 | 0 | 118 |
| Goatpox virus strain Pellor | Capripoxvirus | 1513 | C-type lectin-like EEV protein (Cop-A34R) | 374 | GTPV-Pellor-121 | 44931 | 0 | 118 |
| Horsepox virus strain MNR-76 | Orthopoxvirus | 2230 | C-type lectin-like EEV protein (Cop-A34R) | 374 | HSPV-MNR76-177 | 59814 | 111184344 | HSPV155 |
| Lumpy skin disease virus strain Neethling 2490 | Capripoxvirus | 1488 | C-type lectin-like EEV protein (Cop-A34R) | 374 | LSDV-Nee-125 | 40328 | 15150562 | 123 |
| Lumpy skin disease virus strain Neethling Warmbaths LW | Capripoxvirus | 1497 | C-type lectin-like EEV protein (Cop-A34R) | 374 | LSDV-NW_LW-127 | 42061 | 22595658 | 123 |
| Lumpy skin disease virus strain Neethling vaccine LW 1959 | Capripoxvirus | 1498 | C-type lectin-like EEV protein (Cop-A34R) | 374 | LSDV-LW1959-126 | 42220 | 22595816 | 123 |
| Molluscum contagiosum virus strain subtype 1 | Molluscipoxvirus | 1477 | C-type lectin-like EEV protein (Cop-A34R) | 374 | MOCV-st1-144 | 38138 | 9629075 | 143R |
| Monkeypox Virus strain Walter Reed 267 | Orthopoxvirus | 1502 | C-type lectin-like EEV protein (Cop-A34R) | 374 | MPXV-WR267-141 | 43012 | 0 | 140 |

TABLE 1-continued

Viral Orthologous Clusters V2.0
(VOCs)
C-type lectins
Gene Results Table

| Genome name | Genus | Genome id | Ortholog Group Name | Ortholog Group ID | Gene number | Gene id | Genbank id | Genbank name |
|---|---|---|---|---|---|---|---|---|
| Monkeypox virus strain COP-58 | Orthopoxvirus | 1520 | C-type lectin-like EEV protein (Cop-A34R) | 374 | MPXV-COP58-140 | 46445 | 59858946 | 140 |
| Monkeypox virus strain Congo_2003_358 | Orthopoxvirus | 1524 | C-type lectin-like EEV protein (Cop-A34R) | 374 | MPXV-COG_2003_358- | 47209 | 68449026 | 154 |
| Monkeypox virus strain Liberia_1970_184 | Orthopoxvirus | 1525 | C-type lectin-like EEV protein (Cop-A34R) | 374 | MPXV-LBR_1970_184-1 | 47406 | 68449427 | 154 |
| Monkeypox virus strain Sierra Leone | Orthopoxvirus | 1521 | C-type lectin-like EEV protein (Cop-A34R) | 374 | MPXV-SLE-140 | 46622 | 58220610 | 140 |
| Monkeypox virus strain USA_2003_039 | Orthopoxvirus | 1526 | C-type lectin-like EEV protein (Cop-A34R) | 374 | MPXV-USA_2003_039- | 47605 | 68449627 | 154 |
| Monkeypox virus strain USA_2003_044 | Orthopoxvirus | 1522 | C-type lectin-like EEV protein (Cop-A34R) | 374 | MPXV-USA_2003_044- | 46807 | 68448825 | 154 |
| Monkeypox virus strain Zaire | Orthopoxvirus | 1489 | C-type lectin-like EEV protein (Cop-A34R) | 374 | MPXV-ZAR-149 | 40510 | 17975059 | A36R |
| Monkeypox virus strain Zaire_1979_005 | Orthopoxvirus | 1523 | C-type lectin-like EEV protein (Cop-A34R) | 374 | MPXV-ZAR_1979_005- | 47008 | 68449228 | 154 |
| Myxoma virus strain Lausanne | Leporipoxvirus | 1479 | C-type lectin-like EEV protein (Cop-A34R) | 374 | MYXV-Lau-127 | 38551 | 9633758 | m122R |
| Orf virus strain NZ2 | Parapoxvirus | 1527 | C-type lectin-like EEV protein (Cop-A34R) | 374 | ORFV-NZ2-109 | 47764 | 74230823 | 110 |
| Orf virus strain NZ2 Patent WO03006654 | Parapoxvirus | 1504 | C-type lectin-like EEV protein (Cop-A34R) | 374 | ORFV-NZ2_Pat-115 | 43304 | 32167504 | 112 |
| Orf virus strain OV-IA82 | Parapoxvirus | 1507 | C-type lectin-like EEV protein (Cop-A34R) | 374 | ORFV-IA82-110 | 43911 | 41018597 | 107 |
| Orf virus strain OV-SA00 | Parapoxvirus | 1508 | C-type lectin-like EEV protein (Cop-A34R) | 374 | ORFV-SA00-110 | 44047 | 41018730 | 107 |
| Rabbit fibroma virus strain Kasza | Leporipoxvirus | 1480 | C-type lectin-like EEV protein (Cop-A34R) | 374 | SFV-Kas-127 | 38722 | 9633932 | gp122R |
| Rabbitpox virus strain Utrecht | Orthopoxvirus | 1494 | C-type lectin-like EEV protein (Cop-A34R) | 374 | RPXV-Utr-144 | 41506 | 44971505 | 142 |
| Sheeppox virus strain A | Capripoxvirus | 1511 | C-type lectin-like EEV protein (Cop-A34R) | 374 | SPPV-A-121 | 44630 | 0 | 118 |
| Sheeppox virus strain NISKHI | Capripoxvirus | 1512 | C-type lectin-like EEV protein (Cop-A34R) | 374 | SPPV-NISKHI-120 | 44779 | 0 | 118 |
| Sheeppox virus strain TU-V02127 | Capripoxvirus | 1495 | C-type lectin-like EEV protein (Cop-A34R) | 374 | SPPV-TU-121 | 41669 | 21492575 | 118 |
| Swinepox virus strain Nebraska 17077-99 | Suipoxvirus | 1490 | C-type lectin-like EEV protein (Cop-A34R) | 374 | SWPV-Neb-121 | 40676 | 18640206 | 120 |
| Tanapox virus strain Kenya | Yatapoxvirus | 3496 | C-type lectin-like EEV protein (Cop-A34R) | 374 | TANV-KEN-128 | 67634 | 146746463 | 123R |
| Tanapox virus isolate TPV-RoC | Yatapoxvirus | 3497 | C-type lectin-like EEV protein (Cop-A34R) | 374 | TANV-COD-127 | 67739 | 146746619 | 123R |
| Taterapox virus strain Dahomey 1968 | Orthopoxvirus | 2195 | C-type lectin-like EEV protein (Cop-A34R) | 374 | TATV-DAH68-158 | 53076 | 113195335 | IEV and EEV outer membrane lectin-like glycoprotein |

TABLE 1-continued

Viral Orthologous Clusters V2.0
(VOCs)
C-type lectins
Gene Results Table

| Genome name | Genus | Genome id | Ortholog Group Name | Ortholog Group ID | Gene number | Gene id | Genbank id | Genbank name |
|---|---|---|---|---|---|---|---|---|
| Vaccinia virus strain 3737 | Orthopoxvirus | 1528 | C-type lectin-like EEV protein (Cop-A34R) | 374 | VACV-3737-159 | 47947 | 88900775 | 153 |
| Vaccinia virus strain Acambis 2000 | Orthopoxvirus | 2161 | C-type lectin-like EEV protein (Cop-A34R) | 374 | VACV-Acam2000-166 | 51222 | 38349024 | 168 |
| Vaccinia virus strain Acambis 3 | Orthopoxvirus | 2162 | C-type lectin-like EEV protein (Cop-A34R) | 374 | VACV-Acam3-168 | 51459 | 37551602 | 168 |
| Vaccinia virus strain Acambis 3000 Modified Virus Ankara | Orthopoxvirus | 1510 | C-type lectin-like EEV protein (Cop-A34R) | 374 | VACV-Acam3000-149 | 44463 | 47088473 | 147 |
| Vaccinia virus strain Copenhagen | Orthopoxvirus | 1485 | C-type lectin-like EEV protein (Cop-A34R) | 374 | VACV-Cop-197 | 39722 | 335509 | A34R |
| Vaccinia virus strain DUKE | Orthopoxvirus | 2458 | C-type lectin-like EEV protein (Cop-A34R) | 374 | VACV-DUKE-165 | 63545 | 90819817 | 165 |
| Vaccinia virus strain LC16m8 | Orthopoxvirus | 1517 | C-type lectin-like EEV protein (Cop-A34R) | 374 | VACV-LC16m8-211 | 45664 | 56713550 | m8201R |
| Vaccinia virus strain LC16mO | Orthopoxvirus | 1518 | C-type lectin-like EEV protein (Cop-A34R) | 374 | VACV-LC16mO-211 | 45948 | 56713834 | mO201R |
| Vaccinia virus strain Lister | Orthopoxvirus | 1519 | C-type lectin-like EEV protein (Cop-A34R) | 374 | VACV-Lister-211 | 46232 | 0 | m8201R |
| Vaccinia virus strain Lister_VACV107 | Orthopoxvirus | 2659 | C-type lectin-like EEV protein (Cop-A34R) | 374 | VACV-Lister_VACV107- | 64487 | 88854227 | List150 |
| Vaccinia virus strain MVA-I721 | Orthopoxvirus | 2696 | C-type lectin-like EEV protein (Cop-A34R) | 374 | VACV-MVA_I721-132 | 65345 | 0 | 147 |
| Vaccinia virus strain Western Reserve | Orthopoxvirus | 1500 | C-type lectin-like EEV protein (Cop-A34R) | 374 | VACV-WR-157 | 42596 | 66275954 | 157 |
| Vaccinia virus strain modified vaccinia Ankara | Orthopoxvirus | 1484 | C-type lectin-like EEV protein (Cop-A34R) | 374 | VACV-MVA-129 | 65541 | 2772790 | MVA145R |
| Variola major virus strain Bangladesh 1975 | Orthopoxvirus | 1481 | C-type lectin-like EEV protein (Cop-A34R) | 374 | VARV-BGD75maj-147 | 38908 | 439058 | A37R |
| Variola minor virus strain Garcia 1966 | Orthopoxvirus | 1482 | C-type lectin-like EEV protein (Cop-A34R) | 374 | VARV-Gar_1966-150 | 39103 | 5830702 | A38R |
| Variola virus strain Afghanistan 1970 Variolator 4 | Orthopoxvirus | 2197 | C-type lectin-like EEV protein (Cop-A34R) | 374 | VARV-AFG70-146 | 53490 | 109724185 | glycoprotein |
| Variola virus strain Bangladesh 1974 (Shahzaman) | Orthopoxvirus | 2216 | C-type lectin-like EEV protein (Cop-A34R) | 374 | VARV-BGD74_shz-146 | 56938 | 94484803 | glycoprotein |
| Variola virus strain Bangladesh 1974 (Solaiman) | Orthopoxvirus | 2217 | C-type lectin-like EEV protein (Cop-A34R) | 374 | VARV-BGD74_sol-146 | 57136 | 94485001 | glycoprotein |
| Variola virus strain Bangladesh 1974 (nur islam) | Orthopoxvirus | 2215 | C-type lectin-like EEV protein (Cop-A34R) | 374 | VARV-BGD74_nur-146 | 56740 | 94484605 | glycoprotein |
| Variola virus strain Bangladesh 1975 v75-550 Banu | Orthopoxvirus | 2198 | C-type lectin-like EEV protein (Cop-A34R) | 374 | VARV-BGD75_Banu-14 | 53693 | 109724389 | glycoprotein |
| Variola virus strain Benin, Dahomey 1968 (v68-59) | Orthopoxvirus | 2224 | C-type lectin-like EEV protein (Cop-A34R) | 374 | VARV-BEN68-148 | 58558 | 94483788 | glycoprotein |
| Variola virus strain Botswana 1972 (v72-143) | Orthopoxvirus | 2225 | C-type lectin-like EEV protein (Cop-A34R) | 374 | VARV-BWA72-146 | 58765 | 94483993 | glycoprotein |
| Variola virus strain Botswana 1973 (v73-225) | Orthopoxvirus | 2226 | C-type lectin-like EEV protein (Cop-A34R) | 374 | VARV-BWA73-146 | 58967 | 94484196 | glycoprotein |

TABLE 1-continued

Viral Orthologous Clusters V2.0
(VOCs)
C-type lectins
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Brazil 1966 (v66-39 Sao Paulo) | Orthopoxvirus | 2227 | C-type lectin-like EEV protein (Cop-A34R) | 374 | VARV-BRA66-150 | 59173 | 94484401 | glycoprotein |
| Variola virus strain China Horn 1948 Sabin Lab July 1948 | Orthopoxvirus | 2203 | C-type lectin-like EEV protein (Cop-A34R) | 374 | VARV-CHN48-146 | 54306 | 109724591 | glycoprotein |
| Variola virus strain Congo 1970 v70-46 Kinshasa | Orthopoxvirus | 2229 | C-type lectin-like EEV protein (Cop-A34R) | 374 | VARV-COG70_46-146 | 59581 | 109724796 | glycoprotein |
| Variola virus strain Congo 9 1970 (v74-227 Gispen) | Orthopoxvirus | 2228 | C-type lectin-like EEV protein (Cop-A34R) | 374 | VARV-COG70_227-146 | 59380 | 94485199 | glycoprotein |
| Variola virus strain Ethiopia 1972 (Eth16 R14-1X-72 Addis) | Orthopoxvirus | 2231 | C-type lectin-like EEV protein (Cop-A34R) | 374 | VARV-ETH72_16-147 | 60020 | 94485401 | glycoprotein |
| Variola virus strain Ethiopia 1972 (Eth17 R14-1X-72 Addis) | Orthopoxvirus | 2232 | C-type lectin-like EEV protein (Cop-A34R) | 374 | VARV-ETH72_17-147 | 60223 | 94485604 | glycoprotein |
| Variola virus strain Germany 1958 Heidelberg | Orthopoxvirus | 2233 | C-type lectin-like EEV protein (Cop-A34R) | 374 | VARV-DEU58-145 | 60422 | 109724999 | glycoprotein |
| Variola virus strain Guinea 1969 (005) | Orthopoxvirus | 2234 | C-type lectin-like EEV protein (Cop-A34R) | 374 | VARV-GIN69-148 | 60626 | 94485806 | glycoprotein |
| Variola virus strain India 1953 (Kali-Muthu-M50 Madras) | Orthopoxvirus | 2238 | C-type lectin-like EEV protein (Cop-A34R) | 374 | VARV-IND53_mad-146 | 61436 | 94486009 | glycoprotein |
| Variola virus strain India 1953 (New Delhi) | Orthopoxvirus | 2239 | C-type lectin-like EEV protein (Cop-A34R) | 374 | VARV-IND53_ndel-145 | 61636 | 94486210 | glycoprotein |
| Variola virus strain India 1964 7124 Vellore | Orthopoxvirus | 2240 | C-type lectin-like EEV protein (Cop-A34R) | 374 | VARV-IND64_vel4-147 | 61840 | 109725203 | glycoprotein |
| Variola virus strain India 1964 7125 Vellore | Orthopoxvirus | 2241 | C-type lectin-like EEV protein (Cop-A34R) | 374 | VARV-IND64_vel5-146 | 62044 | 109725408 | IEV and EEV outer membrane lectin-like glycoprotein A37R |
| Variola virus strain India 3 Major 1967 | Orthopoxvirus | 1483 | C-type lectin-like EEV protein (Cop-A34R) | 374 | VARV-IND3_1967-144 | 39306 | 9627662 | A37R |
| Variola virus strain Iran 1972 2602 Tabriz | Orthopoxvirus | 2235 | C-type lectin-like EEV protein (Cop-A34R) | 374 | VARV-IRN72-146 | 60831 | 109725611 | glycoprotein |
| Variola virus strain Japan 1946 (Yamada MS-2(A) Tokyo) | Orthopoxvirus | 2243 | C-type lectin-like EEV protein (Cop-A34R) | 374 | VARV-JPN46_yam-145 | 62420 | 94486413 | glycoprotein |
| Variola virus strain Japan 1951 (Harper, Masterseed) | Orthopoxvirus | 2244 | C-type lectin-like EEV protein (Cop-A34R) | 374 | VARV-JPN51_hrpr-145 | 62622 | 94486616 | glycoprotein |
| Variola virus strain Japan 1951 (Stillwell, Masterseed) | Orthopoxvirus | 2245 | C-type lectin-like EEV protein (Cop-A34R) | 374 | VARV-JPN51_stwl-145 | 62823 | 94486818 | glycoprotein |
| Variola virus strain Korea 1947 (Lee, Masterseed) | Orthopoxvirus | 2236 | C-type lectin-like EEV protein (Cop-A34R) | 374 | VARV-KOR47-146 | 61034 | 94487021 | glycoprotein |
| Variola virus strain Kuwait 1967 (K1629) | Orthopoxvirus | 2237 | C-type lectin-like EEV protein (Cop-A34R) | 374 | VARV-KWT67-146 | 61236 | 94487224 | glycoprotein |
| Variola virus strain Nepal 1973 V73-175 | Orthopoxvirus | 2221 | C-type lectin-like EEV protein (Cop-A34R) | 374 | VARV-NPL73-146 | 57936 | 109725815 | glycoprotein |
| Variola virus strain Niger 1969 (001, importation from Nigeria) | Orthopoxvirus | 2222 | C-type lectin-like EEV protein (Cop-A34R) | 374 | VARV-NER69-149 | 58142 | 94487426 | glycoprotein |
| Variola virus strain Sierra Leone 1969 (V68-258) | Orthopoxvirus | 2223 | C-type lectin-like EEV protein (Cop-A34R) | 374 | VARV-SLE68-149 | 58351 | 94488035 | glycoprotein |

TABLE 1-continued

Viral Orthologous Clusters V2.0
(VOCs)
C-type lectins
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Somalia 1977 (V77-1252) | Orthopoxvirus | 2218 | C-type lectin-like EEV protein (Cop-A34R) | 374 | VARV-SOM77_1252-14 | 57334 | 94488238 | glycoprotein |
| Variola virus strain Somalia 1977 (V77-1605) | Orthopoxvirus | 2219 | C-type lectin-like EEV protein (Cop-A34R) | 374 | VARV-SOM77_1605-14 | 57534 | 94488438 | glycoprotein |
| Variola virus strain Somalia 1977 V77-2479 | Orthopoxvirus | 2220 | C-type lectin-like EEV protein (Cop-A34R) | 374 | VARV-SOM77_ali-146 | 57734 | 109726222 | glycoprotein |
| Variola virus strain South Africa 1965 (102 Natal, Ingwavuma) | Orthopoxvirus | 2210 | C-type lectin-like EEV protein (Cop-A34R) | 374 | VARV-ZAF65_102-146 | 55718 | 94487630 | glycoprotein |
| Variola virus strain South Africa 1965 (103 Tvaal, Nelspruit) | Orthopoxvirus | 2211 | C-type lectin-like EEV protein (Cop-A34R) | 374 | VARV-ZAF65_103-146 | 55919 | 94487831 | glycoprotein |
| Variola virus strain Sudan 1947 (Juba) | Orthopoxvirus | 2212 | C-type lectin-like EEV protein (Cop-A34R) | 374 | VARV-SDN47_jub-146 | 56120 | 94488638 | IEV and EEV outer membrane lectin-like glycoprotein |
| Variola virus strain Sudan 1947 (Rumbec) | Orthopoxvirus | 2213 | C-type lectin-like EEV protein (Cop-A34R) | 374 | VARV-SDN47_rum-146 | 56320 | 94488839 | glycoprotein |
| Variola virus strain Sumatra 1970 V70-222 | Orthopoxvirus | 2208 | C-type lectin-like EEV protein (Cop-A34R) | 374 | VARV-SUM70_222-145 | 55315 | 109726424 | glycoprotein |
| Variola virus strain Sumatra 1970 V70-228 | Orthopoxvirus | 2209 | C-type lectin-like EEV protein (Cop-A34R) | 374 | VARV-SUM70_228-145 | 55517 | 94489039 | glycoprotein |
| Variola virus strain Syria 1972 V72-199 | Orthopoxvirus | 2206 | C-type lectin-like EEV protein (Cop-A34R) | 374 | VARV-SYR72-146 | 54912 | 109726628 | glycoprotein |
| Variola virus strain Tanzania 1965 kembula | Orthopoxvirus | 2207 | C-type lectin-like EEV protein (Cop-A34R) | 374 | VARV-TZA65-146 | 55115 | 94489239 | glycoprotein |
| Variola virus strain United Kingdom 1946 Harvey | Orthopoxvirus | 2204 | C-type lectin-like EEV protein (Cop-A34R) | 374 | VARV-GBR44_harv-146 | 54511 | 94489439 | glycoprotein |
| Variola virus strain United Kingdom 1946 Hinden (Middlesex) | Orthopoxvirus | 2205 | C-type lectin-like EEV protein (Cop-A34R) | 374 | VARV-GBR46_hind-145 | 54712 | 94489641 | glycoprotein |
| Variola virus strain United Kingdom 1947 Higgins (Staffordshire) | Orthopoxvirus | 2202 | C-type lectin-like EEV protein (Cop-A34R) | 374 | VARV-GBR47_hig-146 | 54105 | 94489841 | glycoprotein |
| Variola virus strain United Kingdom 1952 Butler | Orthopoxvirus | 2200 | C-type lectin-like EEV protein (Cop-A34R) | 374 | VARV-GBR52_but-150 | 53898 | 94490045 | glycoprotein |
| Variola virus strain Yugoslavia 1972 V72-164 | Orthopoxvirus | 2196 | C-type lectin-like EEV protein (Cop-A34R) | 374 | VARV-YUG72-146 | 53289 | 94490250 | glycoprotein |
| Yaba monkey tumor virus strain Amano | Yatapoxvirus | 1503 | C-type lectin-like EEV protein (Cop-A34R) | 374 | YMTV-Amano-117 | 43166 | 38229286 | 123R |
| Yaba-like Disease Virus strain Davis | Yatapoxvirus | 1487 | C-type lectin-like EEV protein (Cop-A34R) | 374 | YLDV-Davis-126 | 40175 | 12085106 | 123R |

TABLE 2

Viral Orthologous Clusters V2.0 (VOCs)
CD47-like
Gene Results Table

| Genome name | Genus | Genome id | Ortholog Group Name | Ortholog Group ID | Gene number | Gene id | Genbank id | Genbank name |
|---|---|---|---|---|---|---|---|---|
| Camelpox virus strain CMS | Orthopoxvirus | 1493 | CD47-like | 580 | CMLV-CMS-200 | 41296 | 19718128 | 155L |
| Camelpox virus strain M96 | Orthopoxvirus | 1491 | CD47-like | 580 | CMLV-M96-160 | 40866 | 18640392 | 158 |
| Cowpox virus strain Brighton Red | Orthopoxvirus | 1496 | CD47-like | 580 | CPXV-BR-181 | 41880 | 20178537 | 175 |
| Cowpox virus strain GRI-90 | Orthopoxvirus | 1501 | CD47-like | 580 | CPXV-GRI-164 | 42821 | 30519532 | A40L |
| Cowpox virus strain Germany 91-3 | Orthopoxvirus | 2214 | CD47-like | 580 | CPXV-GER91-163 | 56538 | 90660396 | CD47-like putative membrane protein |
| Deerpox virus strain W-1170-84 | Unclassified | 1516 | CD47-like | 580 | DPV-W1170_84-136 | 45419 | 0 | 139 |
| Deerpox virus strain W-848-83 | Unclassified | 1515 | CD47-like | 580 | DPV-W848_83-136 | 45249 | 62637516 | 139 |
| Ectromelia virus strain Moscow | Orthopoxvirus | 1492 | CD47-like | 580 | ECTV-Mos-143 | 41062 | 22164744 | 138 |
| Ectromelia virus strain Naval | Orthopoxvirus | 1499 | CD47-like | 580 | ECTV-Nav-146 | 42401 | 0 | 160 |
| Goatpox virus strain G20-LKV | Capripoxvirus | 1514 | CD47-like | 580 | GTPV-G20LKV-127 | 45087 | 0 | 123 |
| Goatpox virus strain Pellor | Capripoxvirus | 1513 | CD47-like | 580 | GTPV-Pellor-126 | 44936 | 0 | 123 |
| Horsepox virus strain MNR-76 | Orthopoxvirus | 2230 | CD47-like | 580 | HSPV-MNR76-182 | 59819 | 111184349 | HSPV160 |
| Lumpy skin disease virus strain Neethling 2490 | Capripoxvirus | 1488 | CD47-like | 580 | LSDV-Nee-130 | 40333 | 15150567 | 128 |
| Lumpy skin disease virus strain Neethling Warmbaths LW | Capripoxvirus | 1497 | CD47-like | 580 | LSDV-NW_LW-132 | 42066 | 22595663 | 128 |
| Lumpy skin disease virus strain Neethling vaccine LW 1959 | Capripoxvirus | 1498 | CD47-like | 580 | LSDV-LW1959-131 | 42225 | 22595821 | 128 |
| Monkeypox Virus strain Walter Reed 267 | Orthopoxvirus | 1502 | CD47-like | 580 | MPXV-WR267-145 | 43016 | 0 | 144 |
| Monkeypox virus strain COP-58 | Orthopoxvirus | 1520 | CD47-like | 580 | MPXV-COP58-144 | 46449 | 59858950 | 144 |
| Monkeypox virus strain Congo_2003_358 | Orthopoxvirus | 1524 | CD47-like | 580 | MPXV-COG_2003_358-155 | 47214 | 68449031 | 159 |
| Monkeypox virus strain Liberia_1970_184 | Orthopoxvirus | 1525 | CD47-like | 580 | MPXV-LBR_1970_184-152 | 47411 | 68449432 | 159 |
| Monkeypox virus strain Sierra Leone | Orthopoxvirus | 1521 | CD47-like | 580 | MPXV-SLE-144 | 46626 | 58220614 | 144 |
| Monkeypox virus strain USA_2003_039 | Orthopoxvirus | 1526 | CD47-like | 580 | MPXV-USA_2003_039-153 | 47610 | 68449632 | 159 |
| Monkeypox virus strain USA_2003_044 | Orthopoxvirus | 1522 | CD47-like | 580 | MPXV-USA_2003_044-153 | 46812 | 68448830 | 159 |
| Monkeypox virus strain Zaire | Orthopoxvirus | 1489 | CD47-like | 580 | MPXV-ZAR-153 | 40514 | 17975063 | A40L |
| Monkeypox virus strain Zaire_1979-005 | Orthopoxvirus | 1523 | CD47-like | 580 | MPXV-ZAR_1979_005-156 | 47013 | 68449233 | 159 |
| Myxoma virus strain Lausanne | Leporipoxvirus | 1479 | CD47-like | 580 | MYXV-Lau-133 | 38557 | 9633764 | m128L |
| Rabbit fibroma virus strain Kasza | Leporipoxvirus | 1480 | CD47-like | 580 | SFV-Kas-133 | 38728 | 9633938 | gp128L |
| Rabbitpox virus strain Utrecht | Orthopoxvirus | 1494 | CD47-like | 580 | RPXV-Utr-148 | 41510 | 44971509 | 146 |
| Sheeppox virus strain A | Capripoxvirus | 1511 | CD47-like | 580 | SPPV-A-126 | 44635 | 0 | 123 |
| Sheeppox virus strain NISKHI | Capripoxvirus | 1512 | CD47-like | 580 | SPPV-NISKHI-125 | 44784 | 0 | 123 |
| Sheeppox virus strain TU-V02127 | Capripoxvirus | 1495 | CD47-like | 580 | SPPV-TU-126 | 41674 | 21492580 | 123 |
| Swinepox virus strain Nebraska 17077-99 | Suipoxvirus | 1490 | CD47-like | 580 | SWPV-Neb-126 | 40681 | 18640211 | 125 |
| Tanapox virus strain Kenya | Yatapoxvirus | 3496 | CD47-like | 580 | TANV-KEN-133 | 67644 | 146746468 | 128L |
| Tanapox virus strain isolate TPV-RoC | Yatapoxvirus | 3497 | CD47-like | 580 | TANV-COD-132 | 67744 | 146746624 | 128L |
| Taterapox virus strain Dahomey 1968 | Orthopoxvirus | 2195 | CD47-like | 580 | TATV-DAH68-163 | 53081 | 113195340 | CCD47-like membrane protein |
| Vaccinia virus strain 3737 | Orthopoxvirus | 1528 | CD47-like | 580 | VACV-3737-164 | 47952 | 88900780 | 158 |
| Vaccinia virus strain Acambis 2000 | Orthopoxvirus | 2161 | CD47-like | 580 | VACV-Acam2000-171 | 51227 | 38349029 | 173 |
| Vaccinia virus strain Acambis 3 | Orthopoxvirus | 2162 | CD47-like | 580 | VACV-Acam3-173 | 51464 | 37551607 | 173 |

TABLE 2-continued

Viral Orthologous Clusters V2.0 (VOCs)
CD47-like
Gene Results Table

| Genome name | Genus | Genome id | Ortholog Group Name | Ortholog Group ID | Gene number | Gene id | Genbank id | Genbank name |
|---|---|---|---|---|---|---|---|---|
| Vaccinia virus strain Acambis 3000 Modified Virus Ankara | Orthopoxvirus | 1510 | CD47-like | 580 | VACV-Acam3000-153 | 44467 | 47088477 | 151 |
| Vaccinia virus strain Copenhagen | Orthopoxvirus | 1485 | CD47-like | 580 | VACV-Cop-204 | 39729 | 335516 | A38L |
| Vaccinia virus strain DUKE | Orthopoxvirus | 2458 | CD47-like | 580 | VACV-DUKE-170 | 63550 | 90819822 | 170 |
| Vaccinia virus strain LC16m8 | Orthopoxvirus | 1517 | CD47-like | 580 | VACV-LC16m8-218 | 45671 | 56713557 | m8208L |
| Vaccinia virus strain LC16mO | Orthopoxvirus | 1518 | CD47-like | 580 | VACV-LC16mO-218 | 45955 | 56713841 | mO208L |
| Vaccinia virus strain Lister | Orthopoxvirus | 1519 | CD47-like | 580 | VACV-Lister-218 | 46239 | 0 | m8208L |
| Vaccinia virus strain Lister_VACV107 | Orthopoxvirus | 2659 | CD47-like | 580 | VACV-Lister_VACV107-159 | 64492 | 88854235 | List155 |
| Vaccinia virus strain MVA-I721 | Orthopoxvirus | 2696 | CD47-like | 580 | VACV-MVA_I721-128 | 65341 | 0 | 151 |
| Vaccinia virus strain Western Reserve | Orthopoxvirus | 1500 | CD47-like | 580 | VACV-WR-162 | 42601 | 66275959 | 162 |
| Vaccinia virus strain modified vaccinia Ankara | Orthopoxvirus | 1484 | CD47-like | 580 | VACV-MVA-133 | 65545 | 2772738 | MVA149L |
| Variola major virus strain Bangladesh 1975 | Orthopoxvirus | 1481 | CD47-like | 580 | VARV-BGD75maj-151 | 38912 | 439062 | A41L |
| Variola minor virus strain Garcia 1966 | Orthopoxvirus | 1482 | CD47-like | 580 | VARV-Gar_1966-156 | 39109 | 5830708 | A44L |
| Variola virus strain Afghanistan 1970 Variolator 4 | Orthopoxvirus | 2197 | CD47-like | 580 | VARV-AFG70-152 | 53496 | 109724191 | membrane protein |
| Variola virus strain Bangladesh 1974 (Shahzaman) | Orthopoxvirus | 2216 | CD47-like | 580 | VARV-BGD74_shz-152 | 56944 | 94484809 | membrane protein |
| Variola virus strain Bangladesh 1974 (Solaiman) | Orthopoxvirus | 2217 | CD47-like | 580 | VARV-BGD74_sol-152 | 57142 | 94485007 | membrane protein |
| Variola virus strain Bangladesh 1974 (nur islam) | Orthopoxvirus | 2215 | CD47-like | 580 | VARV-BGD74_nur-152 | 56746 | 94484611 | membrane protein |
| Variola virus strain Bangladesh 1975 v75-550 Banu | Orthopoxvirus | 2198 | CD47-like | 580 | VARV-BGD75_Banu-152 | 53699 | 109724395 | membrane protein |
| Variola virus strain Benin, Dahomey 1968 (v68-59) | Orthopoxvirus | 2224 | CD47-like | 580 | VARV-BEN68-153 | 58563 | 94483793 | membrane protein |
| Variola virus strain Botswana 1972 (v72-143) | Orthopoxvirus | 2225 | CD47-like | 580 | VARV-BWA72-152 | 58771 | 94483999 | membrane protein |
| Variola virus strain Botswana 1973 (v73-225) | Orthopoxvirus | 2226 | CD47-like | 580 | VARV-BWA73-152 | 58973 | 94484202 | membrane protein |
| Variola virus strain Brazil 1966 (v66-39 Sao Paulo) | Orthopoxvirus | 2227 | CD47-like | 580 | VARV-BRA66-156 | 59179 | 94484407 | membrane protein |
| Variola virus strain China Horn 1948 Sabin Lab July 1948 | Orthopoxvirus | 2203 | CD47-like | 580 | VARV-CHN48-152 | 54312 | 109724597 | membrane protein |
| Variola virus strain Congo 1970 v70-46 Kinshasa | Orthopoxvirus | 2229 | CD47-like | 580 | VARV-COG70_46-152 | 59587 | 109724802 | membrane protein |
| Variola virus strain Congo 1970 (v74-227 Gispen) | Orthopoxvirus | 2228 | CD47-like | 580 | VARV-COG70_227-152 | 59386 | 94485205 | membrane protein |
| Variola virus strain Ethiopia 1972 (Eth16 R14-1X-72 Addis) | Orthopoxvirus | 2231 | CD47-like | 580 | VARV-ETH72_16-153 | 60026 | 94485407 | membrane protein |
| Variola virus strain Ethiopia 1972 (Eth17 R14-1X-72 Addis) | Orthopoxvirus | 2232 | CD47-like | 580 | VARV-ETH72_17-153 | 60229 | 94485610 | membrane protein |
| Variola virus strain Germany 1958 Heidelberg | Orthopoxvirus | 2233 | CD47-like | 580 | VARV-DEU58-151 | 60428 | 109725005 | membrane protein |
| Variola virus strain Guinea 1969 (005) | Orthopoxvirus | 2234 | CD47-like | 580 | VARV-GIN69-152 | 60630 | 94485810 | membrane protein |
| Variola virus strain India 1953 (Kali-Muthu-M50 Madras) | Orthopoxvirus | 2238 | CD47-like | 580 | VARV-IND53_mad-152 | 61442 | 94486015 | membrane protein |

TABLE 2-continued

Viral Orthologous Clusters V2.0 (VOCs)
CD47-like
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain India 1953 (New Delhi) | Orthopoxvirus | 2239 | CD47-like | 580 | VARV-IND53_ndel-151 | 61642 | 94486216 | membrane protein |
| Variola virus strain India 1964 7124 Vellore | Orthopoxvirus | 2240 | CD47-like | 580 | VARV-IND64_vel4-153 | 61846 | 109725209 | membrane protein |
| Variola virus strain India 1964 7125 Vellore | Orthopoxvirus | 2241 | CD47-like | 580 | VARV-IND64_vel5-152 | 62050 | 109725414 | CD47-like membrane protein |
| Variola virus strain India 3 Major 1967 | Orthopoxvirus | 1483 | CD47-like | 580 | VARV-IND3_1967-150 | 39312 | 9627668 | A41L |
| Variola virus strain Iran 1972 2602 Tabriz | Orthopoxvirus | 2235 | CD47-like | 580 | VARV-IRN72-152 | 60837 | 109725617 | membrane protein |
| Variola virus strain Japan 1946 (Yamada MS-2(A) Tokyo) | Orthopoxvirus | 2243 | CD47-like | 580 | VARV-JPN46_yam-151 | 62426 | 94486419 | membrane protein |
| Variola virus strain Japan 1951 (Harper, Masterseed) | Orthopoxvirus | 2244 | CD47-like | 580 | VARV-JPN51_hrpr-151 | 62628 | 94486622 | membrane protein |
| Variola virus strain Japan 1951 (Stillwell, Masterseed) | Orthopoxvirus | 2245 | CD47-like | 580 | VARV-JPN51_stwl-151 | 62829 | 94486824 | membrane protein |
| Variola virus strain Korea 1947 (Lee, Masterseed) | Orthopoxvirus | 2236 | CD47-like | 580 | VARV-KOR47-152 | 61040 | 94487027 | membrane protein |
| Variola virus strain Kuwait 1967 (K1629) | Orthopoxvirus | 2237 | CD47-like | 580 | VARV-KWT67-152 | 61242 | 94487230 | membrane protein |
| Variola virus strain Nepal 1973 V73-175 | Orthopoxvirus | 2221 | CD47-like | 580 | VARV-NPL73-152 | 57942 | 109725821 | membrane protein |
| Variola virus strain Niger 1969 (001, importation from Nigeria) | Orthopoxvirus | 2222 | CD47-like | 580 | VARV-NER69-154 | 58147 | 94487431 | membrane protein |
| Variola virus strain Sierra Leone 1969 (V68-258) | Orthopoxvirus | 2223 | CD47-like | 580 | VARV-SLE68-153 | 58355 | 94488039 | membrane protein |
| Variola virus strain Somalia 1977 (V77-1252) | Orthopoxvirus | 2218 | CD47-like | 580 | VARV-SOM77_1252-152 | 57340 | 94488244 | membrane protein |
| Variola virus strain Somalia 1977 (V77-1605) | Orthopoxvirus | 2219 | CD47-like | 580 | VARV-SOM77_1605-152 | 57540 | 94488444 | membrane protein |
| Variola virus strain Somalia 1977 V77-2479 | Orthopoxvirus | 2220 | CD47-like | 580 | VARV-SOM77_ali-152 | 57740 | 109726228 | membrane protein |
| Variola virus strain South Africa 1965 (102 Natal, Ingwavuma) | Orthopoxvirus | 2210 | CD47-like | 580 | VARV-ZAF65_102-152 | 55724 | 94487636 | membrane protein |
| Variola virus strain South Africa 1965 (103 Tvaal, Nelspruit) | Orthopoxvirus | 2211 | CD47-like | 580 | VARV-ZAF65_103-152 | 55925 | 94487837 | membrane protein |
| Variola virus strain Sudan 1947 (Juba) | Orthopoxvirus | 2212 | CD47-like | 580 | VARV-SDN47_jub-152 | 56126 | 94488644 | putative CD47-like membrane protein |
| Variola virus strain Sudan 1947 (Rumbec) | Orthopoxvirus | 2213 | CD47-like | 580 | VARV-SDN47_rum-152 | 56326 | 94488845 | membrane protein |
| Variola virus strain Sumatra 1970 V70-222 | Orthopoxvirus | 2208 | CD47-like | 580 | VARV-SUM70_222-150 | 55320 | 109726429 | membrane protein |

TABLE 2-continued

Viral Orthologous Clusters V2.0 (VOCs)
CD47-like
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Sumatra 1970 V70-228 | Orthopoxvirus | 2209 | CD47-like | 580 | VARV-SUM70_228-150 | 55522 | 94489044 | membrane protein |
| Variola virus strain Syria 1972 V72-199 | Orthopoxvirus | 2206 | CD47-like | 580 | VARV-SYR72-152 | 54918 | 109726634 | membrane protein |
| Variola virus strain Tanzania 1965 kembula | Orthopoxvirus | 2207 | CD47-like | 580 | VARV-TZA65-152 | 55121 | 94489245 | membrane protein |
| Variola virus strain United Kingdom 1946 Harvey | Orthopoxvirus | 2204 | CD47-like | 580 | VARV-GBR44_harv-152 | 54517 | 94489445 | membrane protein |
| Variola virus strain United Kingdom 1946 Hinden (Middlesex) | Orthopoxvirus | 2205 | CD47-like | 580 | VARV-GBR46_hind-151 | 54718 | 94489647 | membrane protein |
| Variola virus strain United Kingdom 1947 Higgins (Staffordshire) | Orthopoxvirus | 2202 | CD47-like | 580 | VARV-GBR47_hig-152 | 54111 | 94489847 | membrane protein |
| Variola virus strain United Kingdom 1952 Butler | Orthopoxvirus | 2200 | CD47-like | 580 | VARV-GBR52_but-156 | 53904 | 94490051 | membrane protein |
| Variola virus strain Yugoslavia 1972 V72-164 | Orthopoxvirus | 2196 | CD47-like | 580 | VARV-YUG72-152 | 53295 | 94490256 | membrane protein |
| Yaba monkey tumor virus strain Amano | Yatapoxvirus | 1503 | CD47-like | 580 | YMTV-Amano-122 | 43171 | 38229291 | protein 128L |
| Yaba-like Disease Virus strain Davis | Yatapoxvirus | 1487 | CD47-like | 580 | YLDV-Davis-131 | 40180 | 12085111 | 128L |

TABLE 3

Viral Orthologous Clusters V2.0 (VOCs)
chemokine binding
Gene Results Table

| Genome name | Genus | Genome id | Ortholog Group Name | Ortholog Group ID | Gene number | Gene id | Genbank id | Genbank name |
|---|---|---|---|---|---|---|---|---|
| Bovine papular stomatitis virus strain BV-AR02 | Parapoxvirus | 1505 | Chemokine binding protein | 557 | BPSV-AR02-112 | 43452 | 41018864 | 111 |
| Bovine papular stomatitis virus strain BV-AR02 | Parapoxvirus | 1505 | Chemokine binding protein | 557 | BPSV-AR02-117 | 43457 | 41018869 | 116 |
| Camelpox virus strain CMS | Orthopoxvirus | 1493 | Chemokine binding protein | 557 | CMLV-CMS-001 | 41097 | 19717930 | 1L |
| Camelpox virus strain CMS | Orthopoxvirus | 1493 | Chemokine binding protein | 557 | CMLV-CMS-266 | 41362 | 19718194 | 206R |
| Camelpox virus strain M96 | Orthopoxvirus | 1491 | Chemokine binding protein | 557 | CMLV-M96-001 | 40707 | 18640446 | 1 |
| Camelpox virus strain M96 | Orthopoxvirus | 1491 | Chemokine binding protein | 557 | CMLV-M96-213 | 40919 | 18640445 | 211 |
| Cowpox virus strain Brighton Red | Orthopoxvirus | 1496 | Chemokine binding protein | 557 | CPXV-BR-003 | 41702 | 20178372 | 3 |
| Cowpox virus strain Brighton Red | Orthopoxvirus | 1496 | Chemokine binding protein | 557 | CPXV-BR-233 | 41932 | 20178585 | 227 |
| Cowpox virus strain Germany 91-3 | Orthopoxvirus | 2214 | Chemokine binding protein | 557 | CPXV-GER91-001 | 56376 | 90660234 | CC-chemokine-binding protein |
| Cowpox virus strain Germany 91-3 | Orthopoxvirus | 2214 | Chemokine binding protein | 557 | CPXV-GER91-219 | 56594 | 90660452 | CC-chemokine-binding protein |
| Cowpox virus strain GRI-90 | Orthopoxvirus | 1501 | Chemokine binding protein | 557 | CPXV-GRI-001 | 42658 | 30519406 | D1L |
| Cowpox virus strain GRI-90 | Orthopoxvirus | 1501 | Chemokine binding protein | 557 | CPXV-GRI-214 | 42871 | 30519582 | I5R |
| Ectromelia virus strain Moscow | Orthopoxvirus | 1492 | Chemokine binding protein | 557 | ECTV-Mos-001 | 40920 | 22164608 | 1 |
| Ectromelia virus strain Moscow | Orthopoxvirus | 1492 | Chemokine binding protein | 557 | ECTV-Mos-177 | 41096 | 22164607 | 172 |
| Ectromelia virus strain Naval | Orthopoxvirus | 1499 | Chemokine binding protein | 557 | ECTV-Nav-001 | 42256 | 0 | 1_179 |
| Ectromelia virus strain Naval | Orthopoxvirus | 1499 | Chemokine binding protein | 557 | ECTV-Nav-182 | 42437 | 0 | E1 |
| Horsepox virus strain MNR-76 | Orthopoxvirus | 2230 | Chemokine binding protein | 557 | HSPV-MNR76-002 | 59639 | 111184169 | HSPV002 |
| Horsepox virus strain MNR-76 | Orthopoxvirus | 2230 | Chemokine binding protein | 557 | HSPV-MNR76-235 | 59872 | 111184402 | HSPV206 |
| Monkeypox virus strain Congo_2003_358 | Orthopoxvirus | 1524 | Chemokine binding protein | 557 | MPXV-COG_2003_358-001 | 47060 | 68448877 | 1 |
| Monkeypox virus strain Congo_2003_358 | Orthopoxvirus | 1524 | Chemokine binding protein | 557 | MPXV-COG_2003_358-200 | 47259 | 68449076 | 206 |
| Monkeypox virus strain COP-58 | Orthopoxvirus | 1520 | Chemokine binding protein | 557 | MPXV-COP58-001 | 46306 | 59858807 | 1 |
| Monkeypox virus strain COP-58 | Orthopoxvirus | 1520 | Chemokine binding protein | 557 | MPXV-COP58-177 | 46482 | 59858983 | 177 |

TABLE 3-continued

Viral Orthologous Clusters V2.0 (VOCs)
chemokine binding
Gene Results Table

| Genome name | Genus | Genome id | Ortholog Group Name | Ortholog Group ID | Gene number | Gene id | Genbank id | Genbank name |
|---|---|---|---|---|---|---|---|---|
| Monkeypox virus strain Liberia__1970__184 | Orthopoxvirus | 1525 | Chemokine binding protein | 557 | MPXV-LBR__1970__184-001 | 47260 | 68449281 | 1 |
| Monkeypox virus strain Liberia__1970__184 | Orthopoxvirus | 1525 | Chemokine binding protein | 557 | MPXV-LBR__1970__184-198 | 47457 | 68449478 | 206 |
| Monkeypox virus strain Sierra Leone | Orthopoxvirus | 1521 | Chemokine binding protein | 557 | MPXV-SLE-001 | 46483 | 58220471 | 1 |
| Monkeypox virus strain Sierra Leone | Orthopoxvirus | 1521 | Chemokine binding protein | 557 | MPXV-SLE-177 | 46659 | 58220647 | 177 |
| Monkeypox virus strain USA__2003__039 | Orthopoxvirus | 1526 | Chemokine binding protein | 557 | MPXV-USA__2003__039-001 | 47458 | 68449480 | 1 |
| Monkeypox virus strain USA__2003__039 | Orthopoxvirus | 1526 | Chemokine binding protein | 557 | MPXV-USA__2003__039-198 | 47655 | 68449677 | 206 |
| Monkeypox virus strain USA__2003__044 | Orthopoxvirus | 1522 | Chemokine binding protein | 557 | MPXV-USA__2003__044-001 | 46660 | 68448678 | 1 |
| Monkeypox virus strain USA__2003__044 | Orthopoxvirus | 1522 | Chemokine binding protein | 557 | MPXV-USA__2003__044-198 | 46857 | 68448875 | 206 |
| Monkeypox Virus strain Walter Reed 267 | Orthopoxvirus | 1502 | Chemokine binding protein | 557 | MPXV-WR267-001 | 42872 | 0 | 1 |
| Monkeypox Virus strain Walter Reed 267 | Orthopoxvirus | 1502 | Chemokine binding protein | 557 | MPXV-WR267-178 | 43049 | 0 | 177 |
| Monkeypox virus strain Zaire | Orthopoxvirus | 1489 | Chemokine binding protein | 557 | MPXV-ZAR-001 | 40362 | 17974914 | J1L |
| Monkeypox virus strain Zaire | Orthopoxvirus | 1489 | Chemokine binding protein | 557 | MPXV-ZAR-194 | 40555 | 17975104 | J3R |
| Monkeypox virus strain Zaire__1979-005 | Orthopoxvirus | 1523 | Chemokine binding protein | 557 | MPXV-ZAR__1979__005-001 | 46858 | 68449078 | 1 |
| Monkeypox virus strain Zaire__1979-005 | Orthopoxvirus | 1523 | Chemokine binding protein | 557 | MPXV-ZAR__1979__005-202 | 47059 | 68449279 | 206 |
| Myxoma virus strain Lausanne | Leporipoxvirus | 1479 | Chemokine binding protein | 557 | MYXV-Lau-002 | 38427 | 9633793 | m001L |
| Myxoma virus strain Lausanne | Leporipoxvirus | 1479 | Chemokine binding protein | 557 | MYXV-Lau-170 | 38594 | 9633634 | M__T1 |
| Orf virus strain OV-IA82 | Parapoxvirus | 1507 | Chemokine binding protein | 557 | ORFV-IA82-112 | 43913 | 41018599 | 109 |
| Orf virus strain OV-IA82 | Parapoxvirus | 1507 | Chemokine binding protein | 557 | ORFV-IA82-117 | 43918 | 41018604 | 114 |
| Orf virus strain NZ2 | Parapoxvirus | 1527 | Chemokine binding protein | 557 | ORFV-NZ2-111 | 47766 | 74230825 | 112 |
| Orf virus strain NZ2 | Parapoxvirus | 1527 | Chemokine binding protein | 557 | ORFV-NZ2-116 | 47771 | 74230830 | 117 |
| Orf virus strain NZ2 Patent WO03006654 | Parapoxvirus | 1504 | Chemokine binding protein | 557 | ORFV-NZ2__Pat-117 | 43306 | 32167506 | 114 |
| Orf virus strain NZ2 Patent WO03006654 | Parapoxvirus | 1504 | Chemokine binding protein | 557 | ORFV-NZ2__Pat-123 | 43312 | 32167512 | 120 |
| Orf virus strain OV-SA00 | Parapoxvirus | 1508 | Chemokine binding protein | 557 | ORFV-SA00-112 | 44049 | 41018732 | 109 |

TABLE 3-continued

Viral Orthologous Clusters V2.0 (VOCs) chemokine binding Gene Results Table

| Genome name | Genus | Genome id | Ortholog Group Name | Ortholog Group ID | Gene number | Gene id | Genbank id | Genbank name |
|---|---|---|---|---|---|---|---|---|
| Orf virus strain OV-SA00 | Parapoxvirus | 1508 | Chemokine binding protein | 557 | ORFV-SA00-117 | 44054 | 41018737 | 114 |
| Rabbitpox virus strain Utrecht | Orthopoxvirus | 1494 | Chemokine binding protein | 557 | RPXV-Utr-001 | 41363 | 44971364 | 1 |
| Rabbitpox virus strain Utrecht | Orthopoxvirus | 1494 | Chemokine binding protein | 557 | RPXV-Utr-186 | 41548 | 44971547 | 184 |
| Rabbit fibroma virus strain Kasza | Leporipoxvirus | 1480 | Chemokine binding protein | 557 | SFV-Kas-001 | 38596 | 9633810 | gp001L |
| Rabbit fibroma virus strain Kasza | Leporipoxvirus | 1480 | Chemokine binding protein | 557 | SFV-Kas-166 | 38761 | 9633971 | s001R |
| Taterapox virus strain Dahomey 1968 | Orthopoxvirus | 2195 | Chemokine binding protein | 557 | TATV-DAH68-001 | 52919 | 113195178 | chemokine-binding protein |
| Taterapox virus strain Dahomey 1968 | Orthopoxvirus | 2195 | Chemokine binding protein | 557 | TATV-DAH68-002 | 52920 | 113195179 | chemokine-binding protein |
| Taterapox virus strain Dahomey 1968 | Orthopoxvirus | 2195 | Chemokine binding protein | 557 | TATV-DAH68-003 | 52921 | 113195180 | chemokine-binding protein |
| Taterapox virus strain Dahomey 1968 | Orthopoxvirus | 2195 | Chemokine binding protein | 557 | TATV-DAH68-223 | 53141 | 113195400 | chemokine-binding protein |
| Taterapox virus strain Dahomey 1968 | Orthopoxvirus | 2195 | Chemokine binding protein | 557 | TATV-DAH68-224 | 53142 | 113195401 | chemokine-binding protein |
| Taterapox virus strain Dahomey 1968 | Orthopoxvirus | 2195 | Chemokine binding protein | 557 | TATV-DAH68-225 | 53143 | 113195402 | chemokine-binding protein |
| Vaccinia virus strain 3737 | Orthopoxvirus | 1528 | Chemokine binding protein | 557 | VACV-3737-001 | 47789 | 88900617 | 1 |
| Vaccinia virus strain Acambis 2000 | Orthopoxvirus | 2161 | Chemokine binding protein | 557 | VACV-Acam2000-001 | 51057 | 38348859 | 1 |
| Vaccinia virus strain Acambis 2000 | Orthopoxvirus | 2161 | Chemokine binding protein | 557 | VACV-Acam2000-235 | 51291 | 38349093 | 241 |
| Vaccinia virus strain Acambis 3 | Orthopoxvirus | 2162 | Chemokine binding protein | 557 | VACV-Acam3-001 | 51292 | 37551436 | 1 |
| Vaccinia virus strain Acambis 3 | Orthopoxvirus | 2162 | Chemokine binding protein | 557 | VACV-Acam3-229 | 51520 | 37551663 | 241 |
| Vaccinia virus strain Acambis 3000 Modified Virus Ankara | Orthopoxvirus | 1510 | Chemokine binding protein | 557 | VACV-Acam3000-001 | 44315 | 47088327 | 1 |
| Vaccinia virus strain Acambis 3000 Modified Virus Ankara | Orthopoxvirus | 1510 | Chemokine binding protein | 557 | VACV-Acam3000-195 | 44509 | 47088519 | 193 |
| Vaccinia virus strain Copenhagen | Orthopoxvirus | 1485 | Chemokine binding protein | 557 | VACV-Cop-001 | 39526 | 335318 | C23L |
| Vaccinia virus strain Copenhagen | Orthopoxvirus | 1485 | Chemokine binding protein | 557 | VACV-Cop-265 | 39790 | 335577 | B29R |
| Vaccinia virus strain DUKE | Orthopoxvirus | 2458 | Chemokine binding protein | 557 | VACV-DUKE-001 | 63381 | 90819653 | 1 |
| Vaccinia virus strain DUKE | Orthopoxvirus | 2458 | Chemokine binding protein | 557 | VACV-DUKE-225 | 63605 | 90819877 | 225 |
| Vaccinia virus strain LC16m8 | Orthopoxvirus | 1517 | Chemokine binding protein | 557 | VACV-LC16m8-001 | 45454 | 56713344 | m8LTR10L |

TABLE 3-continued

Viral Orthologous Clusters V2.0 (VOCs) chemokine binding Gene Results Table

| Genome name | Genus | Genome id | Ortholog Group Name | Ortholog Group ID | Gene number | Gene id | Genbank id | Genbank name |
|---|---|---|---|---|---|---|---|---|
| Vaccinia virus strain LC16m8 | Orthopoxvirus | 1517 | Chemokine binding protein | 557 | VACV-LC16m8-282 | 45735 | 56713621 | m8RTR10R |
| Vaccinia virus strain LC16mO | Orthopoxvirus | 1518 | Chemokine binding protein | 557 | VACV-LC16mO-001 | 45738 | 56713628 | mOLTR10L |
| Vaccinia virus strain LC16mO | Orthopoxvirus | 1518 | Chemokine binding protein | 557 | VACV-LC16mO-282 | 46019 | 56713905 | mORTR10R |
| Vaccinia virus strain Lister | Orthopoxvirus | 1519 | Chemokine binding protein | 557 | VACV-Lister-001 | 46022 | 0 | m8LTR10L |
| Vaccinia virus strain Lister | Orthopoxvirus | 1519 | Chemokine binding protein | 557 | VACV-Lister-282 | 46303 | 0 | m8RTR10R |
| Vaccinia virus strain Lister_VACV107 | Orthopoxvirus | 2659 | Chemokine binding protein | 557 | VACV-Lister_VACV107-001 | 64334 | 88854292 | List001 |
| Vaccinia virus strain Lister_VACV107 | Orthopoxvirus | 2659 | Chemokine binding protein | 557 | VACV-Lister_VACV107-205 | 64538 | 119352441 | List201 |
| Vaccinia virus strain MVA-I721 | Orthopoxvirus | 2696 | Chemokine binding protein | 557 | VACV-MVA_I721-054 | 65268 | 0 | 193 |
| Vaccinia virus strain Western Reserve | Orthopoxvirus | 1500 | Chemokine binding protein | 557 | VACV-WR-001 | 42438 | 66275798 | 1 |
| Vaccinia virus strain Western Reserve | Orthopoxvirus | 1500 | Chemokine binding protein | 557 | VACV-WR-218 | 42657 | 66276015 | 218 |
| Variola virus strain Afghanistan 1970 Variolator 4 | Orthopoxvirus | 2197 | Chemokine binding protein | 557 | VARV-AFG70-203 | 53547 | 109724242 | CC-chemokine-binding protein |
| Variola virus strain Benin, Dahomey 1968 (v68-59) | Orthopoxvirus | 2224 | Chemokine binding protein | 557 | VARV-BEN68-208 | 58618 | 94483845 | CC-chemokine-binding protein |
| Variola virus strain Bangladesh 1974 (nur islam) | Orthopoxvirus | 2215 | Chemokine binding protein | 557 | VARV-BGD74_nur-198 | 56792 | 94484656 | CC-chemokine-binding protein |
| Variola virus strain Bangladesh 1974 (Shahzaman) | Orthopoxvirus | 2216 | Chemokine binding protein | 557 | VARV-BGD74_shz-198 | 56990 | 94484854 | CC-chemokine-binding protein |
| Variola virus strain Bangladesh 1974 (Solaiman) | Orthopoxvirus | 2217 | Chemokine binding protein | 557 | VARV-BGD74_sol-198 | 57188 | 94485052 | CC-chemokine-binding protein |
| Variola virus strain Bangladesh 1975 v75-550 Banu | Orthopoxvirus | 2198 | Chemokine binding protein | 557 | VARV-BGD75_Banu-201 | 53748 | 109724444 | CC-chemokine-binding protein |
| Variola major virus strain Bangladesh 1975 | Orthopoxvirus | 1481 | Chemokine binding protein | 557 | VARV-BGD75maj-192 | 38953 | 439103 | G3R |
| Variola virus strain Brazil 1966 (v66-39 Sao Paulo) | Orthopoxvirus | 2227 | Chemokine binding protein | 557 | VARV-BRA66-210 | 59233 | 94484458 | CC-chemokine-binding protein |
| Variola virus strain Botswana 1972 (v72-143) | Orthopoxvirus | 2225 | Chemokine binding protein | 557 | VARV-BWA72-202 | 58821 | 94484049 | CC-chemokine-binding protein |
| Variola virus strain Botswana 1973 (v73-225) | Orthopoxvirus | 2226 | Chemokine binding protein | 557 | VARV-BWA73-202 | 59023 | 94484251 | CC-chemokine-binding protein |
| Variola virus strain China Horn 1948 Sabin Lab July 1948 | Orthopoxvirus | 2203 | Chemokine binding protein | 557 | VARV-CHN48-204 | 54364 | 109724648 | CC-chemokine-binding protein |
| Variola virus strain Congo 9 1970 (v74-227 Gispen) | Orthopoxvirus | 2228 | Chemokine binding protein | 557 | VARV-COG70_227-201 | 59435 | 94485253 | CC-chemokine-binding protein |
| Variola virus strain Congo 1970 v70-46 Kinshasa | Orthopoxvirus | 2229 | Chemokine binding protein | 557 | VARV-COG70_46-202 | 59637 | 109724853 | CC-chemokine-binding protein |

TABLE 3-continued

Viral Orthologous Clusters V2.0 (VOCs) chemokine binding Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Germany 1958 Heidelberg | Orthopoxvirus | 2233 | Chemokine binding protein | 557 | VARV-DEU58-201 | 60478 | 109725055 | CC-chemokine-binding protein |
| Variola virus strain Ethiopia 1972 (Eth16 R14-1X-72 Addis) | Orthopoxvirus | 2231 | Chemokine binding protein | 557 | VARV-ETH72_16-203 | 60076 | 94485456 | CC-chemokine-binding protein |
| Variola virus strain Ethiopia 1972 (Eth17 R14-1X-72 Addis) | Orthopoxvirus | 2232 | Chemokine binding protein | 557 | VARV-ETH72_17-201 | 60277 | 94485658 | CC-chemokine-binding protein |
| Variola virus strain United Kingdom 1946 Harvey | Orthopoxvirus | 2204 | Chemokine binding protein | 557 | VARV-GBR44_harv-202 | 54567 | 94489495 | CC-chemokine-binding protein |
| Variola virus strain United Kingdom 1946 Hinden (Middlesex) | Orthopoxvirus | 2205 | Chemokine binding protein | 557 | VARV-GBR46_hind-199 | 54766 | 94489694 | CC-chemokine-binding protein |
| Variola virus strain United Kingdom 1947 Higgins (Staffordshire) | Orthopoxvirus | 2202 | Chemokine binding protein | 557 | VARV-GBR47_hig-201 | 54160 | 94489895 | CC-chemokine-binding protein |
| Variola virus strain United Kingdom 1952 Butler | Orthopoxvirus | 2200 | Chemokine binding protein | 557 | VARV-GBR52_but-210 | 53958 | 94490102 | CC-chemokine-binding protein |
| Variola virus strain Guinea 1969 (005) | Orthopoxvirus | 2234 | Chemokine binding protein | 557 | VARV-GIN69-206 | 60684 | 94485861 | CC-chemokine-binding protein |
| Variola minor virus strain Garcia 1966 | Orthopoxvirus | 1482 | Chemokine binding protein | 557 | VARV-Gar_1966-208 | 39161 | 5830760 | G3R |
| Variola virus strain India 3 Major 1967 | Orthopoxvirus | 1483 | Chemokine binding protein | 557 | VARV-IND3_1967-200 | 39362 | 9627718 | G5R |
| Variola virus strain India 1953 (Kali-Muthu-M50 Madras) | Orthopoxvirus | 2238 | Chemokine binding protein | 557 | VARV-IND53_mad-201 | 61491 | 94486064 | CC-chemokine-binding protein |
| Variola virus strain India 1953 (New Delhi) | Orthopoxvirus | 2239 | Chemokine binding protein | 557 | VARV-IND53_ndel-201 | 61692 | 94486266 | CC-chemokine-binding protein |
| Variola virus strain India 1964 7124 Vellore | Orthopoxvirus | 2240 | Chemokine binding protein | 557 | VARV-IND64_vel4-205 | 61898 | 109725261 | CC-chemokine-binding protein |
| Variola virus strain India 1964 7125 Vellore | Orthopoxvirus | 2241 | Chemokine binding protein | 557 | VARV-IND64_vel5-203 | 62101 | 109725464 | CC-chemokine-binding protein |
| Variola virus strain Iran 1972 2602 Tabriz | Orthopoxvirus | 2235 | Chemokine binding protein | 557 | VARV-IRN72-203 | 60888 | 109725668 | CC-chemokine-binding protein |
| Variola virus strain Japan 1946 (Yamada MS-2(A) Tokyo) | Orthopoxvirus | 2243 | Chemokine binding protein | 557 | VARV-JPN46_yam-201 | 62476 | 94486469 | CC-chemokine-binding protein |
| Variola virus strain Japan 1951 (Harper, Masterseed) | Orthopoxvirus | 2244 | Chemokine binding protein | 557 | VARV-JPN51_hrpr-200 | 62677 | 94486671 | CC-chemokine-binding protein |
| Variola virus strain Japan 1951 (Stillwell, Masterseed) | Orthopoxvirus | 2245 | Chemokine binding protein | 557 | VARV-JPN51_stwl-201 | 62879 | 94486873 | CC-chemokine-binding protein |
| Variola virus strain Korea 1947 (Lee, Masterseed) | Orthopoxvirus | 2236 | Chemokine binding protein | 557 | VARV-KOR47-202 | 61090 | 94487077 | CC-chemokine-binding protein |
| Variola virus strain Kuwait 1967 (K1629) | Orthopoxvirus | 2237 | Chemokine binding protein | 557 | VARV-KWT67-200 | 61290 | 94487277 | CC-chemokine-binding protein |
| Variola virus strain Niger 1969 (001, importation from Nigeria) | Orthopoxvirus | 2222 | Chemokine binding protein | 557 | VARV-NER69-208 | 58201 | 94487482 | CC-chemokine-binding protein |
| Variola virus strain Nepal 1973 V73-175 | Orthopoxvirus | 2221 | Chemokine binding protein | 557 | VARV-NPL73-202 | 57992 | 109725870 | CC-chemokine-binding protein |
| Variola virus strain Sudan 1947 (Juba) | Orthopoxvirus | 2212 | Chemokine binding protein | 557 | VARV-SDN47_jub-200 | 56174 | 94488692 | CC-chemokine-binding protein |

TABLE 3-continued

Viral Orthologous Clusters V2.0 (VOCs) chemokine binding Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Sudan 1947 (Rumbec) | Orthopoxvirus | 2213 | Chemokine binding protein | 557 | VARV-SDN47_rum-201 | 56375 | 94488893 | CC-chemokine-binding protein |
| Variola virus strain Sierra Leone 1969 (V68-258) | Orthopoxvirus | 2223 | Chemokine binding protein | 557 | VARV-SLE68-207 | 58409 | 94488090 | CC-chemokine-binding protein |
| Variola virus strain Somalia 1977 (V77-1252) | Orthopoxvirus | 2218 | Chemokine binding protein | 557 | VARV-SOM77_1252-200 | 57388 | 94488291 | CC-chemokine-binding protein |
| Variola virus strain Somalia 1977 (V77-1605) | Orthopoxvirus | 2219 | Chemokine binding protein | 557 | VARV-SOM77_1605-200 | 57588 | 94488491 | CC-chemokine-binding protein |
| Variola virus strain Somalia 1977 V77-2479 | Orthopoxvirus | 2220 | Chemokine binding protein | 557 | VARV-SOM77_ali-202 | 57790 | 109726278 | CC-chemokine-binding protein |
| Variola virus strain Sumatra 1970 V70-222 | Orthopoxvirus | 2208 | Chemokine binding protein | 557 | VARV-SUM70_222-201 | 55371 | 109726480 | CC-chemokine-binding protein |
| Variola virus strain Sumatra 1970 V70-228 | Orthopoxvirus | 2209 | Chemokine binding protein | 557 | VARV-SUM70_228-199 | 55571 | 94489092 | CC-chemokine-binding protein |
| Variola virus strain Syria 1972 V72-199 | Orthopoxvirus | 2206 | Chemokine binding protein | 557 | VARV-SYR72-203 | 54969 | 109726685 | CC-chemokine-binding protein |
| Variola virus strain Tanzania 1965 kembula | Orthopoxvirus | 2207 | Chemokine binding protein | 557 | VARV-TZA65-201 | 55170 | 94489292 | CC-chemokine-binding protein |
| Variola virus strain Yugoslavia 1972 V72-164 | Orthopoxvirus | 2196 | Chemokine binding protein | 557 | VARV-YUG72-201 | 53344 | 94490305 | CC-chemokine-binding protein |
| Variola virus strain South Africa 1965 (102 Natal, Ingwavuma) | Orthopoxvirus | 2210 | Chemokine binding protein | 557 | VARV-ZAF65_102-201 | 55773 | 94487684 | CC-chemokine-binding protein |
| Variola virus strain South Africa 1965 (103 Tvaal, Nelspruit) | Orthopoxvirus | 2211 | Chemokine binding protein | 557 | VARV-ZAF65_103-201 | 55974 | 94487886 | CC-chemokine-binding protein |

TABLE 4

Viral Orthologous Clusters V2.0 (VOCs)
complement binding protein
Gene Results Table

| Genome name | Genus | Genome id | Ortholog Group Name | Ortholog Group ID | Gene Name | Gene number | Gene id | Genbank id | Genbank name |
|---|---|---|---|---|---|---|---|---|---|
| Camelpox virus strain CMS | Orthopoxvirus | 1493 | Complement binding (secreted) | 604 | CMLV-CMS-025 | 41121 | 19717954 | 23L |
| Camelpox virus strain CMS | Orthopoxvirus | 1493 | Complement control/CD46/EEV | 591 | CMLV-CMS-230 | 41326 | 19718158 | 178R |
| Camelpox virus strain M96 | Orthopoxvirus | 1491 | Complement binding (secreted) | 604 | CMLV-M96-023 | 40729 | 18640257 | 23 |
| Camelpox virus strain M96 | Orthopoxvirus | 1491 | Complement control/CD46/EEV | 591 | CMLV-M96-183 | 40889 | 18640415 | 181 |
| Cowpox virus strain Brighton Red | Orthopoxvirus | 1496 | Complement binding (secreted) | 604 | CPXV-BR-034 | 41733 | 20178402 | 34 |
| Cowpox virus strain Brighton Red | Orthopoxvirus | 1496 | Complement control/CD46/EEV | 591 | CPXV-BR-205 | 41904 | 20178559 | 199 |
| Cowpox virus strain GRI-90 | Orthopoxvirus | 1501 | Complement binding (secreted) | 604 | CPXV-GRI-031 | 42688 | 1808620 | C17L |
| Cowpox virus strain GRI-90 | Orthopoxvirus | 1501 | Complement control/CD46/EEV | 591 | CPXV-GRI-187 | 42844 | 30519555 | B4R |
| Cowpox virus strain Germany 91-3 | Orthopoxvirus | 2214 | Complement binding (secreted) | 604 | CPXV-GER91-032 | 56407 | 90660265 | secreted protein |
| Cowpox virus strain Germany 91-3 | Orthopoxvirus | 2214 | Complement control/CD46/EEV | 591 | CPXV-GER91-186 | 56561 | 90660419 | EEV membrane glycoprotein |
| Deepox virus strain W-1170-84 | Unclassified | 1516 | Complement control/CD46/EEV | 591 | DPV-W1170_84-155 | 45438 | 0 | 156 |
| Deepox virus strain W-848-83 | Unclassified | 1515 | Complement control/CD46/EEV | 591 | DPV-W848_83-154 | 45267 | 62637533 | 156 |
| Ectromelia virus strain Moscow | Orthopoxvirus | 1492 | Complement binding (secreted) | 604 | ECTV-Mos-018 | 40937 | 22164624 | 17 |
| Ectromelia virus strain Moscow | Orthopoxvirus | 1492 | Complement control/CD46/EEV | 591 | ECTV-Mos-160 | 41079 | 22164590 | 155 |
| Ectromelia virus strain Naval | Orthopoxvirus | 1499 | Complement binding (secreted) | 604 | ECTV-Nav-018 | 42273 | 0 | 28 |
| Ectromelia virus strain Naval | Orthopoxvirus | 1499 | Complement control/CD46/EEV | 591 | ECTV-Nav-165 | 42420 | 0 | 182 |
| Goatpox virus strain G20-LKV | Capripoxvirus | 1514 | Complement control/CD46/EEV | 591 | GTPV-G20LKV-140 | 45100 | 0 | 134 |
| Goatpox virus strain Pellor | Capripoxvirus | 1513 | Complement control/CD46/EEV | 591 | GTPV-Pellor-138 | 44948 | 0 | 134 |
| Horsepox virus strain MNR-76 | Orthopoxvirus | 2230 | Complement binding (secreted) | 604 | HSPV-MNR76-042 | 59679 | 111184209 | HSPV028 |
| Horsepox virus strain MNR-76 | Orthopoxvirus | 2230 | Complement control/CD46/EEV | 591 | HSPV-MNR76-207 | 59844 | 111184374 | HSPV182 |
| Lumpy skin disease virus strain Neethling 2490 | Capripoxvirus | 1488 | Complement control/CD46/EEV | 591 | LSDV-Nee-143 | 40346 | 15150580 | 141 |
| Lumpy skin disease virus strain Neethling Warmbaths LW | Capripoxvirus | 1497 | Complement control/CD46/EEV | 591 | LSDV-NW_LW-145 | 42079 | 22595676 | 141 |
| Lumpy skin disease virus strain vaccine LW 1959 | Capripoxvirus | 1498 | Complement control/CD46/EEV | 591 | LSDV-LW1959-145 | 42239 | 22595835 | 141 |
| Monkeypox Virus strain Walter Reed 267 | Orthopoxvirus | 1502 | Complement control/CD46/EEV | 591 | MPXV-WR267-160 | 43031 | 0 | 159 |
| Monkeypox virus strain COP-58 | Orthopoxvirus | 1520 | Complement control/CD46/EEV | 591 | MPXV-COP58-159 | 46464 | 59858965 | 159 |
| Monkeypox virus strain Congo_2003_358 | Orthopoxvirus | 1524 | Complement binding (secreted) | 604 | MPXV-COG_2003_358-019 | 47078 | 68448895 | 22 |
| Monkeypox virus strain Congo_2003_358 | Orthopoxvirus | 1524 | Complement control/CD46/EEV | 591 | MPXV-COG_2003_358-173 | 47232 | 68449049 | 180 |
| Monkeypox virus strain Liberia_1970_184 | Orthopoxvirus | 1525 | Complement control/CD46/EEV | 591 | MPXV-LBR_1970_184-172 | 47431 | 68449452 | 180 |
| Monkeypox virus strain Sierra Leone | Orthopoxvirus | 1521 | Complement control/CD46/EEV | 591 | MPXV-SLE-159 | 46641 | 58220629 | 159 |
| Monkeypox virus strain USA_2003_039 | Orthopoxvirus | 1526 | Complement control/CD46/EEV | 591 | MPXV-USA_2003_039-173 | 47630 | 68449652 | 180 |
| Monkeypox virus strain USA_2003_044 | Orthopoxvirus | 1522 | Complement control/CD46/EEV | 591 | MPXV-USA_2003_044-173 | 46832 | 68448850 | 180 |
| Monkeypox virus strain Zaire | Orthopoxvirus | 1489 | Complement binding (secreted) | 604 | MPXV-ZAR-017 | 40378 | 17974930 | D14L |
| Monkeypox virus strain Zaire | Orthopoxvirus | 1489 | Complement control/CD46/EEV | 591 | MPXV-ZAR-170 | 40531 | 17975080 | B6R |
| Monkeypox virus strain Zaire_1979-005 | Orthopoxvirus | 1523 | Complement binding (secreted) | 604 | MPXV-ZAR_1979_005-019 | 46876 | 68449096 | 22 |
| Monkeypox virus strain Zaire_1979-005 | Orthopoxvirus | 1523 | Complement control/CD46/EEV | 591 | MPXV-ZAR_1979_005-174 | 47031 | 68449251 | 180 |
| Myxoma virus strain Lausanne | Leporipoxvirus | 1479 | Complement control/CD46/EEV | 591 | MYXV-Lau-149 | 38573 | 9633780 | m144R |
| Rabbit fibroma virus strain Kasza | Leporipoxvirus | 1480 | Complement control/CD46/EEV | 591 | SFV-Kas-146 | 38741 | 9633950 | gp144R |
| Rabbitpox virus strain Utrecht | Orthopoxvirus | 1494 | Complement binding (secreted) | 604 | RPXV-Utr-017 | 41379 | 44971380 | 17 |
| Rabbitpox virus strain Utrecht | Orthopoxvirus | 1494 | Complement control/CD46/EEV | 591 | RPXV-Utr-169 | 41531 | 44971530 | 167 |
| Sheeppox virus strain A | Capripoxvirus | 1511 | Complement control/CD46/EEV | 591 | SPPV-A-137 | 44646 | 0 | 134 |
| Sheeppox virus strain NISKHI | Capripoxvirus | 1512 | Complement control/CD46/EEV | 591 | SPPV-NISKHI-136 | 44795 | 0 | 134 |

TABLE 4-continued

Viral Orthologous Clusters V2.0 (VOCs)
complement binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Sheeppox virus strain TU-V02127 | Capripoxvirus | 1495 | Complement control/CD46/EEV | 591 | SPPV-TU-138 | 41686 | 21492591 | 134 |
| Swinepox virus strain Nebraska 17077-99 | Suipoxvirus | 1490 | Complement control/CD46/EEV | 591 | SWPV-Neb-140 | 40695 | 18640225 | 139 |
| Tanapox virus strain Kenya | Yatapoxvirus | 3496 | Complement control/CD46/EEV | 591 | TANV-KEN-149 | 67676 | 146746484 | 144R |
| Tanapox virus strain isolate TPV-RoC | Yatapoxvirus | 3497 | Complement control/CD46/EEV | 591 | TANV-COD-148 | 67760 | 146746640 | 144R |
| Taterapox virus strain Dahomey 1968 | Orthopoxvirus | 2195 | Complement binding (secreted) | 604 | TATV-DAH68-026 | 52944 | 113195203 | secreted protein |
| Taterapox virus strain Dahomey 1968 | Orthopoxvirus | 2195 | Complement control/CD46/EEV | 591 | TATV-DAH68-188 | 53106 | 113195365 | EEV membrane glycoprotein |
| Vaccinia virus strain 3737 | Orthopoxvirus | 1528 | Complement binding (secreted) | 604 | VACV-3737-027 | 47815 | 88900643 | 24 |
| Vaccinia virus strain 3737 | Orthopoxvirus | 1528 | Complement control/CD46/EEV | 591 | VACV-3737-188 | 47976 | 88900804 | 177 |
| Vaccinia virus strain Acambis 2000 | Orthopoxvirus | 2161 | Complement binding (secreted) | 604 | VACV-Acam2000-034 | 51090 | 38348892 | 34 |
| Vaccinia virus strain Acambis 2000 | Orthopoxvirus | 2161 | Complement control/CD46/EEV | 591 | VACV-Acam2000-196 | 51252 | 38349054 | 198 |
| Vaccinia virus strain Acambis 3 | Orthopoxvirus | 2162 | Complement binding (secreted) | 604 | VACV-Acam3-034 | 51325 | 37551468 | 34 |
| Vaccinia virus strain Acambis 3 | Orthopoxvirus | 2162 | Complement control/CD46/EEV | 591 | VACV-Acam3-198 | 51489 | 37551632 | 198 |
| Vaccinia virus strain Acambis 3000 | Orthopoxvirus | 1510 | Complement control/CD46/EEV | 591 | VACV-Acam3000-175 | 44489 | 47088499 | 173 |
| Vaccinia virus strain Copenhagen | Orthopoxvirus | 1485 | Complement binding (secreted) | 604 | VACV-Cop-028 | 39553 | 335345 | C3L |
| Vaccinia virus strain Copenhagen | Orthopoxvirus | 1485 | Complement control/CD46/EEV | 591 | VACV-Cop-237 | 39762 | 335549 | B5R |
| Vaccinia virus strain DUKE | Orthopoxvirus | 2458 | Complement binding (secreted) | 604 | VACV-DUKE-034 | 63414 | 90819686 | 34 |
| Vaccinia virus strain DUKE | Orthopoxvirus | 2458 | Complement control/CD46/EEV | 591 | VACV-DUKE-196 | 63576 | 90819848 | 196 |
| Vaccinia virus strain LC16m8 | Orthopoxvirus | 1517 | Complement binding (secreted) | 604 | VACV-LC16m8-036 | 45489 | 56713377 | m8025L |
| Vaccinia virus strain LC16m8 | Orthopoxvirus | 1517 | Complement control/CD46/EEV | 591 | VACV-LC16m8-253 | 45706 | 56713592 | m8243R |
| Vaccinia virus strain LC16mO | Orthopoxvirus | 1518 | Complement binding (secreted) | 604 | VACV-LC16mO-036 | 45773 | 56713661 | mO025L |
| Vaccinia virus strain LC16mO | Orthopoxvirus | 1518 | Complement control/CD46/EEV | 591 | VACV-LC16mO-253 | 45990 | 56713876 | mO243R |
| Vaccinia virus strain Lister | Orthopoxvirus | 1519 | Complement binding (secreted) | 604 | VACV-Lister-036 | 46057 | 0 | m8025L |
| Vaccinia virus strain Lister | Orthopoxvirus | 1519 | Complement control/CD46/EEV | 591 | VACV-Lister-253 | 46274 | 0 | m8243R |
| Vaccinia virus strain Lister_VACV107 | Orthopoxvirus | 2659 | Complement binding (secreted) | 604 | VACV-Lister_VACV107-026 | 64359 | 88854053 | List022 |
| Vaccinia virus strain Lister_VACV107 | Orthopoxvirus | 2659 | Complement control/CD46/EEV | 591 | VACV-Lister_VACV107-186 | 64519 | 88854268 | List182 |
| Vaccinia virus strain MVA-I721 | Orthopoxvirus | 2696 | Complement control/CD46/EEV | 591 | VACV-MVA_I721-095 | 65309 | 0 | 173 |
| Vaccinia virus strain Western Reserve | Orthopoxvirus | 1500 | Complement binding (secreted) | 604 | VACV-WR-025 | 42462 | 66275822 | 25 |
| Vaccinia virus strain Western Reserve | Orthopoxvirus | 1500 | Complement control/CD46/EEV | 591 | VACV-WR-187 | 42626 | 66275984 | 187 |
| Vaccinia virus strain modified vaccinia Ankara | Orthopoxvirus | 1484 | Complement control/CD46/EEV | 591 | VACV-MVA-151 | 65563 | 2772808 | MVA173R |
| Variola major virus strain Bangladesh 1975 | Orthopoxvirus | 1481 | Complement binding (secreted) | 604 | VARV-BGD75maj-015 | 38776 | 438930 | D15L |
| Variola major virus strain Bangladesh 1975 | Orthopoxvirus | 1481 | Complement control/CD46/EEV | 591 | VARV-BGD75maj-173 | 38934 | 439084 | B6R |
| Variola minor virus strain Garcia 1966 | Orthopoxvirus | 1482 | Complement binding (secreted) | 604 | VARV-Gar_1966-018 | 38971 | 5830573 | B18L |
| Variola minor virus strain Garcia 1966 | Orthopoxvirus | 1482 | Complement control/CD46/EEV | 591 | VARV-Gar_1966-185 | 39138 | 5830737 | H7R |
| Variola virus strain Afghanistan 1970 | Orthopoxvirus | 2197 | Complement control/CD46/EEV | 604 | VARV-AFG70-015 | 53359 | 109724054 | secreted protein |
| Variolator 4 | Orthopoxvirus | 2197 | Complement control/CD46/EEV | 591 | VARV-AFG70-178 | 53522 | 109724217 | glycoprotein |
| Variola virus strain Bangladesh 1974 (Shahzaman) | Orthopoxvirus | 2216 | Complement binding (secreted) | 604 | VARV-BGD74_shz-015 | 56807 | 94484672 | secreted protein |
| Variola virus strain Bangladesh 1974 (Shahzaman) | Orthopoxvirus | 2216 | Complement control/CD46/EEV | 591 | VARV-BGD74_shz-177 | 56969 | 94484834 | glycoprotein |

TABLE 4-continued

Viral Orthologous Clusters V2.0 (VOCs)
complement binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Bangladesh 1974 (Solaiman) | Orthopoxvirus | 2217 | Complement binding (secreted) | 604 | VARV-BGD74_sol-015 | 57005 | 94484870 | secreted protein |
| Variola virus strain Bangladesh 1974 (Solaiman) | Orthopoxvirus | 2217 | Complement control/CD46/EEV | 591 | VARV-BGD74_sol-177 | 57167 | 94485032 | glycoprotein |
| Variola virus strain Bangladesh 1974 (nur islam) | Orthopoxvirus | 2215 | Complement binding (secreted) | 604 | VARV-BGD74_nur-015 | 56609 | 94484475 | secreted protein |
| Variola virus strain Bangladesh 1974 (nur islam) | Orthopoxvirus | 2215 | Complement control/CD46/EEV | 591 | VARV-BGD74_nur-177 | 56771 | 94484636 | glycoprotein |
| Variola virus strain Bangladesh 1975 v75-550 Banu | Orthopoxvirus | 2198 | Complement binding (secreted) | 604 | VARV-BGD75_Banu-015 | 53562 | 109724258 | secreted protein |
| Variola virus strain Bangladesh 1975 v75-550 Banu | Orthopoxvirus | 2198 | Complement control/CD46/EEV | 591 | VARV-BGD75_Banu-177 | 53724 | 109724420 | glycoprotein |
| Variola virus strain Benin, Dahomey 1968 (v68-59) | Orthopoxvirus | 2224 | Complement binding (secreted) | 604 | VARV-BEN68-017 | 58427 | 94483658 | secreted protein |
| Variola virus strain Benin, Dahomey 1968 (v68-59) | Orthopoxvirus | 2224 | Complement control/CD46/EEV | 591 | VARV-BEN68-182 | 58592 | 94483822 | glycoprotein |
| Variola virus strain Botswana 1972 (v72-143) | Orthopoxvirus | 2225 | Complement binding (secreted) | 604 | VARV-BWA72-015 | 58634 | 94483862 | secreted protein |
| Variola virus strain Botswana 1972 (v72-143) | Orthopoxvirus | 2225 | Complement control/CD46/EEV | 591 | VARV-BWA72-178 | 58797 | 94484025 | glycoprotein |
| Variola virus strain Botswana 1973 (v73-225) | Orthopoxvirus | 2226 | Complement binding (secreted) | 604 | VARV-BWA73-015 | 58836 | 94484065 | secreted protein |
| Variola virus strain Botswana 1973 (v73-225) | Orthopoxvirus | 2226 | Complement contro/CD46/EEV | 591 | VARV-BWA73-178 | 58999 | 94484228 | glycoprotein |
| Variola virus strain Brazil 1966 (v66-39 Sao Paulo) | Orthopoxvirus | 2227 | Complement binding (secreted) | 604 | VARV-BRA66-019 | 59042 | 94484271 | secreted protein |
| Variola virus strain Brazil 1966 (v66-39 Sao Paulo) | Orthopoxvirus | 2227 | Complement control/CD46/EEV | 591 | VARV-BRA66-185 | 59208 | 94484436 | glycoprotein |
| Variola virus strain China Horn 1948 Sabin Lab July 1948 | Orthopoxvirus | 2203 | Complement binding (secreted) | 604 | VARV-CHN48-015 | 54175 | 109724460 | secreted protein |
| Variola virus strain China Horn 1948 Sabin Lab July 1948 | Orthopoxvirus | 2203 | Complement control/CD46/EEV | 591 | VARV-CHN48-179 | 54339 | 109724624 | glycoprotein |
| Variola virus strain Congo 1970 v70-46 Kinshasa | Orthopoxvirus | 2229 | Complement binding (secreted) | 604 | VARV-COG70_46-015 | 59450 | 109724665 | secreted protein |
| Variola virus strain Congo 1970 v70-46 Kinshasa | Orthopoxvirus | 2229 | Complement control/CD46/EEV | 591 | VARV-COG70_46-177 | 59612 | 109724828 | glycoprotein |
| Variola virus strain Congo 9 1970 (v74-227 Gispen) | Orthopoxvirus | 2228 | Complement binding (secreted) | 604 | VARV-COG70_227-015 | 59249 | 94485068 | secreted protein |
| Variola virus strain Congo 9 1970 (v74-227 Gispen) | Orthopoxvirus | 2228 | Complement control/CD46/EEV | 591 | VARV-COG70_227-178 | 59412 | 94485231 | glycoprotein |
| Variola virus strain Ethiopia 1972 (Eth16 R14-1X-72 Addis) | Orthopoxvirus | 2231 | Complement binding (secreted) | 604 | VARV-ETH72_16-015 | 59888 | 94485269 | secreted protein |
| Variola virus strain Ethiopia 1972 (Eth16 R14-1X-72 Addis) | Orthopoxvirus | 2231 | Complement control/CD46/EEV | 591 | VARV-ETH72_16-179 | 60052 | 94485433 | glycoprotein |
| Variola virus strain Ethiopia 1972 (Eth17 R14-1X-72 Addis) | Orthopoxvirus | 2232 | Complement binding (secreted) | 604 | VARV-ETH72_17-015 | 60091 | 94485472 | secreted protein |

TABLE 4-continued

Viral Orthologous Clusters V2.0 (VOCs)
complement binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Ethiopia 1972 (Eth17 R14-1X-72 Addis) | Orthopoxvirus | 2232 | Complement control/CD46/EEV | 591 | VARV-ETH72__17-179 | 60255 | 94485636 | glycoprotein |
| Variola virus strain Germany 1958 Heidelberg | Orthopoxvirus | 2233 | Complement binding (secreted) | 604 | VARV-DEU58-015 | 60292 | 109724869 | secreted protein |
| Variola virus strain Germany 1958 Heidelberg | Orthopoxvirus | 2233 | Complement control/CD46/EEV | 591 | VARV-DEU58-177 | 60454 | 109725031 | glycoprotein |
| Variola virus strain Guinea 1969 (005) | Orthopoxvirus | 2234 | Complement binding (secreted) | 604 | VARV-GIN69-017 | 60495 | 94485676 | secreted protein |
| Variola virus strain Guinea 1969 (005) | Orthopoxvirus | 2234 | Complement control/CD46/EEV | 591 | VARV-GIN69-181 | 60659 | 94485839 | glycoprotein |
| Variola virus strain India 1953 (Kali-Muthu-M50 Madras) | Orthopoxvirus | 2238 | Complement binding (secreted) | 604 | VARV-IND53_mad-015 | 61305 | 94485878 | secreted protein |
| Variola virus strain India 1953 (Kali-Muthu-M50 Madras) | Orthopoxvirus | 2238 | Complement control/CD46/EEV | 591 | VARV-IND53_mad-179 | 61469 | 94486042 | glycoprotein |
| Variola virus strain India 1953 (New Delhi) | Orthopoxvirus | 2239 | Complement binding (secreted) | 604 | VARV-IND53_ndel-014 | 61505 | 94486079 | secreted protein |
| Variola virus strain India 1953 (New Delhi) | Orthopoxvirus | 2239 | Complement control/CD46/EEV | 591 | VARV-IND53_ndel-178 | 61669 | 94486243 | glycoprotein |
| Variola virus strain India 1964 7124 Vellore | Orthopoxvirus | 2240 | Complement binding (secreted) | 604 | VARV-IND64_vel4-016 | 61709 | 109725072 | secreted protein |
| Variola virus strain India 1964 7124 Vellore | Orthopoxvirus | 2240 | Complement control/CD46/EEV | 591 | VARV-IND64_vel4-180 | 61873 | 109725236 | glycoprotein |
| Variola virus strain India 1964 7125 Vellore | Orthopoxvirus | 2241 | Complement binding (secreted) | 604 | VARV-IND64_vel5-015 | 61913 | 109725277 | secreted protein |
| Variola virus strain India 1964 7125 Vellore | Orthopoxvirus | 2241 | Complement control/CD46/EEV | 591 | VARV-IND64_vel5-179 | 62077 | 109725441 | EEV membrane glycoprotein |
| Variola virus strain India 3 Major 1967 | Orthopoxvirus | 1483 | Complement binding (secreted) | 604 | VARV-IND3_1967-012 | 39174 | 9627533 | D12L |
| Variola virus strain India 3 Major 1967 | Orthopoxvirus | 1483 | Complement control/CD46/EEV | 591 | VARV-IND3_1967-178 | 39340 | 9627696 | B7R |
| Variola virus strain Iran 1972 2602 Tabriz | Orthopoxvirus | 2235 | Complement binding (secreted) | 604 | VARV-IRN72-015 | 60700 | 109725480 | secreted protein |
| Variola virus strain Iran 1972 2602 Tabriz | Orthopoxvirus | 2235 | Complement control/CD46/EEV | 591 | VARV-IRN72-178 | 60863 | 109725643 | glycoprotein |
| Variola virus strain Japan 1946 (Yamada MS-2(A) Tokyo) | Orthopoxvirus | 2243 | Complement binding (secreted) | 604 | VARV-JPN46_yam-014 | 62289 | 94486282 | secreted protein |
| Variola virus strain Japan 1946 (Yamada MS-2(A) Tokyo) | Orthopoxvirus | 2243 | Complement control/CD46/EEV | 591 | VARV-JPN46_yam-178 | 62453 | 94486446 | glycoprotein |
| Variola virus strain Japan 1951 (Harper, Masterseed) | Orthopoxvirus | 2244 | Complement binding (secreted) | 604 | VARV-JPN51_hrpr-014 | 62491 | 94486485 | secreted protein |
| Variola virus strain Japan 1951 (Harper, Masterseed) | Orthopoxvirus | 2244 | Complement control/CD46/EEV | 591 | VARV-JPN51_hrpr-178 | 62655 | 94486649 | glycoprotein |
| Variola virus strain Japan 1951 (Stillwell, Masterseed) | Orthopoxvirus | 2245 | Complement binding (secreted) | 604 | VARV-JPN51_stwl-014 | 62692 | 94486687 | secreted protein |
| Variola virus strain Japan 1951 (Stillwell, Masterseed) | Orthopoxvirus | 2245 | Complement control/CD46/EEV | 591 | VARV-JPN51_stwl-178 | 62856 | 94486851 | glycoprotein |
| Variola virus strain Korea 1947 (Lee, Masterseed) | Orthopoxvirus | 2236 | Complement binding (secreted) | 604 | VARV-KOR47-015 | 60903 | 94486890 | secreted protein |
| Variola virus strain Korea 1947 (Lee, Masterseed) | Orthopoxvirus | 2236 | Complement control/CD46/EEV | 591 | VARV-KOR47-179 | 61067 | 94487054 | glycoprotein |
| Variola virus strain Kuwait 1967 (K1629) | Orthopoxvirus | 2237 | Complement binding (secreted) | 604 | VARV-KWT67-015 | 61105 | 94487093 | secreted protein |
| Variola virus strain Kuwait 1967 (K1629) | Orthopoxvirus | 2237 | Complement control/CD46/EEV | 591 | VARV-KWT67-178 | 61268 | 94487256 | glycoprotein |
| Variola virus strain Nepal 1973 V73-175 | Orthopoxvirus | 2221 | Complement binding (secreted) | 604 | VARV-NPL73-015 | 57805 | 109725684 | secreted protein |
| Variola virus strain Nepal 1973 V73-175 | Orthopoxvirus | 2221 | Complement control/CD46/EEV | 591 | VARV-NPL73-177 | 57967 | 109725846 | glycoprotein |

TABLE 4-continued

Viral Orthologous Clusters V2.0 (VOCs)
complement binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Niger 1969 (001, importation from Nigeria) | Orthopoxvirus | 2222 | Complement binding (secreted) | 604 | VARV-NER69-017 | 58010 | 94487295 | secreted protein |
| Variola virus strain Niger 1969 (001, importation from Nigeria) | Orthopoxvirus | 2222 | Complement control/CD46/EEV | 591 | VARV-NER69-183 | 58176 | 94487460 | glycoprotein |
| Variola virus strain Sierra Leone 1969 (V68-258) | Orthopoxvirus | 2223 | Complement binding (secreted) | 604 | VARV-SLE68-017 | 58219 | 94487904 | secreted protein |
| Variola virus strain Sierra Leone 1969 (V68-258) | Orthopoxvirus | 2223 | Complement control/CD46/EEV | 591 | VARV-SLE68-182 | 58384 | 94488068 | glycoprotein |
| Variola virus strain Somalia 1977 (V77-1252) | Orthopoxvirus | 2218 | Complement binding (secreted) | 604 | VARV-SOM77_1252-015 | 57203 | 94488107 | secreted protein |
| Variola virus strain Somalia 1977 (V77-1252) | Orthopoxvirus | 2218 | Complement control/CD46/EEV | 591 | VARV-SOM77_1252-178 | 57366 | 94488270 | glycoprotein |
| Variola virus strain Somalia 1977 (V77-1605) | Orthopoxvirus | 2219 | Complement binding (secreted) | 604 | VARV-SOM77_1605-015 | 57403 | 94488307 | secreted protein |
| Variola virus strain Somalia 1977 (V77-1605) | Orthopoxvirus | 2219 | Complement control/CD46/EEV | 591 | VARV-SOM77_1605-178 | 57566 | 94488470 | glycoprotein |
| Variola virus strain Somalia 1977 V77-2479 | Orthopoxvirus | 2220 | Complement binding (secreted) | 604 | VARV-SOM77_ali-015 | 57603 | 109726091 | secreted protein |
| Variola virus strain Somalia 1977 V77-2479 | Orthopoxvirus | 2220 | Complement control/CD46/EEV | 591 | VARV-SOM77_ali-178 | 57766 | 109726254 | glycoprotein |
| Variola virus strain South Africa 1965 (102 Natal, Ingwavuma) | Orthopoxvirus | 2210 | Complement binding (secreted) | 604 | VARV-ZAF65_102-015 | 55587 | 94487499 | secreted protein |
| Variola virus strain South Africa 1965 (102 Natal, Ingwavuma) | Orthopoxvirus | 2210 | Complement control/CD46/EEV | 591 | VARV-ZAF65_102-178 | 55750 | 94487662 | glycoprotein |
| Variola virus strain South Africa 1965 (103 Tvaal, Nelspruit) | Orthopoxvirus | 2211 | Complement binding (secreted) | 604 | VARV-ZAF65_103-015 | 55788 | 94487700 | secreted protein |
| Variola virus strain South Africa 1965 (103 Tvaal, Nelspruit) | Orthopoxvirus | 2211 | Complement control/CD46/EEV | 591 | VARV-ZAF65_103-178 | 55951 | 94487863 | glycoprotein |
| Variola virus strain Sudan 1947 (Juba) | Orthopoxvirus | 2212 | Complement binding (secreted) | 604 | VARV-SDN47_jub-015 | 55989 | 94488507 | secreted protein |
| Variola virus strain Sudan 1947 (Juba) | Orthopoxvirus | 2212 | Complement control/CD46/EEV | 591 | VARV-SDN47_jub-178 | 56152 | 94488670 | EEV membrane glycoprotein |
| Variola virus strain Sudan 1947 (Rumbec) | Orthopoxvirus | 2213 | Complement binding (secreted) | 604 | VARV-SDN47_rum-015 | 56189 | 94488708 | secreted protein |
| Variola virus strain Sudan 1947 (Rumbec) | Orthopoxvirus | 2213 | Complement control/CD46/EEV | 591 | VARV-SDN47_rum-178 | 56352 | 94488871 | glycoprotein |
| Variola virus strain Sumatra 1970 V70-222 | Orthopoxvirus | 2208 | Complement binding (secreted) | 604 | VARV-SUM70_222-015 | 55185 | 109726294 | secreted protein |
| Variola virus strain Sumatra 1970 V70-222 | Orthopoxvirus | 2208 | Complement control/CD46/EEV | 591 | VARV-SUM70_222-177 | 55347 | 109726456 | glycoprotein |
| Variola virus strain Sumatra 1970 V70-228 | Orthopoxvirus | 2209 | Complement binding (secreted) | 604 | VARV-SUM70_228-015 | 55387 | 94488909 | secreted protein |
| Variola virus strain Sumatra 1970 V70-228 | Orthopoxvirus | 2209 | Complement control/CD46/EEV | 591 | VARV-SUM70_228-177 | 55549 | 94489071 | glycoprotein |
| Variola virus strain Syria 1972 V72-199 | Orthopoxvirus | 2206 | Complement binding (secreted) | 604 | VARV-SYR72-015 | 54781 | 109726497 | secreted protein |
| Variola virus strain Syria 1972 V72-199 | Orthopoxvirus | 2206 | Complement control/CD46/EEV | 591 | VARV-SYR72-178 | 54944 | 109726660 | glycoprotein |
| Variola virus strain Tanzania 1965 kembula | Orthopoxvirus | 2207 | Complement binding (secreted) | 604 | VARV-TZA65-015 | 54984 | 94489109 | secreted protein |
| Variola virus strain Tanzania 1965 kembula | Orthopoxvirus | 2207 | Complement control/CD46/EEV | 591 | VARV-TZA65-178 | 55147 | 94489271 | glycoprotein |

TABLE 4-continued

Viral Orthologous Clusters V2.0 (VOCs)
complement binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain United Kingdom 1946 Harvey | Orthopoxvirus | 2204 | Complement binding (secreted) | 604 | VARV-GBR44_harv-015 | 54380 | 94489308 | secreted protein |
| Variola virus strain United Kingdom 1946 Harvey | Orthopoxvirus | 2204 | Complement control/CD46/EEV | 591 | VARV-GBR44_harv-179 | 54544 | 94489472 | glycoprotein |
| Variola virus strain United Kingdom 1946 Hinden (Middlesex) | Orthopoxvirus | 2205 | Complement binding (secreted) | 604 | VARV-GBR46_hind-015 | 54582 | 94489511 | secreted protein |
| Variola virus strain United Kingdom 1946 Hinden (Middlesex) | Orthopoxvirus | 2205 | Complement control/CD46/EEV | 591 | VARV-GBR46_hind-178 | 54745 | 94489674 | glycoprotein |
| Variola virus strain United Kingdom 1947 Higgins (Staffordshire) | Orthopoxvirus | 2202 | Complement binding (secreted) | 604 | VARV-GBR47_hig-015 | 53974 | 94489710 | secreted protein |
| Variola virus strain United Kingdom 1947 Higgins (Staffordshire) | Orthopoxvirus | 2202 | Complement control/CD46/EEV | 591 | VARV-GBR47_hig-178 | 54137 | 94489873 | glycoprotein |
| Variola virus strain United Kingdom 1952 Butler | Orthopoxvirus | 2200 | Complement binding (secreted) | 604 | VARV-GBR52_but-019 | 53767 | 94489915 | secreted protein |
| Variola virus strain United Kingdom 1952 Butler | Orthopoxvirus | 2200 | Complement control/CD46/EEV | 591 | VARV-GBR52_but-185 | 53933 | 94490080 | glycoprotein |
| Variola virus strain Yugoslavia 1972 V72-164 | Orthopoxvirus | 2196 | Complement binding (secreted) | 604 | VARV-YUG72-015 | 53158 | 94490119 | secreted protein |
| Variola virus strain Yugoslavia 1972 V72-164 | Orthopoxvirus | 2196 | Complement control/CD46/EEV | 591 | VARV-YUG72-178 | 53321 | 94490282 | glycoprotein |
| Yaba monkey tumor virus strain Amano | Yatapoxvirus | 1503 | Complement control/CD46/EEV | 591 | YMTV-Amano-133 | 43182 | 38229302 | 144R |
| Yaba-like Disease Virus strain Davis | Yatapoxvirus | 1487 | Complement control/CD46/EEV | 591 | YLDV-Davis-147 | 40196 | 12085127 | 144R |

TABLE 5

Viral Orthologous Clusters V2.0 (VOCs)
IL-1beta
Gene Results Table

| Genome name | Genus | Genome id | Ortholog Group Name | Ortholog Group ID | Gene number | Gene id | Genbank id | Genbank name |
|---|---|---|---|---|---|---|---|---|
| Camelpox virus strain CMS | Orthopoxvirus | 1493 | IL-1 beta receptor | 648 | CMLV-CMS-243 | 41339 | 19718172 | 190.5aR |
| Camelpox virus strain CMS | Orthopoxvirus | 1493 | IL-1 beta receptor | 648 | CMLV-CMS-244 | 41340 | 19718171 | 190R |
| Camelpox virus strain CMS | Orthopoxvirus | 1493 | IL-1 beta receptor | 648 | CMLV-CMS-246 | 41342 | 19718174 | 191R |
| Camelpox virus strain M96 | Orthopoxvirus | 1491 | IL-1 beta receptor | 648 | CMLV-M96-195 | 40901 | 18640427 | 193 |
| Camelpox virus strain M96 | Orthopoxvirus | 1491 | IL-1 beta receptor | 648 | CMLV-M96-196 | 40902 | 18640428 | 194 |
| Camelpox virus strain M96 | Orthopoxvirus | 1491 | IL-1 beta receptor | 648 | CMLV-M96-198 | 40904 | 18640430 | 196 |
| Cowpox virus strain Brighton Red | Orthopoxvirus | 1496 | IL-1 beta receptor | 648 | CPXV-BR-215 | 41914 | 20178569 | 209 |
| Cowpox virus strain GRI-90 | Orthopoxvirus | 1501 | IL-1 beta receptor | 648 | CPXV-GRI-197 | 42854 | 30519565 | B14R |
| Cowpox virus strain Germany 91-3 | Orthopoxvirus | 2214 | IL-1 beta receptor | 648 | CPXV-GER91-197 | 56572 | 90660430 | IL-1-beta-inhibitor |
| Ectromelia virus strain Moscow | Orthopoxvirus | 1492 | IL-1 beta receptor | 648 | ECTV-Mos-168 | 41087 | 22164598 | 163 |
| Ectromelia virus strain Naval | Orthopoxvirus | 1499 | IL-1 beta receptor | 648 | ECTV-Nav-173 | 42428 | 0 | 191 |
| Horsepox virus strain MNR-76 | Orthopoxvirus | 2230 | IL-1 beta receptor | 648 | HSPV-MNR76-218 | 59855 | 111184385 | HSPV192 |
| Monkeypox virus strain Congo__2003__358 | Orthopoxvirus | 1524 | IL-1 beta receptor | 648 | MPXV-COG__2003__358-182 | 47241 | 68449058 | 189 |
| Monkeypox virus strain Liberia__1970__184 | Orthopoxvirus | 1525 | IL-1 beta receptor | 648 | MPXV-LBR__1970__184-182 | 47441 | 68449462 | 189 |
| Monkeypox virus strain Liberia__1970__184 | Orthopoxvirus | 1525 | IL-1 beta receptor | 648 | MPXV-LBR__1970__184-183 | 47442 | 68449463 | 189.5 |
| Monkeypox virus strain USA__2003__039 | Orthopoxvirus | 1526 | IL-1 beta receptor | 648 | MPXV-USA__2003__039-182 | 47639 | 68449661 | 189 |
| Monkeypox virus strain USA__2003__039 | Orthopoxvirus | 1526 | IL-1 beta receptor | 648 | MPXV-USA__2003__039-183 | 47640 | 68449662 | 189.5 |
| Monkeypox virus strain USA__2003__044 | Orthopoxvirus | 1522 | IL-1 beta receptor | 648 | MPXV-USA__2003__044-182 | 46841 | 68448859 | 189 |
| Monkeypox virus strain USA__2003__044 | Orthopoxvirus | 1522 | IL-1 beta receptor | 648 | MPXV-USA__2003__044-183 | 46842 | 68448860 | 189.5 |
| Monkeypox virus strain Zaire | Orthopoxvirus | 1489 | IL-1 beta receptor | 648 | MPXV-ZAR-178 | 40539 | 17975088 | B14R |
| Monkeypox virus strain Zaire__1979-005 | Orthopoxvirus | 1523 | IL-1 beta receptor | 648 | MPXV-ZAR__1979__005-183 | 47040 | 68449260 | 189 |
| Monkeypox virus strain Zaire__1979-005 | Orthopoxvirus | 1523 | IL-1 beta receptor | 648 | MPXV-ZAR__1979__005-184 | 47041 | 68449261 | 189.5 |

TABLE 5-continued

Viral Orthologous Clusters V2.0 (VOCs)
IL-1beta
Gene Results Table

| Genome name | Genus | Genome id | Ortholog Group Name | Ortholog Group ID | Gene number | Gene id | Genbank id | Genbank name |
|---|---|---|---|---|---|---|---|---|
| Taterapox virus strain Dahomey 1968 | Orthopoxvirus | 2195 | IL-1 beta receptor | 648 | TATV-DAH68-203 | 53121 | 113195380 | IL-1-beta-inhibitor |
| Vaccinia virus strain 3737 | Orthopoxvirus | 1528 | IL-1 beta receptor | 648 | VACV-3737-199 | 47987 | 88900813 | 185 |
| Vaccinia virus strain Acambis 2000 | Orthopoxvirus | 2161 | IL-1 beta receptor | 648 | VACV-Acam2000-207 | 51263 | 38349065 | 209 |
| Vaccinia virus strain Acambis 3 | Orthopoxvirus | 2162 | IL-1 beta receptor | 648 | VACV-Acam3-209 | 51500 | 37551643 | 209 |
| Vaccinia virus strain Acambis 3000 Modified Virus Ankara | Orthopoxvirus | 1510 | IL-1 beta receptor | 648 | VACV-Acam3000-186 | 44500 | 47088510 | 184 |
| Vaccinia virus strain Copenhagen | Orthopoxvirus | 1485 | IL-1 beta receptor | 648 | VACV-Cop-250 | 39775 | 335562 | B16R |
| Vaccinia virus strain Copenhagen | Orthopoxvirus | 1485 | IL-1 beta receptor | 648 | VACV-Cop-272 | 62885 | 0 | |
| Vaccinia virus strain DUKE | Orthopoxvirus | 2458 | IL-1 beta receptor | 648 | VACV-DUKE-207 | 63587 | 90819859 | 207 |
| Vaccinia virus strain LC16m8 | Orthopoxvirus | 1517 | IL-1 beta receptor | 648 | VACV-LC16m8-265 | 45718 | 56713604 | m8255R |
| Vaccinia virus strain LC16mO | Orthopoxvirus | 1518 | IL-1 beta receptor | 648 | VACV-LC16mO-265 | 46002 | 56713888 | mO255R |
| Vaccinia virus strain Lister | Orthopoxvirus | 1519 | IL-1 beta receptor | 648 | VACV-Lister-265 | 46286 | 0 | m8255R |
| Vaccinia virus strain Lister_VACV107 | Orthopoxvirus | 2659 | IL-1 beta receptor | 648 | VACV-Lister_VACV107-196 | 64529 | 88854278 | List192 |
| Vaccinia virus strain MVA-I721 | Orthopoxvirus | 2696 | IL-1 beta receptor | 648 | VACV-MVA_I721-073 | 65287 | 0 | 184 |
| Vaccinia virus strain Western Reserve | Orthopoxvirus | 1500 | IL-1 beta receptor | 648 | VACV-WR-197 | 42636 | 66275994 | 197 |
| Vaccinia virus strain modified vaccinia Ankara | Orthopoxvirus | 1484 | IL-1 beta receptor | 648 | VACV-MVA-159 | 65571 | 2772816 | MVA184R |
| Variola minor virus strain Garcia 1966 | Orthopoxvirus | 1482 | IL-1 beta receptor | 648 | VARV-Gar_1966-194 | 39147 | 5830746 | D4R |
| Variola minor virus strain Garcia 1966 | Orthopoxvirus | 1482 | IL-1 beta receptor | 648 | VARV-Gar_1966-196 | 39149 | 5830748 | D6R |
| Variola virus strain Afghanistan 1970 Variolator 4 | Orthopoxvirus | 2197 | IL-1 beta receptor | 648 | VARV-AFG70-187 | 53531 | 109724226 | IL-1-beta-inhibitor |
| Variola virus strain Afghanistan 1970 Variolator 4 | Orthopoxvirus | 2197 | IL-1 beta receptor | 648 | VARV-AFG70-189 | 53533 | 109724228 | IL-1-beta-inhibitor |
| Variola virus strain Afghanistan 1970 Variolator 4 | Orthopoxvirus | 2197 | IL-1 beta receptor | 648 | VARV-AFG70-190 | 53534 | 109724229 | IL-1-beta-inhibitor |
| Variola virus strain Bangladesh 1974 (Shahzaman) | Orthopoxvirus | 2216 | IL-1 beta receptor | 648 | VARV-BGD74_shz-186 | 56978 | 94484843 | IL-1-beta-inhibitor |
| Variola virus strain Bangladesh 1974 (Solaiman) | Orthopoxvirus | 2217 | IL-1 beta receptor | 648 | VARV-BGD74_sol-186 | 57176 | 94485041 | IL-1-beta-inhibitor |
| Variola virus strain Bangladesh 1974 (nur islam) | Orthopoxvirus | 2215 | IL-1 beta receptor | 648 | VARV-BGD74_nur-186 | 56780 | 94484645 | IL-1-beta-inhibitor |

TABLE 5-continued

Viral Orthologous Clusters V2.0 (VOCs)
IL-1beta
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Bangladesh 1975 v75-550 Banu | Orthopoxvirus | 2198 | IL-1 beta receptor | 648 | VARV-BGD75_Banu-186 | 53733 | 109724429 | IL-1-beta-inhibitor |
| Variola virus strain Bangladesh 1975 v75-550 Banu | Orthopoxvirus | 2198 | IL-1 beta receptor | 648 | VARV-BGD75_Banu-188 | 53735 | 109724431 | IL-1-beta-inhibitor |
| Variola virus strain Bangladesh 1975 v75-550 Banu | Orthopoxvirus | 2198 | IL-1 beta receptor | 648 | VARV-BGD75_Banu-189 | 53736 | 109724432 | IL-1-beta-inhibitor |
| Variola virus strain Benin, Dahomey 1968 (v68-59) | Orthopoxvirus | 2224 | IL-1 beta receptor | 648 | VARV-BEN68-194 | 58604 | 94483831 | IL-1-beta-inhibitor |
| Variola virus strain Benin, Dahomey 1968 (v68-59) | Orthopoxvirus | 2224 | IL-1 beta receptor | 648 | VARV-BEN68-195 | 58605 | 94483832 | IL-1-beta-inhibitor |
| Variola virus strain Botswana 1972 (v72-143) | Orthopoxvirus | 2225 | IL-1 beta receptor | 648 | VARV-BWA72-187 | 58806 | 94484034 | IL-1-beta-inhibitor |
| Variola virus strain Botswana 1972 (v72-143) | Orthopoxvirus | 2225 | IL-1 beta receptor | 648 | VARV-BWA72-188 | 58807 | 94484035 | IL-1-beta-inhibitor |
| Variola virus strain Botswana 1973 (v73-225) | Orthopoxvirus | 2226 | IL-1 beta receptor | 648 | VARV-BWA73-187 | 59008 | 94484237 | IL-1-beta-inhibitor |
| Variola virus strain Botswana 1973 (v73-225) | Orthopoxvirus | 2226 | IL-1 beta receptor | 648 | VARV-BWA73-188 | 59009 | 94484238 | IL-1-beta-inhibitor |
| Variola virus strain Brazil 1966 (v66-39 Sao Paulo) | Orthopoxvirus | 2227 | IL-1 beta receptor | 648 | VARV-BRA66-196 | 59219 | 94484444 | IL-1-beta-inhibitor |
| Variola virus strain Brazil 1966 (v66-39 Sao Paulo) | Orthopoxvirus | 2227 | IL-1 beta receptor | 648 | VARV-BRA66-197 | 59220 | 94484445 | IL-1-beta-inhibitor |
| Variola virus strain China Horn 1948 Sabin Lab July 1948 | Orthopoxvirus | 2203 | IL-1 beta receptor | 648 | VARV-CHN48-188 | 54348 | 109724632 | IL-1-beta-inhibitor |
| Variola virus strain China Horn 1948 Sabin Lab July 1948 | Orthopoxvirus | 2203 | IL-1 beta receptor | 648 | VARV-CHN48-190 | 54350 | 109724634 | IL-1-beta-inhibitor |
| Variola virus strain China Horn 1948 Sabin Lab July 1948 | Orthopoxvirus | 2203 | IL-1 beta receptor | 648 | VARV-CHN48-191 | 54351 | 109724635 | IL-1-beta-inhibitor |
| Variola virus strain Congo 1970 v70-46 Kinshasa | Orthopoxvirus | 2229 | IL-1 beta receptor | 648 | VARV-COG70_46-186 | 59621 | 109724837 | IL-1-beta-inhibitor |
| Variola virus strain Congo 1970 v70-46 Kinshasa | Orthopoxvirus | 2229 | IL-1 beta receptor | 648 | VARV-COG70_46-188 | 59623 | 109724839 | IL-1-beta-inhibitor |
| Variola virus strain Congo 1970 v70-46 Kinshasa | Orthopoxvirus | 2229 | IL-1 beta receptor | 648 | VARV-COG70_46-189 | 59624 | 109724840 | IL-1-beta-inhibitor |
| Variola virus strain Congo 9 1970 (v74-227 Gispen) | Orthopoxvirus | 2228 | IL-1 beta receptor | 648 | VARV-COG70_227-187 | 59421 | 94485240 | IL-1-beta-inhibitor |
| Variola virus strain Congo 9 1970 (v74-227 Gispen) | Orthopoxvirus | 2228 | IL-1 beta receptor | 648 | VARV-COG70_227-188 | 59422 | 94485241 | IL-1-beta-inhibitor |
| Variola virus strain Ethiopia 1972 (Eth16 R14-1X-72 Addis) | Orthopoxvirus | 2231 | IL-1 beta receptor | 648 | VARV-ETH72_16-188 | 60061 | 94485442 | IL-1-beta-inhibitor |
| Variola virus strain Ethiopia 1972 (Eth16 R14-1X-72 Addis) | Orthopoxvirus | 2231 | IL-1 beta receptor | 648 | VARV-ETH72_16-189 | 60062 | 94485443 | IL-1-beta-inhibitor |
| Variola virus strain Ethiopia 1972 (Eth16 R14-1X-72 Addis) | Orthopoxvirus | 2231 | IL-1 beta receptor | 648 | VARV-ETH72_16-190 | 60063 | 94485444 | IL-1-beta-inhibitor |
| Variola virus strain Ethiopia 1972 (Eth17 R14-1X-72 Addis) | Orthopoxvirus | 2232 | IL-1 beta receptor | 648 | VARV-ETH72_17-188 | 60264 | 94485645 | IL-1-beta-inhibitor |

TABLE 5-continued

Viral Orthologous Clusters V2.0 (VOCs)
IL-1beta
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Germany 1958 Heidelberg | Orthopoxvirus | 2233 | IL-1 beta receptor | 648 | VARV-DEU58-186 | 60463 | 109725040 | IL-1-beta-inhibitor |
| Variola virus strain Germany 1958 Heidelberg | Orthopoxvirus | 2233 | IL-1 beta receptor | 648 | VARV-DEU58-188 | 60465 | 109725042 | IL-1-beta-inhibitor |
| Variola virus strain Guinea 1969 (005) | Orthopoxvirus | 2234 | IL-1 beta receptor | 648 | VARV-GIN69-192 | 60670 | 94485847 | IL-1-beta-inhibitor |
| Variola virus strain Guinea 1969 (005) | Orthopoxvirus | 2234 | IL-1 beta receptor | 648 | VARV-GIN69-193 | 60671 | 94485848 | IL-1-beta-inhibitor |
| Variola virus strain India 1953 (Kali-Muthu-M50 Madras) | Orthopoxvirus | 2238 | IL-1 beta receptor | 648 | VARV-IND53_mad-188 | 61478 | 94486051 | IL-1-beta-inhibitor |
| Variola virus strain India 1953 (New Delhi) | Orthopoxvirus | 2239 | IL-1 beta receptor | 648 | VARV-IND53_ndel-187 | 61678 | 94486252 | IL-1-beta-inhibitor |
| Variola virus strain India 1953 (New Delhi) | Orthopoxvirus | 2239 | IL-1 beta receptor | 648 | VARV-IND53_ndel-188 | 61679 | 94486253 | IL-1-beta-inhibitor |
| Variola virus strain India 1964 7124 Vellore | Orthopoxvirus | 2240 | IL-1 beta receptor | 648 | VARV-IND64_vel4-189 | 61882 | 109725245 | IL-1-beta-inhibitor |
| Variola virus strain India 1964 7124 Vellore | Orthopoxvirus | 2240 | IL-1 beta receptor | 648 | VARV-IND64_vel4-191 | 61884 | 109725247 | IL-1-beta-inhibitor |
| Variola virus strain India 1964 7124 Vellore | Orthopoxvirus | 2240 | IL-1 beta receptor | 648 | VARV-IND64_vel4-192 | 61885 | 109725248 | IL-1-beta-inhibitor |
| Variola virus strain India 1964 7125 Vellore | Orthopoxvirus | 2241 | IL-1 beta receptor | 648 | VARV-IND64_vel5-188 | 62086 | 109725450 | IL-1-beta-inhibitor |
| Variola virus strain India 1964 7125 Vellore | Orthopoxvirus | 2241 | IL-1 beta receptor | 648 | VARV-IND64_vel5-190 | 62088 | 109725452 | IL-1-beta-inhibitor |
| Variola virus strain India 1964 7125 Vellore | Orthopoxvirus | 2241 | IL-1 beta receptor | 648 | VARV-IND64_vel5-191 | 62089 | 109725453 | IL-1-beta-inhibitor |
| Variola virus strain India 3 Major 1967 | Orthopoxvirus | 1483 | IL-1 beta receptor | 648 | VARV-IND3_1967-186 | 39348 | 9627704 | B15R |
| Variola virus strain India 3 Major 1967 | Orthopoxvirus | 1483 | IL-1 beta receptor | 648 | VARV-IND3_1967-188 | 39350 | 9627706 | B17R |
| Variola virus strain Iran 1972 2602 Tabriz | Orthopoxvirus | 2235 | IL-1 beta receptor | 648 | VARV-IRN72-187 | 60872 | 109725652 | IL-1-beta-inhibitor |
| Variola virus strain Iran 1972 2602 Tabriz | Orthopoxvirus | 2235 | IL-1 beta receptor | 648 | VARV-IRN72-189 | 60874 | 109725654 | IL-1-beta-inhibitor |
| Variola virus strain Iran 1972 2602 Tabriz | Orthopoxvirus | 2235 | IL-1 beta receptor | 648 | VARV-IRN72-190 | 60875 | 109725655 | IL-1-beta-inhibitor |
| Variola virus strain Japan 1946 (Yamada MS-2(A) Tokyo) | Orthopoxvirus | 2243 | IL-1 beta receptor | 648 | VARV-JPN46_yam-187 | 62462 | 94486455 | IL-1-beta-inhibitor |
| Variola virus strain Japan 1946 (Yamada MS-2(A) Tokyo) | Orthopoxvirus | 2243 | IL-1 beta receptor | 648 | VARV-JPN46_yam-188 | 62463 | 94486456 | IL-1-beta-inhibitor |
| Variola virus strain Japan 1951 (Harper, Masterseed) | Orthopoxvirus | 2244 | IL-1 beta receptor | 648 | VARV-JPN51_hrpr-187 | 62664 | 94486658 | IL-1-beta-inhibitor |
| Variola virus strain Japan 1951 (Stillwell, Masterseed) | Orthopoxvirus | 2245 | IL-1 beta receptor | 648 | VARV-JPN51_stwl-187 | 62865 | 94486860 | IL-1-beta-inhibitor |
| Variola virus strain Japan 1951 (Stillwell, Masterseed) | Orthopoxvirus | 2245 | IL-1 beta receptor | 648 | VARV-JPN51_stwl-188 | 62866 | 94486861 | IL-1-beta-inhibitor |

TABLE 5-continued

Viral Orthologous Clusters V2.0 (VOCs)
IL-1beta
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Korea 1947 (Lee, Masterseed) | Orthopoxvirus | 2236 | IL-1 beta receptor | 648 | VARV-KOR47-188 | 61076 | 94487063 | IL-1-beta-inhibitor |
| Variola virus strain Korea 1947 (Lee, Masterseed) | Orthopoxvirus | 2236 | IL-1 beta receptor | 648 | VARV-KOR47-189 | 61077 | 94487064 | IL-1-beta-inhibitor |
| Variola virus strain Kuwait 1967 (K1629) | Orthopoxvirus | 2237 | IL-1 beta receptor | 648 | VARV-KWT67-187 | 61277 | 94487265 | IL-1-beta-inhibitor |
| Variola virus strain Kuwait 1967 (K1629) | Orthopoxvirus | 2237 | IL-1 beta receptor | 648 | VARV-KWT67-188 | 61278 | 94487266 | IL-1-beta-inhibitor |
| Variola virus strain Nepal 1973 V73-175 | Orthopoxvirus | 2221 | IL-1 beta receptor | 648 | VARV-NPL73-186 | 57976 | 109725854 | IL-1-beta-inhibitor |
| Variola virus strain Nepal 1973 V73-175 | Orthopoxvirus | 2221 | IL-1 beta receptor | 648 | VARV-NPL73-188 | 57978 | 109725856 | IL-1-beta-inhibitor |
| Variola virus strain Nepal 1973 V73-175 | Orthopoxvirus | 2221 | IL-1 beta receptor | 648 | VARV-NPL73-189 | 57979 | 109725857 | IL-1-beta-inhibitor |
| Variola virus strain Niger 1969 (001, importation from Nigeria) | Orthopoxvirus | 2222 | IL-1 beta receptor | 648 | VARV-NER69-194 | 58187 | 94487468 | IL-1-beta-inhibitor |
| Variola virus strain Niger 1969 (001, importation from Nigeria) | Orthopoxvirus | 2222 | IL-1 beta receptor | 648 | VARV-NER69-195 | 58188 | 94487469 | IL-1-beta-inhibitor |
| Variola virus strain Sierra Leone 1969 (V68-258) | Orthopoxvirus | 2223 | IL-1 beta receptor | 648 | VARV-SLE68-193 | 58395 | 94488076 | IL-1-beta-inhibitor |
| Variola virus strain Sierra Leone 1969 (V68-258) | Orthopoxvirus | 2223 | IL-1 beta receptor | 648 | VARV-SLE68-194 | 58396 | 94488077 | IL-1-beta-inhibitor |
| Variola virus strain Somalia 1977 (V77-1252) | Orthopoxvirus | 2218 | IL-1 beta receptor | 648 | VARV-SOM77_1252-186 | 57374 | 94488278 | IL-1-beta-inhibitor |
| Variola virus strain Somalia 1977 (V77-1252) | Orthopoxvirus | 2218 | IL-1 beta receptor | 648 | VARV-SOM77_1252-187 | 57375 | 94488279 | IL-1-beta-inhibitor |
| Variola virus strain Somalia 1977 (V77-1605) | Orthopoxvirus | 2219 | IL-1 beta receptor | 648 | VARV-SOM77_1605-186 | 57574 | 94488478 | IL-1-beta-inhibitor |
| Variola virus strain Somalia 1977 (V77-1605) | Orthopoxvirus | 2219 | IL-1 beta receptor | 648 | VARV-SOM77_1605-187 | 57575 | 94488479 | IL-1-beta-inhibitor |
| Variola virus strain Somalia 1977 V77-2479 | Orthopoxvirus | 2220 | IL-1 beta receptor | 648 | VARV-SOM77_ali-186 | 57774 | 109726262 | IL-1-beta-inhibitor |
| Variola virus strain Somalia 1977 V77-2479 | Orthopoxvirus | 2220 | IL-1 beta receptor | 648 | VARV-SOM77_ali-188 | 57776 | 109726264 | IL-1-beta-inhibitor |
| Variola virus strain Somalia 1977 V77-2479 | Orthopoxvirus | 2220 | IL-1 beta receptor | 648 | VARV-SOM77_ali-189 | 57777 | 109726265 | IL-1-beta-inhibitor |
| Variola virus strain South Africa 1965 (102 Natal, Ingwavuma) | Orthopoxvirus | 2210 | IL-1 beta receptor | 648 | VARV-ZAF65_102-187 | 55759 | 94487671 | IL-1-beta-inhibitor |
| Variola virus strain South Africa 1965 (102 Natal, Ingwavuma) | Orthopoxvirus | 2210 | IL-1 beta receptor | 648 | VARV-ZAF65_102-188 | 55760 | 94487672 | IL-1-beta-inhibitor |
| Variola virus strain South Africa 1965 (103 Tvaal, Nelspruit) | Orthopoxvirus | 2211 | IL-1 beta receptor | 648 | VARV-ZAF65_103-187 | 55960 | 94487872 | IL-1-beta-inhibitor |
| Variola virus strain South Africa 1965 (103 Tvaal, Nelspruit) | Orthopoxvirus | 2211 | IL-1 beta receptor | 648 | VARV-ZAF65_103-188 | 55961 | 94487873 | IL-1-beta-inhibitor |
| Variola virus strain Sudan 1947 (Juba) | Orthopoxvirus | 2212 | IL-1 beta receptor | 648 | VARV-SDN47_jub-187 | 56161 | 94488679 | IL-1-beta-inhibitor |

TABLE 5-continued

Viral Orthologous Clusters V2.0 (VOCs)
IL-1beta
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Sudan 1947 (Rumbec) | Orthopoxvirus | 2213 | IL-1 beta receptor | 648 | VARV-SDN47_num-187 | 56361 | 94488880 | IL-1-beta-inhibitor |
| Variola virus strain Sudan 1947 (Rumbec) | Orthopoxvirus | 2213 | IL-1 beta receptor | 648 | VARV-SDN47_num-188 | 56362 | 94488881 | IL-1-beta-inhibitor |
| Variola virus strain Sumatra 1970 V70-222 | Orthopoxvirus | 2208 | IL-1 beta receptor | 648 | VARV-SUM70_222-186 | 55356 | 109726465 | IL-1-beta-inhibitor |
| Variola virus strain Sumatra 1970 V70-222 | Orthopoxvirus | 2208 | IL-1 beta receptor | 648 | VARV-SUM70_222-188 | 55358 | 109726467 | IL-1-beta-inhibitor |
| Variola virus strain Sumatra 1970 V70-222 | Orthopoxvirus | 2208 | IL-1 beta receptor | 648 | VARV-SUM70_222-189 | 55359 | 109726468 | IL-1-beta-inhibitor |
| Variola virus strain Sumatra 1970 V70-228 | Orthopoxvirus | 2209 | IL-1 beta receptor | 648 | VARV-SUM70_228-186 | 55558 | 94489080 | IL-1-beta-inhibitor |
| Variola virus strain Sumatra 1970 V70-228 | Orthopoxvirus | 2209 | IL-1 beta receptor | 648 | VARV-SUM70_228-187 | 55559 | 94489081 | IL-1-beta-inhibitor |
| Variola virus strain Syria 1972 V72-199 | Orthopoxvirus | 2206 | IL-1 beta receptor | 648 | VARV-SYR72-187 | 54953 | 109726669 | IL-1-beta-inhibitor |
| Variola virus strain Syria 1972 V72-199 | Orthopoxvirus | 2206 | IL-1 beta receptor | 648 | VARV-SYR72-189 | 54955 | 109726671 | IL-1-beta-inhibitor |
| Variola virus strain Syria 1972 V72-199 | Orthopoxvirus | 2206 | IL-1 beta receptor | 648 | VARV-SYR72-190 | 54956 | 109726672 | IL-1-beta-inhibitor |
| Variola virus strain Tanzania 1965 kembula | Orthopoxvirus | 2207 | IL-1 beta receptor | 648 | VARV-TZA65-187 | 55156 | 94489278 | IL-1-beta-inhibitor |
| Variola virus strain Tanzania 1965 kembula | Orthopoxvirus | 2207 | IL-1 beta receptor | 648 | VARV-TZA65-188 | 55157 | 94489279 | IL-1-beta-inhibitor |
| Variola virus strain United Kingdom 1946 Harvey | Orthopoxvirus | 2204 | IL-1 beta receptor | 648 | VARV-GBR44_harv-188 | 54553 | 94489481 | IL-1-beta-inhibitor |
| Variola virus strain United Kingdom 1946 Harvey | Orthopoxvirus | 2204 | IL-1 beta receptor | 648 | VARV-GBR44_harv-189 | 54554 | 94489482 | IL-1-beta-inhibitor |
| Variola virus strain United Kingdom 1946 Hinden (Middlesex) | Orthopoxvirus | 2205 | IL-1 beta receptor | 648 | VARV-GBR46_hind-187 | 54754 | 94489683 | IL-1-beta-inhibitor |
| Variola virus strain United Kingdom 1947 Higgins (Staffordshire) | Orthopoxvirus | 2202 | IL-1 beta receptor | 648 | VARV-GBR47_hig-187 | 54146 | 94489881 | IL-1-beta-inhibitor |
| Variola virus strain United Kingdom 1947 Higgins (Staffordshire) | Orthopoxvirus | 2202 | IL-1 beta receptor | 648 | VARV-GBR47_hig-188 | 54147 | 94489882 | IL-1-beta-inhibitor |
| Variola virus strain United Kingdom 1952 Butler | Orthopoxvirus | 2200 | IL-1 beta receptor | 648 | VARV-GBR52_but-196 | 53944 | 94490088 | IL-1-beta-inhibitor |
| Variola virus strain United Kingdom 1952 Butler | Orthopoxvirus | 2200 | IL-1 beta receptor | 648 | VARV-GBR52_but-197 | 53945 | 94490089 | IL-1-beta-inhibitor |
| Variola virus strain Yugoslavia 1972 V72-164 | Orthopoxvirus | 2196 | IL-1 beta receptor | 648 | VARV-YUG72-187 | 53330 | 94490291 | IL-1-beta-inhibitor |
| Variola virus strain Yugoslavia 1972 V72-164 | Orthopoxvirus | 2196 | IL-1 beta receptor | 648 | VARV-YUG72-188 | 53331 | 94490292 | IL-1-beta-inhibitor |

TABLE 6

Viral Orthologous Clusters V2.0 (VOCs)
IL-1 receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Deerpox virus strain W-1170-84 | Unclassified | 1516 | IL-1 receptor (LSDV-N-006) | 735 | DPV-W1170_84-015 | 45298 | 0 | 15 |
| Deerpox virus strain W-848-83 | Unclassified | 1515 | IL-1 receptor (LSDV-N-006) | 735 | DPV-W848_83-015 | 45128 | 62637394 | 15 |
| Goatpox virus strain G20-LKV | Capripoxvirus | 1514 | IL-1 receptor (LSDV-N-006) | 735 | GTPV-G20LKV-004 | 44964 | 0 | 4 |
| Goatpox virus strain Pellor | Capripoxvirus | 1513 | IL-1 receptor (LSDV-N-006) | 735 | GTPV-Pellor-004 | 44814 | 0 | 4 |
| Lumpy skin disease virus strain Neethling 2490 | Capripoxvirus | 1488 | IL-1 receptor (LSDV-N-006) | 735 | LSDV-Nee-006 | 40209 | 15150445 | 6 |
| Lumpy skin disease virus strain Neethling vaccine LW 1959 | Capripoxvirus | 1498 | IL-1 receptor (LSDV-N-006) | 735 | LSDV-LW1959-006 | 42100 | 22595698 | 6 |
| Lumpy skin disease virus strain Neethling Warmbaths LW | Capripoxvirus | 1497 | IL-1 receptor (LSDV-N-006) | 735 | LSDV-NW_LW-006 | 41940 | 22595539 | 6 |
| Sheeppox virus strain A | Capripoxvirus | 1511 | IL-1 receptor (LSDV-N-006) | 735 | SPPV-A-004 | 44513 | 0 | 4 |
| Sheeppox virus strain NISKHI | Capripoxvirus | 1512 | IL-1 receptor (LSDV-N-006) | 735 | SPPV-NISKHI-003 | 44662 | 0 | 4 |
| Sheeppox virus strain TU-V02127 | Capripoxvirus | 1495 | IL-1 receptor (LSDV-N-006) | 735 | SPPV-TU-004 | 41552 | 21492461 | 4 |

TABLE 7

Viral Orthologous Clusters V2.0 (VOCs)
IL-18 binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Canarypox virus strain ATCC VR111 | Avipoxvirus | 1506 | IL-18 BP (Avian) | 312 | CNPV-VR111-100 | 43573 | 40556038 | 100 |
| Cowpox virus strain Brighton Red | Orthopoxvirus | 1496 | IL-18 BP (Bsh-D7L) | 599 | CPXV-BR-024 | 41723 | 20178392 | 24 |
| Cowpox virus strain GRI-90 | Orthopoxvirus | 1501 | IL-18 BP (Bsh-D7L) | 599 | CPXV-GRI-022 | 42679 | 30519420 | C8L |
| Cowpox virus strain Germany 91-3 | Orthopoxvirus | 2214 | IL-18 BP (Bsh-D7L) | 599 | CPXV-GER91-022 | 56397 | 90660255 | interleukin-18-binding protein |
| Deerpox virus strain W-1170-84 | Unclassified | 1516 | IL-18 BP (14L) | 726 | DPV-W1170_84-021 | 45304 | 0 | 21 |
| Deerpox virus strain W-848-83 | Unclassified | 1515 | IL-18 BP (14L) | 726 | DPV-W848_83-021 | 45134 | 62637400 | 21 |
| Ectromelia virus strain Moscow | Orthopoxvirus | 1492 | IL-18 BP (Bsh-D7L) | 599 | ECTV-Mos-014 | 40933 | 22164620 | 13 |
| Ectromelia virus strain Naval | Orthopoxvirus | 1499 | IL-18 BP (Bsh-D7L) | 599 | ECTV-Nav-013 | 42268 | 0 | 19 |
| Fowlpox virus strain HP1-438 Munich | Avipoxvirus | 1509 | IL-18 BP (Avian) | 312 | FWPV-HP1_438-068 | 44141 | 41023361 | fp9.073 |
| Fowlpox virus strain Iowa | Avipoxvirus | 1476 | IL-18 BP (Avian) | 312 | FWPV-Iowa-073 | 37805 | 9634743 | 73 |
| Goatpox virus strain G20-LKV | Capripoxvirus | 1514 | IL-18 BP (14L) | 726 | GTPV-G20LKV-012 | 44972 | 0 | 12 |
| Goatpox virus strain Pellor | Capripoxvirus | 1513 | IL-18 BP (14L) | 726 | GTPV-Pellor-012 | 44822 | 0 | 12 |
| Horsepox virus strain MNR-76 | Orthopoxvirus | 2230 | IL-18 BP (Bsh-D7L) | 599 | HSPV-MNR76-027 | 59664 | 111184194 | HSPV019 |
| Lumpy skin disease virus strain Neethling 2490 | Capripoxvirus | 1488 | IL-18 BP (14L) | 726 | LSDV-Nee-015 | 40218 | 15150454 | 15 |

TABLE 7-continued

Viral Orthologous Clusters V2.0 (VOCs)
IL-18 binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Lumpy skin disease virus strain Neethling Warmbaths LW | Capripoxvirus | 1497 | IL-18 BP (14L) | 726 | LSDV-NW_LW-015 | 41949 | 22595548 | 15 |
| Lumpy skin disease virus strain Neethling vaccine LW 1959 | Capripoxvirus | 1498 | IL-18 BP (14L) | 726 | LSDV-LW1959-015 | 42109 | 22595707 | 15 |
| Molluscum contagiosum virus strain subtype 1 | Molluscipoxvirus | 1477 | IL-18 BP (14L) | 726 | MOCV-st1-055 | 38049 | 9628986 | 054L |
| Monkeypox Virus strain Walter Reed 267 | Orthopoxvirus | 1502 | IL-18 BP (Bsh-D7L) | 599 | MPXV-WR267-009 | 42880 | 0 | 9 |
| Monkeypox virus strain COP-58 | Orthopoxvirus | 1520 | IL-18 BP (Bsh-D7L) | 599 | MPXV-COP58-009 | 46314 | 59858815 | 9 |
| Monkeypox virus strain Congo_2003_358 | Orthopoxvirus | 1524 | IL-18 BP (Bsh-D7L) | 599 | MPXV-COG_2003_358-011 | 47070 | 68448887 | 14 |
| Monkeypox virus strain Liberia_1970_184 | Orthopoxvirus | 1525 | IL-18 BP (Bsh-D7L) | 599 | MPXV-LBR_1970_184-011 | 47270 | 68449291 | 14 |
| Monkeypox virus strain Sierra Leone | Orthopoxvirus | 1521 | IL-18 BP (Bsh-D7L) | 599 | MPXV-SLE-009 | 46491 | 58220479 | 9 |
| Monkeypox virus strain USA_2003_039 | Orthopoxvirus | 1526 | IL-18 BP (Bsh-D7L) | 599 | MPXV-USA_2003_039-011 | 47468 | 68449490 | 14 |
| Monkeypox virus strain USA_2003_044 | Orthopoxvirus | 1522 | IL-18 BP (Bsh-D7L) | 599 | MPXV-USA_2003_044-011 | 46670 | 68448688 | 14 |
| Monkeypox virus strain Zaire | Orthopoxvirus | 1489 | IL-18 BP (Bsh-D7L) | 599 | MPXV-ZAR-009 | 40370 | 17974922 | D6L |
| Monkeypox virus strain Zaire_1979-005 | Orthopoxvirus | 1523 | IL-18 BP (Bsh-D7L) | 599 | MPXV-ZAR_1979_005-011 | 46868 | 68449088 | 14 |
| Rabbitpox virus strain Utrecht | Orthopoxvirus | 1494 | IL-18 BP (Bsh-D7L) | 599 | RPXV-Utr-009 | 41371 | 44971372 | 9 |
| Sheeppox virus strain A | Capripoxvirus | 1511 | IL-18 BP (14L) | 726 | SPPV-A-012 | 44521 | 0 | 12 |
| Sheeppox virus strain NISKHI | Capripoxvirus | 1512 | IL-18 BP (14L) | 726 | SPPV-NISKHI-011 | 44670 | 0 | 12 |
| Sheeppox virus strain TU-V02127 | Capripoxvirus | 1495 | IL-18 BP (14L) | 726 | SPPV-TU-012 | 41560 | 21492469 | 12 |
| Swinepox virus strain Nebraska 17077-99 | Suipoxvirus | 1490 | IL-18 BP (14L) | 726 | SWPV-Neb-011 | 40566 | 18640097 | 11 |
| Tanapox virus strain Kenya | Yatapoxvirus | 3496 | IL-18 BP (14L) | 726 | TANV-KEN-015 | 67471 | 146746350 | 14L |
| Tanapox virus strain isolate TPV-RoC | Yatapoxvirus | 3497 | IL-18 BP (14L) | 726 | TANV-COD-014 | 67561 | 146746506 | 14L |
| Taterapox virus strain Dahomey 1968 | Orthopoxvirus | 2195 | IL-18 BP (Bsh-D7L) | 599 | TATV-DAH68-017 | 52935 | 113195194 | interleukin-18-binding protein |
| Vaccinia virus strain 3737 | Orthopoxvirus | 1528 | IL-18 BP (Bsh-D7L) | 599 | VACV-3737-016 | 47804 | 88900632 | 11 |
| Vaccinia virus strain 3737 | Orthopoxvirus | 1528 | IL-18 BP (Bsh-D7L) | 599 | VACV-3737-207 | 47995 | 88900821 | 12 |
| Vaccinia virus strain Acambis 2000 | Orthopoxvirus | 2161 | IL-18 BP (Bsh-D7L) | 599 | VACV-Acam2000-019 | 51075 | 38348877 | 19 |
| Vaccinia virus strain Acambis 2000 | Orthopoxvirus | 2161 | IL-18 BP (Bsh-D7L) | 599 | VACV-Acam2000-218 | 51274 | 38349076 | 224 |
| Vaccinia virus strain Acambis 3 | Orthopoxvirus | 2162 | IL-18 BP (Bsh-D7L) | 599 | VACV-Acam3-019 | 51310 | 37551453 | 19 |
| Vaccinia virus strain Acambis 3000 Modified Virus Ankara | Orthopoxvirus | 1510 | IL-18 BP (Bsh-D7L) | 599 | VACV-Acam3000-010 | 44324 | 47088336 | 10 |
| Vaccinia virus strain DUKE | Orthopoxvirus | 2458 | IL-18 BP (Bsh-D7L) | 599 | VACV-DUKE-019 | 63399 | 90819671 | 19 |
| Vaccinia virus strain LC16m8 | Orthopoxvirus | 1517 | IL-18 BP (Bsh-D7L) | 599 | VACV-LC16m8-021 | 45474 | 56713362 | m8009L |
| Vaccinia virus strain LC16mO | Orthopoxvirus | 1518 | IL-18 BP (Bsh-D7L) | 599 | VACV-LC16mO-021 | 45758 | 56713646 | mO009L |
| Vaccinia virus strain Lister | Orthopoxvirus | 1519 | IL-18 BP (Bsh-D7L) | 599 | VACV-Lister-021 | 46042 | 0 | m8009L |

TABLE 7-continued

Viral Orthologous Clusters V2.0 (VOCs)
IL-18 binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Vaccinia virus strain Lister_VACV107 | Orthopoxvirus | 2659 | IL-18 BP (Bsh-D7L) | 599 | VACV-Lister_VACV107-017 | 64350 | 88854042 | List013 |
| Vaccinia virus strain MVA-I721 | Orthopoxvirus | 2696 | IL-18 BP (Bsh-D7L) | 599 | VACV-MVA_I721-098 | 65312 | 0 | 10 |
| Vaccinia virus strain Western Reserve | Orthopoxvirus | 1500 | IL-18 BP (Bsh-D7L) | 599 | VACV-WR-013 | 42450 | 66275810 | 13 |
| Vaccinia virus strain modified vaccinia Ankara | Orthopoxvirus | 1484 | IL-18 BP (Bsh-D7L) | 599 | VACV-MVA-004 | 65422 | 2772664 | MVA008L |
| Variola major virus strain Bangladesh 1975 | Orthopoxvirus | 1481 | IL-18 BP (Bsh-D7L) | 599 | VARV-BGD75maj-007 | 38768 | 438922 | D7L |
| Variola minor virus strain Garcia 1966 | Orthopoxvirus | 1482 | IL-18 BP (Bsh-D7L) | 599 | VARV-Gar_1966-006 | 38959 | 5830561 | B6L |
| Variola virus strain Afghanistan 1970 Variolator 4 | Orthopoxvirus | 2197 | IL-18 BP (Bsh-D7L) | 599 | VARV-AFG70-006 | 53350 | 109724045 | interleukin-18-binding protein |
| Variola virus strain Bangladesh 1974 (Shahzaman) | Orthopoxvirus | 2216 | IL-18 BP (Bsh-D7L) | 599 | VARV-BGD74_shz-006 | 56798 | 94484663 | interleukin-18-binding protein |
| Variola virus strain Bangladesh 1974 (Solaiman) | Orthopoxvirus | 2217 | IL-18 BP (Bsh-D7L) | 599 | VARV-BGD74_sol-006 | 56996 | 94484861 | interleukin-18-binding protein |
| Variola virus strain Bangladesh 1974 (nur islam) | Orthopoxvirus | 2215 | IL-18 BP (Bsh-D7L) | 599 | VARV-BGD74_nur-006 | 56600 | 94484466 | interleukin-18-binding protein |
| Variola virus strain Bangladesh 1975 v75-550 Banu | Orthopoxvirus | 2198 | IL-18 BP (Bsh-D7L) | 599 | VARV-BGD75_Banu-006 | 53553 | 109724249 | interleukin-18-binding protein |
| Variola virus strain Benin, Dahomey 1968 (v68-59) | Orthopoxvirus | 2224 | IL-18 BP (Bsh-D7L) | 599 | VARV-BEN68-006 | 58416 | 94483647 | interleukin-18-binding protein |
| Variola virus strain Botswana 1972 (v72-143) | Orthopoxvirus | 2225 | IL-18 BP (Bsh-D7L) | 599 | VARV-BWA72-006 | 58625 | 94483853 | interleukin-18-binding protein |
| Variola virus strain Botswana 1973 (v73-225) | Orthopoxvirus | 2226 | IL-18 BP (Bsh-D7L) | 599 | VARV-BWA73-006 | 58827 | 94484056 | interleukin-18-binding protein |
| Variola virus strain Brazil 1966 (v66-39 Sao Paulo) | Orthopoxvirus | 2227 | IL-18 BP (Bsh-D7L) | 599 | VARV-BRA66-006 | 59029 | 94484258 | interleukin-18-binding protein |
| Variola virus strain China Horn 1948 Sabin Lab July 1948 | Orthopoxvirus | 2203 | IL-18 BP (Bsh-D7L) | 599 | VARV-CHN48-006 | 54166 | 109724451 | interleukin-18-binding protein |
| Variola virus strain Congo 1970 v70-46 Kinshasa | Orthopoxvirus | 2229 | IL-18 BP (Bsh-D7L) | 599 | VARV-COG70_46-006 | 59441 | 109724656 | interleukin-18-binding protein |
| Variola virus strain Congo 9 1970 (v74-227 Gispen) | Orthopoxvirus | 2228 | IL-18 BP (Bsh-D7L) | 599 | VARV-COG70_227-006 | 59240 | 94485059 | interleukin-18-binding protein |
| Variola virus strain Ethiopia 1972 (Eth16 R14-1X-72 Addis) | Orthopoxvirus | 2231 | IL-18 BP (Bsh-D7L) | 599 | VARV-ETH72_16-006 | 59879 | 94485260 | interleukin-18-binding protein |
| Variola virus strain Ethiopia 1972 (Eth17 R14-1X-72 Addis) | Orthopoxvirus | 2232 | IL-18 BP (Bsh-D7L) | 599 | VARV-ETH72_17-006 | 60082 | 94485463 | interleukin-18-binding protein |
| Variola virus strain Germany 1958 Heidelberg | Orthopoxvirus | 2233 | IL-18 BP (Bsh-D7L) | 599 | VARV-DEU58-006 | 60283 | 109724860 | interleukin-18-binding protein |
| Variola virus strain Guinea 1969 (005) | Orthopoxvirus | 2234 | IL-18 BP (Bsh-D7L) | 599 | VARV-GIN69-006 | 60484 | 94485665 | interleukin-18-binding protein |
| Variola virus strain India 1953 (Kali-Muthu-M50 Madras) | Orthopoxvirus | 2238 | IL-18 BP (Bsh-D7L) | 599 | VARV-IND53_mad-006 | 61296 | 94485869 | interleukin-18-binding protein |
| Variola virus strain India 1953 (New Delhi) | Orthopoxvirus | 2239 | IL-18 BP (Bsh-D7L) | 599 | VARV-IND53_ndel-006 | 61497 | 94486071 | interleukin-18-binding protein |
| Variola virus strain India 1964 7124 Vellore | Orthopoxvirus | 2240 | IL-18 BP (Bsh-D7L) | 599 | VARV-IND64_vel4-007 | 61700 | 109725063 | interleukin-18-binding protein |

TABLE 7-continued

Viral Orthologous Clusters V2.0 (VOCs)
IL-18 binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain India 1964 7125 Vellore | Orthopoxvirus | 2241 | IL-18 BP (Bsh-D7L) | 599 | VARV-IND64_vel5-006 | 61904 | 109725268 | interleukin-18-binding protein |
| Variola virus strain India 3 Major 1967 | Orthopoxvirus | 1483 | IL-18 BP (Bsh-D7L) | 599 | VARV-IND3_1967-005 | 39167 | 9627526 | D5L |
| Variola virus strain Iran 1972 2602 Tabriz | Orthopoxvirus | 2235 | IL-18 BP (Bsh-D7L) | 599 | VARV-IRN72-006 | 60691 | 109725471 | interleukin-18-binding protein |
| Variola virus strain Japan 1946 (Yamada MS-2(A) Tokyo) | Orthopoxvirus | 2243 | IL-18 BP (Bsh-D7L) | 599 | VARV-JPN46_yam-006 | 62281 | 94486274 | interleukin-18-binding protein |
| Variola virus strain Japan 1951 (Harper, Masterseed) | Orthopoxvirus | 2244 | IL-18 BP (Bsh-D7L) | 599 | VARV-JPN51_hrpr-006 | 62483 | 94486477 | interleukin-18-binding protein |
| Variola virus strain Japan 1951 (Stillwell, Masterseed) | Orthopoxvirus | 2245 | IL-18 BP (Bsh-D7L) | 599 | VARV-JPN51_stwl-006 | 62684 | 94486679 | interleukin-18-binding protein |
| Variola virus strain Korea 1947 (Lee, Masterseed) | Orthopoxvirus | 2236 | IL-18 BP (Bsh-D7L) | 599 | VARV-KOR47-006 | 60894 | 94486881 | interleukin-18-binding protein |
| Variola virus strain Kuwait 1967 (K1629) | Orthopoxvirus | 2237 | IL-18 BP (Bsh-D7L) | 599 | VARV-KWT67-006 | 61096 | 94487084 | interleukin-18-binding protein |
| Variola virus strain Nepal 1973 V73-175 | Orthopoxvirus | 2221 | IL-18 BP (Bsh-D7L) | 599 | VARV-NPL73-006 | 57796 | 109725675 | interleukin-18-binding protein |
| Variola virus strain Niger 1969 (001, importation from Nigeria) | Orthopoxvirus | 2222 | IL-18 BP (Bsh-D7L) | 599 | VARV-NER69-006 | 57999 | 94487284 | interleukin-18-binding protein |
| Variola virus strain Sierra Leone 1969 (V68-258) | Orthopoxvirus | 2223 | IL-18 BP (Bsh-D7L) | 599 | VARV-SLE68-006 | 58208 | 94487893 | interleukin-18-binding protein |
| Variola virus strain Somalia 1977 (V77-1252) | Orthopoxvirus | 2218 | IL-18 BP (Bsh-D7L) | 599 | VARV-SOM77_1252-006 | 57194 | 94488098 | interleukin-18-binding protein |
| Variola virus strain Somalia 1977 (V77-1605) | Orthopoxvirus | 2219 | IL-18 BP (Bsh-D7L) | 599 | VARV-SOM77_1605-006 | 57394 | 94488298 | interleukin-18-binding protein |
| Variola virus strain Somalia 1977 V77-2479 | Orthopoxvirus | 2220 | 1L-18 BP (Bsh-D7L) | 599 | VARV-SOM77_ali-006 | 57594 | 109726082 | interleukin-18-binding protein |
| Variola virus strain South Africa 1965 (102 Natal, Ingwavuma) | Orthopoxvirus | 2210 | IL-18 BP (Bsh-D7L) | 599 | VARV-ZAF65_102-006 | 55578 | 94487490 | interleukin-18-binding protein |
| Variola virus strain South Africa 1965 (103 Tvaal, Nelspruit) | Orthopoxvirus | 2211 | IL-18 BP (Bsh-D7L) | 599 | VARV-ZAF65_103-006 | 55779 | 94487691 | interleukin-18-binding protein |
| Variola virus strain Sudan 1947 (Juba) | Orthopoxvirus | 2212 | IL-18 BP (Bsh-D7L) | 599 | VARV-SDN47_jub-006 | 55980 | 94488498 | interleukin-18-binding protein |
| Variola virus strain Sudan 1947 (Rumbec) | Orthopoxvirus | 2213 | IL-18 BP (Bsh-D7L) | 599 | VARV-SDN47_rum-006 | 56180 | 94488699 | interleukin-18-binding protein |
| Variola virus strain Sumatra 1970 V70-222 | Orthopoxvirus | 2208 | IL-18 BP (Bsh-D7L) | 599 | VARV-SUM70_222-006 | 55176 | 109726285 | interleukin-18-binding protein |
| Variola virus strain Sumatra 1970 V70-228 | Orthopoxvirus | 2209 | IL-18 BP (Bsh-D7L) | 599 | VARV-SUM70_228-006 | 55378 | 94488900 | interleukin-18-binding protein |
| Variola virus strain Syria 1972 V72-199 | Orthopoxvirus | 2206 | IL-18 BP (Bsh-D7L) | 599 | VARV-SYR72-006 | 54772 | 109726488 | interleukin-18-binding protein |
| Variola virus strain Tanzania 1965 kembula | Orthopoxvirus | 2207 | IL-18 BP (Bsh-D7L) | 599 | VARV-TZA65-006 | 54975 | 94489100 | interleukin-18-binding protein |
| Variola virus strain United Kingdom 1946 Harvey | Orthopoxvirus | 2204 | IL-18 BP (Bsh-D7L) | 599 | VARV-GBR44_harv-006 | 54371 | 94489299 | interleukin-18-binding protein |

TABLE 7-continued

Viral Orthologous Clusters V2.0 (VOCs)
IL-18 binding protein
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain United Kingdom 1946 Hinden (Middlesex) | Orthopoxvirus | 2205 | IL-18 BP (Bsh-D7L) | 599 | VARV-GBR46__hind-006 | 54573 | 94489502 | interleukin-18-binding protein |
| Variola virus strain United Kingdom 1947 Higgins (Staffordshire) | Orthopoxvirus | 2202 | IL-18 BP (Bsh-D7L) | 599 | VARV-GBR47__hig-006 | 53965 | 94489701 | interleukin-18-binding protein |
| Variola virus strain United Kingdom 1952 Butler | Orthopoxvirus | 2200 | IL-18 BP (Bsh-D7L) | 599 | VARV-GBR52__but-006 | 53754 | 94489902 | interleukin-18-binding protein |
| Variola virus strain Yugoslavia 1972 V72-164 | Orthopoxvirus | 2196 | IL-18 BP (Bsh-D7L) | 599 | VARV-YUG72-006 | 53149 | 94490110 | interleukin-18-binding protein |
| Yaba monkey tumor virus strain Amano | Yatapoxvirus | 1503 | IL-18 BP (14L) | 726 | YMTV-Amano-010 | 43059 | 38229179 | 14L |
| Yaba-like Disease Virus strain Davis | Yatapoxvirus | 1487 | IL-18 BP (14L) | 726 | YLDV-Davis-014 | 40063 | 12084997 | 14L |

TABLE 8

Viral Orthologous Clusters V2.0 (VOCs)
INF-gamma
Gene Results Table

| Genome name | Genus | Genome id | Ortholog Group Name | Ortholog Group ID | Gene number | Gene id | Genbank id | Genbank name |
|---|---|---|---|---|---|---|---|---|
| Camelpox virus strain CMS | Orthopoxvirus | 1493 | IFN-gamma receptor | 564 | CMLV-CMS-233 | 41329 | 19718161 | 181R |
| Camelpox virus strain M96 | Orthopoxvirus | 1491 | IFN-gamma receptor | 564 | CMLV-M96-186 | 40892 | 18640418 | 184 |
| Cowpox virus strain Brighton Red | Orthopoxvirus | 1496 | IFN-gamma receptor | 564 | CPXV-BR-208 | 41907 | 20178562 | 202 |
| Cowpox virus strain GRI-90 | Orthopoxvirus | 1501 | IFN-gamma receptor | 564 | CPXV-GRI-190 | 42847 | 30519558 | B7R |
| Cowpox virus strain Germany 91-3 | Orthopoxvirus | 2214 | IFN-gamma receptor | 564 | CPXV-GER91-189 | 56564 | 90660422 | interferon-gamma receptor-like |
| Deerpox virus strain W-1170-84 | Unclassified | 1516 | IFN-gamma receptor | 564 | DPV-W1170_84-010 | 45293 | 0 | 10 |
| Deerpox virus strain W-848-83 | Unclassified | 1515 | IFN-gamma receptor | 564 | DPV-W848_83-010 | 45123 | 62637389 | 10 |
| Ectromelia virus strain Moscow | Orthopoxvirus | 1492 | IFN-gamma receptor | 564 | ECTV-Mos-163 | 41082 | 22164593 | 158 |
| Ectromelia virus strain Naval | Orthopoxvirus | 1499 | IFN-gamma receptor | 564 | ECTV-Nav-168 | 42423 | 0 | 185 |
| Goatpox virus strain G20-LKV | Capripoxvirus | 1514 | IFN-gamma receptor | 564 | GTPV-G20LKV-006 | 44966 | 0 | 6 |
| Goatpox virus strain Pellor | Capripoxvirus | 1513 | IFN-gamma receptor | 564 | GTPV-Pellor-006 | 44816 | 0 | 6 |
| Horsepox virus strain MNR-76 | Orthopoxvirus | 2230 | IFN-gamma receptor | 564 | HSPV-MNR76-211 | 59848 | 111184378 | HSPV185 |
| Lumpy skin disease virus strain Neethling 2490 | Capripoxvirus | 1488 | IFN-gamma receptor | 564 | LSDV-Nee-008 | 40211 | 15150447 | 8 |
| Lumpy skin disease virus strain Neethling Warmbaths LW | Capripoxvirus | 1497 | IFN-gamma receptor | 564 | LSDV-NW_LW-008 | 41942 | 22595541 | 8 |
| Lumpy skin disease virus strain Neethling vaccine LW 1959 | Capripoxvirus | 1498 | IFN-gamma receptor | 564 | LSDV-LW1959-008 | 42102 | 22595700 | 8 |
| Monkeypox Virus strain Walter Reed 267 | Orthopoxvirus | 1502 | IFN-gamma receptor | 564 | MPXV-WR267-163 | 43034 | 0 | 162 |
| Monkeypox virus strain COP-58 | Orthopoxvirus | 1520 | IFN-gamma receptor | 564 | MPXV-COP58-162 | 46467 | 59858968 | 162 |

TABLE 8-continued

Viral Orthologous Clusters V2.0
(VOCs)
INF-gamma
Gene Results Table

| Genome name | Genus | Genome id | Ortholog Group Name | Ortholog Group ID | Gene number | Gene id | Genbank id | Genbank name |
|---|---|---|---|---|---|---|---|---|
| Monkeypox virus strain Congo_2003_358 | Orthopoxvirus | 1524 | IFN-gamma receptor | 564 | MPXV-COG_2003_358-1 | 47235 | 68449052 | 183 |
| Monkeypox virus strain Liberia_1970_184 | Orthopoxvirus | 1525 | IFN-gamma receptor | 564 | MPXV-LBR_1970_184-17 | 47434 | 68449455 | 183 |
| Monkeypox virus strain Sierra Leone | Orthopoxvirus | 1521 | IFN-gamma receptor | 564 | MPXV-SLE-162 | 46644 | 58220632 | 162 |
| Monkeypox virus strain USA_2003_039 | Orthopoxvirus | 1526 | IFN-gamma receptor | 564 | MPXV-USA_2003_039-17 | 47633 | 68449655 | 183 |
| Monkeypox virus strain USA_2003_044 | Orthopoxvirus | 1522 | IFN-gamma receptor | 564 | MPXV-USA_2003_044-17 | 46835 | 68448853 | 183 |
| Monkeypox virus strain Zaire | Orthopoxvirus | 1489 | IFN-gamma receptor | 564 | MPXV-ZAR-173 | 40534 | 17975083 | B9R |
| Monkeypox virus strain Zaire_1979-005 | Orthopoxvirus | 1523 | IFN-gamma receptor | 564 | MPXV-ZAR_1979_005-17 | 47034 | 68449254 | 183 |
| Myxoma virus strain Lausanne | Leporipoxvirus | 1479 | IFN-gamma receptor | 564 | MYXV-Lau-010 | 38435 | 9633801 | m007L |
| Myxoma virus strain Lausanne | Leporipoxvirus | 1479 | IFN-gamma receptor | 564 | MYXV-Lau-162 | 38586 | 9633642 | m007R |
| Rabbit fibroma virus strain Kasza | Leporipoxvirus | 1480 | IFN-gamma receptor | 564 | SFV-Kas-009 | 38604 | 9633817 | gp007L |
| Rabbit fibroma virus strain Kasza | Leporipoxvirus | 1480 | IFN-gamma receptor | 564 | SFV-Kas-158 | 38753 | 9633962 | gp007R |
| Rabbitpox virus strain Utrecht | Orthopoxvirus | 1494 | IFN-gamma receptor | 564 | RPXV-Utr-172 | 41534 | 44971533 | 170 |
| Sheeppox virus strain A | Capripoxvirus | 1511 | IFN-gamma receptor | 564 | SPPV-A-006 | 44515 | 0 | 6 |
| Sheeppox virus strain NISKHI | Capripoxvirus | 1512 | IFN-gamma receptor | 564 | SPPV-NISKHI-005 | 44664 | 0 | 6 |
| Sheeppox virus strain TU-V02127 | Capripoxvirus | 1495 | IFN-gamma receptor | 564 | SPPV-TU-006 | 41554 | 21492463 | 6 |
| Swinepox virus strain Nebraska 17077-99 | Suipoxvirus | 1490 | IFN-gamma receptor | 564 | Neb-008 | 40563 | 18640094 | 8 |
| Taterapox virus strain Dahomey 1968 | Orthopoxvirus | 2195 | IFN-gamma receptor | 564 | TATV-DAH68-191 | 53109 | 113195368 | interferon-gamma receptor-like protein |
| Vaccinia virus strain 3737 | Orthopoxvirus | 1528 | IFN-gamma receptor | 564 | VACV-3737-191 | 47979 | 88900807 | 180 |
| Vaccinia virus strain Acambis 2000 | Orthopoxvirus | 2161 | IFN-gamma receptor | 564 | VACV-Acam2000-199 | 51255 | 38349057 | 201 |
| Vaccinia virus strain Acambis 3 | Orthopoxvirus | 2162 | IFN-gamma receptor | 564 | VACV-Acam3-201 | 51492 | 37551635 | 201 |
| Vaccinia virus strain Acambis 3000 Modified Virus Ankara | Orthopoxvirus | 1510 | IFN-gamma receptor | 564 | VACV-Acam3000-178 | 44492 | 47088502 | 176 |
| Vaccinia virus strain Copenhagen | Orthopoxvirus | 1485 | IFN-gamma receptor | 564 | VACV-Cop-241 | 39766 | 335553 | B8R |
| Vaccinia virus strain DUKE | Orthopoxvirus | 2458 | IFN-gamma receptor | 564 | VACV-DUKE-199 | 63579 | 90819851 | 199 |
| Vaccinia virus strain LC16m8 | Orthopoxvirus | 1517 | IFN-gamma receptor | 564 | VACV-LC16m8-257 | 45710 | 56713596 | m8247R |
| Vaccinia virus strain LC16mO | Orthopoxvirus | 1518 | IFN-gamma receptor | 564 | VACV-LC16mO-257 | 45994 | 56713880 | mO247R |
| Vaccinia virus strain Lister | Orthopoxvirus | 1519 | IFN-gamma receptor | 564 | VACV-Lister-257 | 46278 | 0 | m8247R |
| Vaccinia virus strain Lister_VACV107 | Orthopoxvirus | 2659 | IFN-gamma receptor | 564 | VACV-Lister_VACV107-1$$ | 64522 | 88854272 | List185 |
| Vaccinia virus strain MVA-I721 | Orthopoxvirus | 2696 | IFN-gamma receptor | 564 | VACV-MVA_I721-089 | 65303 | 0 | 176 |
| Vaccinia virus strain Western Reserve | Orthopoxvirus | 1500 | IFN-gamma receptor | 564 | VACV-WR-190 | 42629 | 66275987 | 190 |
| Variola major virus strain Bangladesh 1975 | Orthopoxvirus | 1481 | IFN-gamma receptor | 564 | VARV-BGD75maj-175 | 38936 | 439086 | B8R |
| Variola minor virus strain Garcia 1966 | Orthopoxvirus | 1482 | IFN-gamma receptor | 564 | VARV-Gar_1966-187 | 39140 | 5830739 | H9R |

TABLE 8-continued

Viral Orthologous Clusters V2.0
(VOCs)
INF-gamma
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Afghanistan 1970 Variolator 4 | Orthopoxvirus | 2197 | IFN-gamma receptor | 564 | VARV-AFG70-181 | 53525 | 109724220 | interferon-gamma receptor-like soluble protein |
| Variola virus strain Bangladesh 1974 (Shahzaman) | Orthopoxvirus | 2216 | IFN-gamma receptor | 564 | VARV-BGD74_shz-180 | 56972 | 94484837 | interferon-gamma receptor-like soluble protein |
| Variola virus strain Bangladesh 1974 (Solaiman) | Orthopoxvirus | 2217 | IFN-gamma receptor | 564 | VARV-BGD74_sol-180 | 57170 | 94485035 | interferon-gamma receptor-like soluble protein |
| Variola virus strain Bangladesh 1974 (nur islam) | Orthopoxvirus | 2215 | IFN-gamma receptor | 564 | VARV-BGD74_nur-180 | 56774 | 94484639 | interferon-gamma receptor-like soluble protein |
| Variola virus strain Bangladesh 1975 v75-550 Banu | Orthopoxvirus | 2198 | IFN-gamma receptor | 564 | VARV-BGD75_Banu-180 | 53727 | 109724423 | interferon-gamma receptor-like soluble protein |
| Variola virus strain Benin, Dahomey 1968 (v68-59) | Orthopoxvirus | 2224 | IFN-gamma receptor | 564 | VARV-BEN68-185 | 58595 | 94483824 | interferon-gamma receptor-like soluble protein |
| Variola virus strain Botswana 1972 (v72-143) | Orthopoxvirus | 2225 | IFN-gamma receptor | 564 | VARV-BWA72-181 | 58800 | 94484028 | interferon-gamma receptor-like soluble protein |
| Variola virus strain Botswana 1973 (v73-225) | Orthopoxvirus | 2226 | IFN-gamma receptor | 564 | VARV-BWA73-181 | 59002 | 94484231 | interferon-gamma receptor-like soluble protein |
| Variola virus strain Brazil 1966 (v66-39 Sao Paulo) | Orthopoxvirus | 2227 | IFN-gamma receptor | 564 | VARV-BRA66-188 | 59211 | 94484438 | interferon-gamma receptor-like soluble protein |
| Variola virus strain China Horn 1948 Sabin Lab July 1948 | Orthopoxvirus | 2203 | IFN-gamma receptor | 564 | VARV-CHN48-182 | 54342 | 109724626 | interferon-gamma receptor-like soluble protein |
| Variola virus strain Congo 1970 v70-46 Kinshasa | Orthopoxvirus | 2229 | IFN-gamma receptor | 564 | VARV-COG70_46-180 | 59615 | 109724831 | interferon-gamma receptor-like soluble protein |
| Variola virus strain Congo 9 1970 (v74-227 Gispen) | Orthopoxvirus | 2228 | IFN-gamma receptor | 564 | VARV-COG70_227-181 | 59415 | 94485234 | interferon-gamma receptor-like soluble protein |
| Variola virus strain Ethiopia 1972 (Eth16 R14-1X-72 Addis) | Orthopoxvirus | 2231 | IFN-gamma receptor | 564 | VARV-ETH72_16-182 | 60055 | 94485436 | interferon-gamma receptor-like soluble protein |
| Variola virus strain Ethiopia 1972 (Eth17 R14-1X-72 Addis) | Orthopoxvirus | 2232 | IFN-gamma receptor | 564 | VARV-ETH72_17-182 | 60258 | 94485639 | interferon-gamma receptor-like soluble protein |
| Variola virus strain Germany 1958 Heidelberg | Orthopoxvirus | 2233 | IFN-gamma receptor | 564 | VARV-DEU58-180 | 60457 | 109725034 | interferon-gamma receptor-like soluble protein |
| Variola virus strain Guinea 1969 (005) | Orthopoxvirus | 2234 | IFN-gamma receptor | 564 | VARV-GIN69-184 | 60662 | 94485841 | interferon-gamma receptor-like soluble protein |
| Variola virus strain India 1953 (Kali-Muthu-M50 Madras) | Orthopoxvirus | 2238 | IFN-gamma receptor | 564 | VARV-IND53_mad-182 | 61472 | 94486045 | interferon-gamma receptor-like soluble protein |
| Variola virus strain India 1953 (New Delhi) | Orthopoxvirus | 2239 | IFN-gamma receptor | 564 | VARV-IND53_ndel-181 | 61672 | 94486246 | interferon-gamma receptor-like soluble protein |
| Variola virus strain India 1964 7124 Vellore | Orthopoxvirus | 2240 | IFN-gamma receptor | 564 | VARV-IND64_vel4-183 | 61876 | 109725239 | interferon-gamma receptor-like soluble protein |
| Variola virus strain India 1964 7125 Vellore | Orthopoxvirus | 2241 | IFN-gamma receptor | 564 | VARV-IND64_vel5-182 | 62080 | 109725444 | interferon-gamma receptor-like protein |
| Variola virus strain India 3 Major 1967 | Orthopoxvirus | 1483 | IFN-gamma receptor | 564 | VARV-IND3_1967-180 | 39342 | 9627698 | B9R |
| Variola virus strain Iran 1972 2602 Tabriz | Orthopoxvirus | 2235 | IFN-gamma receptor | 564 | VARV-IRN72-181 | 60866 | 109725646 | interferon-gamma receptor-like soluble protein |

TABLE 8-continued

Viral Orthologous Clusters V2.0
(VOCs)
INF-gamma
Gene Results Table

| Genome name | Genus | Genome id | Ortholog Group Name | Ortholog Group ID | Gene number | Gene id | Gen-bank id | Genbank name |
|---|---|---|---|---|---|---|---|---|
| Variola virus strain Japan 1946 (Yamada MS-2(A) Tokyo) | Orthopoxvirus | 2243 | IFN-gamma receptor | 564 | VARV-JPN46_yam-181 | 62456 | 94486449 | interferon-gamma receptor-like soluble protein |
| Variola virus strain Japan 1951 (Harper, Masterseed) | Orthopoxvirus | 2244 | IFN-gamma receptor | 564 | VARV-JPN51_hrpr-181 | 62658 | 94486652 | interferon-gamma receptor-like soluble protein |
| Variola virus strain Japan 1951 (Stillwell, Masterseed) | Orthopoxvirus | 2245 | IFN-gamma receptor | 564 | VARV-JPN51_stwl-181 | 62859 | 94486854 | interferon-gamma receptor-like soluble protein |
| Variola virus strain Korea 1947 (Lee, Masterseed) | Orthopoxvirus | 2236 | IFN-gamma receptor | 564 | VARV-KOR47-182 | 61070 | 94487057 | interferon-gamma receptor-like soluble protein |
| Variola virus strain Kuwait 1967 (K1629) | Orthopoxvirus | 2237 | IFN-gamma receptor | 564 | VARV-KWT67-181 | 61271 | 94487259 | interferon-gamma receptor-like soluble protein |
| Variola virus strain Nepal 1973 V73-175 | Orthopoxvirus | 2221 | IFN-gamma receptor | 564 | VARV-NPL73-180 | 57970 | 109725849 | interferon-gamma receptor-like soluble protein |
| Variola virus strain Niger 1969 (001, importation from Nigeria) | Orthopoxvirus | 2222 | IFN-gamma receptor | 564 | VARV-NER69-186 | 58179 | 94487462 | interferon-gamma receptor-like soluble protein |
| Variola virus strain Sierra Leone 1969 (V68-258) | Orthopoxvirus | 2223 | IFN-gamma receptor | 564 | VARV-SLE68-185 | 58387 | 94488070 | interferon-gamma receptor-like soluble protein |
| Variola virus strain Somalia 1977 (V77-1252) | Orthopoxvirus | 2218 | IFN-gamma receptor | 564 | VARV-SOM77_1252-180 | 57368 | 94488272 | interferon-gamma receptor-like soluble protein |
| Variola virus strain Somalia 1977 (V77-1605) | Orthopoxvirus | 2219 | IFN-gamma receptor | 564 | VARV-SOM77_1605-180 | 57568 | 94488472 | interferon-gamma receptor-like soluble protein |
| Variola virus strain Somalia 1977 V77-2479 | Orthopoxvirus | 2220 | IFN-gamma receptor | 564 | VARV-SOM77_ali-180 | 57768 | 109726256 | interferon-gamma receptor-like soluble protein |
| Variola virus strain South Africa 1965 (102 Natal, Ingwavuma) | Orthopoxvirus | 2210 | IFN-gamma receptor | 564 | VARV-ZAF65_102-181 | 55753 | 94487665 | interferon-gamma receptor-like soluble protein |
| Variola virus strain South Africa 1965 (103 Tvaal, Nelspruit) | Orthopoxvirus | 2211 | IFN-gamma receptor | 564 | VARV-ZAF65_103-181 | 55954 | 94487866 | interferon-gamma receptor-like soluble protein |
| Variola virus strain Sudan 1947 (Juba) | Orthopoxvirus | 2212 | IFN-gamma receptor | 564 | VARV-SDN47_jub-181 | 56155 | 94488673 | interferon-gamma receptor-like soluble protein |
| Variola virus strain Sudan 1947 (Rumbec) | Orthopoxvirus | 2213 | IFN-gamma receptor | 564 | VARV-SDN47_rum-181 | 56355 | 94488874 | interferon-gamma receptor-like soluble protein |
| Variola virus strain Sumatra 1970 V70-222 | Orthopoxvirus | 2208 | IFN-gamma receptor | 564 | VARV-SUM70_222-180 | 55350 | 109726459 | interferon-gamma receptor-like soluble protein |
| Variola virus strain Sumatra 1970 V70-228 | Orthopoxvirus | 2209 | IFN-gamma receptor | 564 | VARV-SUM70_228-180 | 55552 | 94489074 | interferon-gamma receptor-like soluble protein |
| Variola virus strain Syria 1972 V72-199 | Orthopoxvirus | 2206 | IFN-gamma receptor | 564 | VARV-SYR72-181 | 54947 | 109726663 | interferon-gamma receptor-like soluble protein |
| Variola virus strain Tanzania 1965 kembula | Orthopoxvirus | 2207 | IFN-gamma receptor | 564 | VARV-TZA65-181 | 55150 | 94489273 | interferon-gamma receptor-like soluble protein |
| Variola virus strain United Kingdom 1946 Harvey | Orthopoxvirus | 2204 | IFN-gamma receptor | 564 | VARV-GBR44_harv-182 | 54547 | 94489475 | interferon-gamma receptor-like soluble protein |
| Variola virus strain United Kingdom 1946 Hinden (Middlesex) | Orthopoxvirus | 2205 | IFN-gamma receptor | 564 | VARV-GBR46_hind-181 | 54748 | 94489677 | interferon-gamma receptor-like soluble protein |
| Variola virus strain United | Orthopoxvirus | 2202 | IFN-gamma receptor | 564 | VARV-GBR47_hig-181 | 54140 | 94489875 | interferon-gamma receptor-like |

TABLE 8-continued

Viral Orthologous Clusters V2.0
(VOCs)
INF-gamma
Gene Results Table

| Genome name | Genus | Genome id | Ortholog Group Name | Ortholog Group ID | Gene number | Gene id | Genbank id | Genbank name |
|---|---|---|---|---|---|---|---|---|
| Kingdom 1947 Higgins (Staffordshire) | | | | | | | | soluble protein |
| Variola virus strain United Kingdom 1952 Butler | Orthopoxvirus | 2200 | IFN-gamma receptor | 564 | VARV-GBR52_but-188 | 53936 | 94490082 | interferon-gamma receptor-like soluble protein |
| Variola virus strain Yugoslavia 1972 V72-164 | Orthopoxvirus | 2196 | IFN-gamma receptor | 564 | VARV-YUG72-181 | 53324 | 94490285 | interferon-gamma receptor-like soluble protein |

TABLE 9

Viral Orthologous Clusters V2.0
(VOCs)
Interferonalpha-beta
Gene Results Table

| Genome name | Genus | Genome id | Ortholog Group Name | Ortholog Group ID | Gene number | Gene Id | Genbank id | Genbank name |
|---|---|---|---|---|---|---|---|---|
| Camelpox virus strain CMS | Orthopoxvirus | 1493 | IFN-alpha/beta receptor | 584 | CMLV-CMS-252 | 41348 | 19718180 | 196R |
| Camelpox virus strain M96 | Orthopoxvirus | 1491 | IFN-alpha/beta receptor | 584 | CMLV-M96-203 | 40909 | 18640435 | 201 |
| Cowpox virus strain Brighton Red | Orthopoxvirus | 1496 | IFN-alpha/beta receptor | 584 | CPXV-BR-218 | 41917 | 20178572 | 212 |
| Cowpox virus strain GRI-90 | Orthopoxvirus | 1501 | IFN-alpha/beta receptor | 584 | CPXV-GRI-200 | 42857 | 30519568 | B17R |
| Cowpox virus strain Germany 91-3 | Orthopoxvirus | 2214 | IFN-alpha/beta receptor | 584 | CPXV-GER91-200 | 56575 | 90660433 | immunoglobulin superfamily secreted glycoprotein |
| Deerpox virus strain W-1170-84 | Unclassified | 1516 | IFN-alpha/beta receptor | 584 | DPV-W1170_84-145 | 45428 | 0 | 147b |
| Deerpox virus strain W-1170-84 | Unclassified | 1516 | IFN-alpha/beta receptor | 584 | DPV-W1170_84-146 | 45429 | 0 | 147a |
| Deerpox virus strain W-848-83 | Unclassified | 1515 | IFN-alpha/beta receptor | 584 | DPV-W848_83-145 | 45258 | 62637524 | 147a |
| Ectromelia virus strain Moscow | Orthopoxvirus | 1492 | IFN-alpha/beta receptor | 584 | ECTV-Mos-171 | 41090 | 22164601 | 166 |
| Ectromelia virus strain Naval | Orthopoxvirus | 1499 | IFN-alpha/beta receptor | 584 | ECTV-Nav-176 | 42431 | 0 | 194 |
| Goatpox virus strain G20-LKV | Capripoxvirus | 1514 | IFN-alpha/beta receptor | 584 | GTPV-G20LKV-134 | 45094 | 0 | 129 |
| Goatpox virus strain Pellor | Capripoxvirus | 1513 | IFN-alpha/beta receptor | 584 | GTPV-Pellor-132 | 44942 | 0 | 129 |
| Horsepox virus strain MNR-76 | Orthopoxvirus | 2230 | IFN-alpha/beta receptor | 584 | HSPV-MNR76-221 | 59858 | 111184388 | HSPV195 |
| Lumpy skin disease virus strain Neethling 2490 | Capripoxvirus | 1488 | IFN-alpha/beta receptor | 584 | LSDV-Nee-137 | 40340 | 15150574 | 135 |
| Lumpy skin disease virus strain Neethling Warmbaths LW | Capripoxvirus | 1497 | IFN-alpha/beta receptor | 584 | LSDV-NW_LW-139 | 42073 | 22595670 | 135 |
| Lumpy skin disease virus strain Neethling vaccine LW 1959 | Capripoxvirus | 1498 | IFN-alpha/beta receptor | 584 | LSDV-LW1959-139 | 42233 | 22595829 | 135 |
| Monkeypox Virus strain Walter Reed 267 | Orthopoxvirus | 1502 | IFN-alpha/beta receptor | 584 | MPXV-WR267-168 | 43039 | 0 | 167 |
| Monkeypox virus strain COP-58 | Orthopoxvirus | 1520 | IFN-alpha/beta receptor | 584 | MPXV-COP58-167 | 46472 | 59858973 | 167 |
| Monkeypox virus strain Congo_2003_358 | Orthopoxvirus | 1524 | IFN-alpha/beta receptor | 584 | MPXV-COG_2003_358-185 | 47244 | 68449061 | 192 |
| Monkeypox virus strain Liberia_1970_184 | Orthopoxvirus | 1525 | IFN-alpha/beta receptor | 584 | MPXV-LBR_1970_184-185 | 47444 | 68449465 | 192 |
| Monkeypox virus strain Sierra Leone | Orthopoxvirus | 1521 | IFN-alpha/beta receptor | 584 | MPXV-SLE-167 | 46649 | 58220637 | 167 |
| Monkeypox virus strain USA_2003_039 | Orthopoxvirus | 1526 | IFN-alpha/beta receptor | 584 | MPXV-USA_2003_039-185 | 47642 | 68449664 | 192 |

TABLE 9-continued

Viral Orthologous Clusters V2.0
(VOCs)
Interferonalpha-beta
Gene Results Table

| Genome name | Genus | Genome id | Ortholog Group Name | Ortholog Group ID | Gene number | Gene Id | Genbank id | Genbank name |
|---|---|---|---|---|---|---|---|---|
| Monkeypox virus strain USA_2003_044 | Orthopoxvirus | 1522 | IFN-alpha/beta receptor | 584 | MPXV-USA 2003_044-185 | 46844 | 68448862 | 192 |
| Monkeypox virus strain Zaire | Orthopoxvirus | 1489 | IFN-alpha/beta receptor | 584 | MPXV-ZAR-180 | 40541 | 17975090 | B16R |
| Monkeypox virus strain Zaire_1979-005 | Orthopoxvirus | 1523 | IFN-alpha/beta receptor | 584 | MPXV-ZAR_1979_005-187 | 47044 | 68449264 | 192 |
| Myxoma virus strain Lausanne | Leporipoxvirus | 1479 | IFN-alpha/beta receptor | 584 | MYXV-Lau-140 | 38564 | 9633771 | m135R |
| Rabbitpox virus strain Utrecht | Orthopoxvirus | 1494 | IFN-alpha/beta receptor | 584 | RPXV-Utr-181 | 41543 | 44971542 | 179 |
| Sheeppox virus strain A | Capripoxvirus | 1511 | IFN-alpha/beta receptor | 584 | SPPV-A-132 | 44641 | 0 | 129 |
| Sheeppox virus strain NISKHI | Capripoxvirus | 1512 | IFN-alpha/beta receptor | 584 | SPPV-NISKHI-131 | 44790 | 0 | 129 |
| Sheeppox virus strain TU-V02127 | Capripoxvirus | 1495 | IFN-alpha/beta receptor | 584 | SPPV-TU-132 | 41680 | 21492586 | 129 |
| Swinepox virus strain Nebraska 17077-99 | Suipoxvirus | 1490 | IFN-alpha/beta receptor | 584 | SWPV-Neb-133 | 40688 | 18640218 | 132 |
| Tanapox virus strain Kenya | Yatapoxvirus | 3496 | IFN-alpha/beta receptor | 584 | TANV-KEN-141 | 67659 | 146746476 | 136R |
| Tanapox virus strain isolate TPV-RoC | Yatapoxvirus | 3497 | IFN-alpha/beta receptor | 584 | TANV-COD-140 | 67752 | 146746632 | 136R |
| Taterapox virus strain Dahomey 1968 | Orthopoxvirus | 2195 | IFN-alpha/beta receptor | 584 | TATV-DAH68-210 | 53128 | 113195387 | IFN-alpha:beta-receptor-like secreted glycoprotein |
| Vaccinia virus strain 3737 | Orthopoxvirus | 1528 | IFN-alpha/beta receptor | 584 | VACV-3737-202 | 47990 | 88900816 | 188 |
| Vaccinia virus strain Acambis 2000 | Orthopoxvirus | 2161 | IFN-alpha/beta receptor | 584 | VACV-Acam2000-210 | 51266 | 38349068 | 212 |
| Vaccinia virus strain Acarnbis 3 | Orthopoxvirus | 2162 | IFN-alpha/beta receptor | 584 | VACV-Acam3-212 | 51503 | 37551646 | 212 |
| Vaccinia virus strain Acambis 3000 Modified Virus Ankara | Orthopoxvirus | 1510 | IFN-alpha/beta receptor | 584 | VACV-Acam3000-189 | 44503 | 47088513 | 187 |
| Vaccinia virus strain Copenhagen | Orthopoxvirus | 1485 | IFN-alpha/beta receptor | 584 | VACV-Cop-254 | 39779 | 335566 | B19R |
| Vaccinia virus strain DUKE | Orthopoxvirus | 2458 | IFN-alpha/beta receptor | 584 | VACV-DUKE-210 | 63590 | 90819862 | 210 |
| Vaccinia virus strain MVA-I721 | Orthopoxvirus | 2696 | IFN-alpha/beta receptor | 584 | VACV-MVA_I721-066 | 65280 | 0 | 187 |
| Vaccinia virus strain Western Reserve | Orthopoxvirus | 1500 | IFN-alpha/beta receptor | 584 | VACV-WR-200 | 42639 | 66275997 | 200 |
| Variola major virus strain Bangladesh 1975 | Orthopoxvirus | 1481 | IFN-alpha/beta receptor | 584 | VARV-BGD75maj-184 | 38945 | 439095 | B17R |
| Variola minor virus strain Garcia 1966 | Orthopoxvirus | 1482 | IFN-alpha/beta receptor | 584 | VARV-Gar_1966-199 | 39152 | 5830751 | D9R |
| Variola virus strain Afghanistan 1970 Variolator 4 | Orthopoxvirus | 2197 | IFN-alpha/beta receptor | 584 | VARV-AFG70-193 | 53537 | 109724232 | glycoprotein |
| Variola virus strain Bangladesh 1974 (Shahzaman) | Orthopoxvirus | 2216 | IFN-alpha/beta receptor | 584 | VARV-BGD74_shz-189 | 56981 | 94484846 | glycoprotein |
| Variola virus strain Bangladesh 1974 (Solaiman) | Orthopoxvirus | 2217 | IFN-alpha/beta receptor | 584 | VARV-BGD74_sol-189 | 57179 | 94485044 | glycoprotein |
| Variola virus strain Bangladesh 1974 (nur islam) | Orthopoxvirus | 2215 | IFN-alpha/beta receptor | 584 | VARV-BGD74_nur-189 | 56783 | 94484648 | glycoprotein |
| Variola virus strain Bangladesh 1975 v75-550 Banu | Orthopoxvirus | 2198 | IFN-alpha/beta receptor | 584 | VARV-BGD75_Banu-192 | 53739 | 109724435 | glycoprotein |
| Variola virus strain Benin, Dahomey 1968 (v68-59) | Orthopoxvirus | 2224 | IFN-alpha/beta receptor | 584 | VARV-BEN68-198 | 58608 | 94483835 | glycoprotein |
| Variola virus strain Botswana 1972 (v72-143) | Orthopoxvirus | 2225 | IFN-alpha/beta receptor | 584 | VARV-BWA72-191 | 58810 | 94484038 | glycoprotein |
| Variola virus strain Botswana 1973 (v73-225) | Orthopoxvirus | 2226 | IFN-alpha/beta receptor | 584 | VARV-BWA73-191 | 59012 | 94484241 | glycoprotein |
| Variola virus strain Brazil 1966 (v66-39 Sao Paulo) | Orthopoxvirus | 2227 | IFN-alpha/beta receptor | 584 | VARV-BRA66-200 | 59223 | 94484448 | glycoprotein |
| Variola virus strain China Horn 1948 Sabin Lab July 1948 | Orthopoxvirus | 2203 | IFN-alpha/beta receptor | 584 | VARV-CHN48-194 | 54354 | 109724638 | glycoprotein |
| Variola virus strain Congo 1970 v70-46 Kinshasa | Orthopoxvirus | 2229 | IFN-alpha/beta receptor | 584 | VARV-COG70_46-192 | 59627 | 109724843 | glycoprotein |
| Variola virus strain Congo 9 1970 (v74-227 Gispen) | Orthopoxvirus | 2228 | IFN-alpha/beta receptor | 584 | VARV-COG70_227-191 | 59425 | 94485244 | glycoprotein |
| Variola virus strain Ethiopia 1972 (Eth16 R14-1X-72 Addis) | Orthopoxvirus | 2231 | IFN-alpha/beta receptor | 584 | VARV-ETH72_16-193 | 60066 | 94485447 | glycoprotein |

TABLE 9-continued

Viral Orthologous Clusters V2.0
(VOCs)
Interferonalpha-beta
Gene Results Table

| Genome name | Genus | Genome id | Ortholog Group Name | Ortholog Group ID | Gene number | Gene Id | Genbank id | Genbank name |
|---|---|---|---|---|---|---|---|---|
| Variola virus strain Ethiopia 1972 (Eth17 R14-1X-72 Addis) | Orthopoxvirus | 2232 | IFN-alpha/beta receptor | 584 | VARV-ETH72_17-191 | 60267 | 94485648 | glycoprotein |
| Variola virus strain Germany 1958 Heidelberg | Orthopoxvirus | 2233 | IFN-alpha/beta receptor | 584 | VARV-DEU58-191 | 60468 | 109725045 | glycoprotein |
| Variola virus strain Guinea 1969 (005) | Orthopoxvirus | 2234 | IFN-alpha/beta receptor | 584 | VARV-GIN69-196 | 60674 | 94485851 | glycoprotein |
| Variola virus strain India 1953 (Kali-Muthu-M50 Madras) | Orthopoxvirus | 2238 | IFN-alpha/beta receptor | 584 | VARV-IND53_mad-191 | 61481 | 94486054 | glycoprotein |
| Variola virus strain India 1953 (New Delhi) | Orthopoxvirus | 2239 | IFN-alpha/beta receptor | 584 | VARV-IND53_ndel-191 | 61682 | 94486256 | glycoprotein |
| Variola virus strain India 1964 7124 Vellore | Orthopoxvirus | 2240 | IFN-alpha/beta receptor | 584 | VARV-IND64_vel4-195 | 61888 | 109725251 | glycoprotein |
| Variola virus strain India 1964 7125 Vellore | Orthopoxvirus | 2241 | IFN-alpha/beta receptor | 584 | VARV-IND64_vel5-194 | 62092 | 109725456 | immunoglobulin superfamily secreted glycoprotein |
| Variola virus strain India 3 Major 1967 | Orthopoxvirus | 1483 | IFN-alpha/beta receptor | 584 | VARV-IND3_1967-191 | 39353 | 9627709 | B20R |
| Variola virus strain Iran 1972 2602 Tabriz | Orthopoxvirus | 2235 | IFN-alpha/beta receptor | 584 | VARV-IRN72-193 | 60878 | 109725658 | glycoprotein |
| Variola virus strain Japan 1946 (Yamada MS-2(A) Tokyo) | Orthopoxvirus | 2243 | IFN-alpha/beta receptor | 584 | VARV-JPN46_yam-191 | 62466 | 94486459 | glycoprotein |
| Variola virus strain Japan 1951 (Harper, Masterseed) | Orthopoxvirus | 2244 | IFN-alpha/beta receptor | 584 | VARV-JPN51_hrpr-190 | 62667 | 94486661 | glycoprotein |
| Variola virus strain Japan 1951 (Stillwell, Masterseed) | Orthopoxvirus | 2245 | IFN-alpha/beta receptor | 584 | VARV-JPN51_stwl-191 | 62869 | 94486864 | glycoprotein |
| Variola virus strain Korea 1947 (Lee, Masterseed) | Orthopoxvirus | 2236 | IFN-alpha/beta receptor | 584 | VARV-KOR47-192 | 61080 | 94487067 | glycoprotein |
| Variola virus strain Kuwait 1967 (K1629) | Orthopoxvirus | 2237 | IFN-alpha/beta receptor | 584 | VARV-KWT67-191 | 61281 | 94487269 | glycoprotein |
| Variola virus strain Nepal 1973 V73-175 | Orthopoxvirus | 2221 | IFN-alpha/beta receptor | 584 | VARV-NPL73-192 | 57982 | 109725860 | glycoprotein |
| Variola virus strain Niger 1969 (001, importation from Nigeria) | Orthopoxvirus | 2222 | IFN-alpha/beta receptor | 584 | VARV-NER69-198 | 58191 | 94487472 | glycoprotein |
| Variola virus strain Sierra Leone 1969 (V68-258) | Orthopoxvirus | 2223 | IFN-alpha/beta receptor | 584 | VARV-SLE68-197 | 58399 | 94488080 | glycoprotein |
| Variola virus strain Somalia 1977 (V77-1252) | Orthopoxvirus | 2218 | IFN-alpha/beta receptor | 584 | VARV-SOM77_1252-190 | 57378 | 94488282 | glycoprotein |
| Variola virus strain Somalia 1977 (V77-1605) | Orthopoxvirus | 2219 | IFN-alpha/beta receptor | 584 | VARV-SOM77_1605-190 | 57578 | 94488482 | glycoprotein |
| Variola virus strain Somalia 1977 V77-2479 | Orthopoxvirus | 2220 | IFN-alpha/beta receptor | 584 | VARV-SOM77_ali-192 | 57780 | 109726268 | glycoprotein |
| Variola virus strain South Africa 1965 (102 Natal, Ingwavuma) | Orthopoxvirus | 2210 | IFN-alpha/beta receptor | 584 | VARV-ZAF65_102-191 | 55763 | 94487675 | glycoprotein |
| Variola virus strain South Africa 1965 (103 Tvaal, Nelspruit) | Orthopoxvirus | 2211 | IFN-alpha/beta receptor | 584 | VARV-ZAF65_103-191 | 55964 | 94487876 | glycoprotein |
| Variola virus strain Sudan 1947 (Juba) | Orthopoxvirus | 2212 | IFN-alpha/beta receptor | 584 | VARV-SDN47_jub-190 | 56164 | 94488682 | immunoglobulin superfamily secreted glycoprotein |
| Variola virus strain Sudan 1947 (Rumbec) | Orthopoxvirus | 2213 | IFN-alpha/beta receptor | 584 | VARV-SDN47_rum-191 | 56365 | 94488884 | glycoprotein |
| Variola virus strain Sumatra 1970 V70-222 | Orthopoxvirus | 2208 | IFN-alpha/beta receptor | 584 | VARV-SUM70_222-192 | 55362 | 109726471 | glycoprotein |
| Variola virus strain Sumatra 1970 V70-228 | Orthopoxvirus | 2209 | IFN-alpha/beta receptor | 584 | VARV-SUM70_228-190 | 55562 | 94489084 | glycoprotein |
| Variola virus strain Syria 1972 V72-199 | Orthopoxvirus | 2206 | IFN-alpha/beta receptor | 584 | VARV-SYR72-193 | 54959 | 109726675 | glycoprotein |
| Variola virus strain Tanzania 1965 kembula | Orthopoxvirus | 2207 | IFN-alpha/beta receptor | 584 | VARV-TZA65-191 | 55160 | 94489282 | glycoprotein |
| Variola virus strain United Kingdom 1946 Harvey | Orthopoxvirus | 2204 | IFN-alpha/beta receptor | 584 | VARV-GBR44_harv-192 | 54557 | 94489485 | glycoprotein |
| Variola virus strain United Kingdom 1946 Hinden (Middlesex) | Orthopoxvirus | 2205 | IFN-alpha/beta receptor | 584 | VARV-GBR46_hind-190 | 54757 | 94489686 | glycoprotein |
| Variola virus strain United Kingdom 1947 Higgins (Staffordshire) | Orthopoxvirus | 2202 | IFN-alpha/beta receptor | 584 | VARV-GBR47_hig-191 | 54150 | 94489885 | glycoprotein |
| Variola virus strain United Kingdom 1952 Butler | Orthopoxvirus | 2200 | IFN-alpha/beta receptor | 584 | VARV-GBR52_but-200 | 53948 | 94490092 | glycoprotein |

TABLE 9-continued

Viral Orthologous Clusters V2.0
(VOCs)
Interferonalpha-beta
Gene Results Table

| Genome name | Genus | Genome id | Ortholog Group Name | Ortholog Group ID | Gene number | Gene Id | Genbank id | Genbank name |
|---|---|---|---|---|---|---|---|---|
| Variola virus strain Yugoslavia 1972 V72-164 | Orthopoxvirus | 2196 | IFN-alpha/beta receptor | 584 | VARV-YUG72-191 | 53334 | 94490295 | glycoprotein |
| Y TABLE 10-continued Viral Orthologous Clusters V2.0
(VOCs)
Semaphorin
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Afghanistan 1970 Variolator 4 | Orthopoxvirus | 2197 | Semaphorin | 295 | VARV-AFG70-154 | 53498 | 109724193 | semaphorin-like protein |
| Variola virus strain Afghanistan 1970 Variolator 4 | Orthopoxvirus | 2197 | Semaphorin | 295 | VARV-AFG70-155 | 53499 | 109724194 | semaphorin-like protein |
| Variola virus strain Bangladesh 1974 (Shahzaman) | Orthopoxvirus | 2216 | Semaphorin | 295 | VARV-BGD74_shz-153 | 56945 | 94484810 | semaphorin-like protein |
| Variola virus strain Bangladesh 1974 (Shahzaman) | Orthopoxvirus | 2216 | Semaphorin | 295 | VARV-BGD74_shz-154 | 56946 | 94484811 | semaphorin-like protein |
| Variola virus strain Bangladesh 1974 (Solaiman) | Orthopoxvirus | 2217 | Semaphorin | 295 | VARV-BGD74_sol-153 | 57143 | 94485008 | semaphorin-like protein |
| Variola virus strain Bangladesh 1974 (Solaiman) | Orthopoxvirus | 2217 | Semaphorin | 295 | VARV-BGD74_sol-154 | 57144 | 94485009 | semaphorin-like protein |
| Variola virus strain Bangladesh 1974 (nur islam) | Orthopoxvirus | 2215 | Semaphorin | 295 | VARV-BGD74_nur-153 | 56747 | 94484612 | semaphorin-like protein |
| Variola virus strain Bangladesh 1974 (nur islam) | Orthopoxvirus | 2215 | Semaphorin | 295 | VARV-BGD74_nur-154 | 56748 | 94484613 | semaphorin-like protein |
| Variola virus strain Bangladesh 1974 (nur islam) | Orthopoxvirus | 2215 | Semaphorin | 295 | VARV-BGD74_nur-155 | 56749 | 94484614 | type-II membrane protein |
| Variola virus strain Bangladesh 1975 v75-550 Banu | Orthopoxvirus | 2198 | Semaphorin | 295 | VARV-BGD75_Banu-153 | 53700 | 109724396 | semaphorin-like protein |
| Variola virus strain Bangladesh 1975 v75-550 Banu | Orthopoxvirus | 2198 | Semaphorin | 295 | VARV-BGD75_Banu-154 | 53701 | 109724397 | semaphorin-like protein |
| Variola virus strain Benin, Dahomey 1968 (v68-59) | Orthopoxvirus | 2224 | Semaphorin | 295 | VARV-BEN68-154 | 58564 | 94483794 | semaphorin-like protein |
| Variola virus strain Benin, Dahomey 1968 (v68-59) | Orthopoxvirus | 2224 | Semaphorin | 295 | VARV-BEN68-155 | 58565 | 94483795 | semaphorin-like protein |
| Variola virus strain Benin, Dahomey 1968 (v68-59) | Orthopoxvirus | 2224 | Semaphorin | 295 | VARV-BEN68-156 | 58566 | 94483796 | semaphorin-like protein |
| Variola virus strain Botswana 1972 (v72-143) | Orthopoxvirus | 2225 | Semaphorin | 295 | VARV-BWA72-153 | 58772 | 94484000 | semaphorin-like protein |
| Variola virus strain Botswana 1972 (v72-143) | Orthopoxvirus | 2225 | Semaphorin | 295 | VARV-BWA72-154 | 58773 | 94484001 | semaphorin-like protein |
| Variola virus strain Botswana 1973 (v73-225) | Orthopoxvirus | 2226 | Semaphorin | 295 | VARV-BWA73-153 | 58974 | 94484203 | semaphorin-like protein |
| Variola virus strain Botswana 1973 (v73-225) | Orthopoxvirus | 2226 | Semaphorin | 295 | VARV-BWA73-154 | 58975 | 94484204 | semaphorin-like protein |
| Variola virus strain Brazil 1966 (v66-39 Sao Paulo) | Orthopoxvirus | 2227 | Semaphorin | 295 | VARV-BRA66-157 | 59180 | 94484408 | semaphorin-like protein |
| Variola virus strain Brazil 1966 (v66-39 Sao Paulo) | Orthopoxvirus | 2227 | Semaphorin | 295 | VARV-BRA66-158 | 59181 | 94484409 | semaphorin-like protein |
| Variola virus strain Brazil 1966 (v66-39 Sao Paulo) | Orthopoxvirus | 2227 | Semaphorin | 295 | VARV-BRA66-159 | 59182 | 94484410 | semaphorin-like protein |
| Variola virus strain China Horn 1948 Sabin Lab July 1948 | Orthopoxvirus | 2203 | Semaphorin | 295 | VARV-CHN48-153 | 54313 | 109724598 | semaphorin-like protein |
| Variola virus strain China Horn 1948 Sabin Lab July 1948 | Orthopoxvirus | 2203 | Semaphorin | 295 | VARV-CHN48-154 | 54314 | 109724599 | semaphorin-like protein |
| Variola virus strain China Horn 1948 Sabin Lab July 1948 | Orthopoxvirus | 2203 | Semaphorin | 295 | VARV-CHN48-155 | 54315 | 109724600 | semaphorin-like protein |
| Variola virus strain Congo 1970 v70-46 Kinshasa | Orthopoxvirus | 2229 | Semaphorin | 295 | VARV-COG70_46-153 | 59588 | 109724803 | semaphorin-like protein |
| Variola virus strain Congo 1970 v70-46 Kinshasa | Orthopoxvirus | 2229 | Semaphorin | 295 | VARV-COG70_46-154 | 59589 | 109724804 | semaphorin-like protein |
| Variola virus strain Congo 9 1970 (v74-227 Gispen) | Orthopoxvirus | 2228 | Semaphorin | 295 | VARV-COG70_227-153 | 59387 | 94485206 | semaphorin-like protein |
| Variola virus strain Congo 9 1970 (v74-227 Gispen) | Orthopoxvirus | 2228 | Semaphorin | 295 | VARV-COG70_227-154 | 59388 | 94485207 | semaphorin-like protein |
| Variola virus strain Ethiopia 1972 (Eth16 R14-1X-72 Addis) | Orthopoxvirus | 2231 | Semaphorin | 295 | VARV-ETH72_16-154 | 60027 | 94485408 | semaphorin-like protein |
| Variola virus strain Ethiopia 1972 (Eth16 R14-1X-72 Addis) | Orthopoxvirus | 2231 | Semaphorin | 295 | VARV-ETH72_16-155 | 60028 | 94485409 | semaphorin-like protein |
| Variola virus strain Ethiopia 1972 (Eth17 R14-1X-72 Addis) | Orthopoxvirus | 2232 | Semaphorin | 295 | VARV-ETH72_17-154 | 60230 | 94485611 | semaphorin-like protein |
| Variola virus strain Ethiopia 1972 (Eth17 R14-1X-72 Addis) | Orthopoxvirus | 2232 | Semaphorin | 295 | VARV-ETH72_17-155 | 60231 | 94485612 | semaphorin-like protein |
| Variola virus strain Germany 1958 Heidelberg | Orthopoxvirus | 2233 | Semaphorin | 295 | VARV-DEU58-152 | 60429 | 109725006 | semaphorin-like protein |
| Variola virus strain Germany 1958 Heidelberg | Orthopoxvirus | 2233 | Semaphorin | 295 | VARV-DEU58-153 | 60430 | 109725007 | semaphorin-like protein |
| Variola virus strain Guinea 1969 (005) | Orthopoxvirus | 2234 | Semaphorin | 295 | VARV-GIN69-153 | 60631 | 94485811 | semaphorin-like protein |

TABLE 10-continued

Viral Orthologous Clusters V2.0
(VOCs)
Semaphorin
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Guinea 1969 (005) | Orthopoxvirus | 2234 | Semaphorin | 295 | VARV-GIN69-154 | 60632 | 94485812 | semaphorin-like protein |
| Variola virus strain Guinea 1969 (005) | Orthopoxvirus | 2234 | Semaphorin | 295 | VARV-GIN69-155 | 60633 | 94485813 | semaphorin-like protein |
| Variola virus strain India 1953 (Kali-Muthu-M50 Madras) | Orthopoxvirus | 2238 | Semaphorin | 295 | VARV-IND53_mad-153 | 61443 | 94486016 | semaphorin-like protein |
| Variola virus strain India 1953 (Kali-Muthu-M50 Madras) | Orthopoxvirus | 2238 | Semaphorin | 295 | VARV-IND53_mad-154 | 61444 | 94486017 | semaphorin-like protein |
| Variola virus strain India 1953 (Kali-Muthu-M50 Madras) | Orthopoxvirus | 2238 | Semaphorin | 295 | VARV-IND53_mad-155 | 61445 | 94486018 | semaphorin-like protein |
| Variola virus strain India 1953 (New Delhi) | Orthopoxvirus | 2239 | Semaphorin | 295 | VARV-IND53_ndel-152 | 61643 | 94486217 | semaphorin-like protein |
| Variola virus strain India 1953 (New Delhi) | Orthopoxvirus | 2239 | Semaphorin | 295 | VARV-IND53_ndel-153 | 61644 | 94486218 | semaphorin-like protein |
| Variola virus strain India 1953 (New Delhi) | Orthopoxvirus | 2239 | Semaphorin | 295 | VARV-IND53_ndel-154 | 61645 | 94486219 | semaphorin-like protein |
| Variola virus strain India 1964 7124 Vellore | Orthopoxvirus | 2240 | Semaphorin | 295 | VARV-IND64_vel4-154 | 61847 | 109725210 | semaphorin-like protein |
| Variola virus strain India 1964 7124 Vellore | Orthopoxvirus | 2240 | Semaphorin | 295 | VARV-IND64_vel4-155 | 61848 | 109725211 | semaphorin-like protein |
| Variola virus strain India 1964 7124 Vellore | Orthopoxvirus | 2240 | Semaphorin | 295 | VARV-IND64_vel4-156 | 61849 | 109725212 | semaphorin-like protein |
| Variola virus strain India 1964 7125 Vellore | Orthopoxvirus | 2241 | Semaphorin | 295 | VARV-IND64_vel5-153 | 62051 | 109725415 | semaphorin-like protein |
| Variola virus strain India 1964 7125 Vellore | Orthopoxvirus | 2241 | Semaphorin | 295 | VARV-IND64_vel5-154 | 62052 | 109725416 | semaphorin-like protein |
| Variola virus strain India 1964 7125 Vellore | Orthopoxvirus | 2241 | Semaphorin | 295 | VARV-IND64_vel5-155 | 62053 | 109725417 | semaphorin-like protein |
| Variola virus strain India 3 Major 1967 | Orthopoxvirus | 1483 | Semaphorin | 295 | VARV-IND3_1967-151 | 39313 | 9627669 | A42R |
| Variola virus strain India 3 Major 1967 | Orthopoxvirus | 1483 | Semaphorin | 295 | VARV-IND3_1967-152 | 39314 | 9627670 | A43R |
| Variola virus strain India 3 Major 1967 | Orthopoxvirus | 1483 | Semaphorin | 295 | VARV-IND3_1967-153 | 39315 | 9627671 | A44R |
| Variola virus strain Iran 1972 2602 Tabriz | Orthopoxvirus | 2235 | Semaphorin | 295 | VARV-IRN72-153 | 60838 | 109725618 | semaphorin-like protein |
| Variola virus strain Iran 1972 2602 Tabriz | Orthopoxvirus | 2235 | Semaphorin | 295 | VARV-IRN72-154 | 60839 | 109725619 | semaphorin-like protein |
| Variola virus strain Iran 1972 2602 Tabriz | Orthopoxvirus | 2235 | Semaphorin | 295 | VARV-IRN72-155 | 60840 | 109725620 | semaphorin-like protein |
| Variola virus strain Japan 1946 (Yamada MS-2(A) Tokyo) | Orthopoxvirus | 2243 | Semaphorin | 295 | VARV-JPN46_yam-152 | 62427 | 94486420 | semaphorin-like protein |
| Variola virus strain Japan 1946 (Yamada MS-2(A) Tokyo) | Orthopoxvirus | 2243 | Semaphorin | 295 | VARV-JPN46_yam-153 | 62428 | 94486421 | semaphorin-like protein |
| Variola virus strain Japan 1946 (Yamada MS-2(A) Tokyo) | Orthopoxvirus | 2243 | Semaphorin | 295 | VARV-JPN46_yam-154 | 62429 | 94486422 | semaphorin-like protein |
| Variola virus strain Japan 1946 (Yamada MS-2(A) Tokyo) | Orthopoxvirus | 2243 | Semaphorin | 295 | VARV-JPN46_yam-155 | 62430 | 94486423 | type-II membrane protein |
| Variola virus strain Japan 1951 (Harper, Masterseed) | Orthopoxvirus | 2244 | Semaphorin | 295 | VARV-JPN51_hrpr-152 | 62629 | 94486623 | semaphorin-like protein |
| Variola virus strain Japan 1951 (Harper, Masterseed) | Orthopoxvirus | 2244 | Semaphorin | 295 | VARV-JPN51_hrpr-153 | 62630 | 94486624 | semaphorin-like protein |
| Variola virus strain Japan 1951 (Harper, Masterseed) | Orthopoxvirus | 2244 | Semaphorin | 295 | VARV-JPN51_hrpr-154 | 62631 | 94486625 | semaphorin-like protein |
| Variola virus strain Japan 1951 (Harper, Masterseed) | Orthopoxvirus | 2244 | Semaphorin | 295 | VARV-JPN51_hrpr-155 | 62632 | 94486626 | type-II membrane protein |
| Variola virus strain Japan 1951 (Stillwell, Masterseed) | Orthopoxvirus | 2245 | Semaphorin | 295 | VARV-JPN51_stwl-152 | 62830 | 94486825 | semaphorin-like protein |
| Variola virus strain Japan 1951 (Stillwell, Masterseed) | Orthopoxvirus | 2245 | Semaphorin | 295 | VARV-JPN51_stwl-153 | 62831 | 94486826 | semaphorin-like protein |
| Variola virus strain Japan 1951 (Stillwell, Masterseed) | Orthopoxvirus | 2245 | Semaphorin | 295 | VARV-JPN51_stwl-154 | 62832 | 94486827 | semaphorin-like protein |
| Variola virus strain Japan 1951 (Stillwell, Masterseed) | Orthopoxvirus | 2245 | Semaphorin | 295 | VARV-JPN51_stwl-155 | 62833 | 94486828 | type-II membrane protein |
| Variola virus strain Korea 1947 (Lee, Masterseed) | Orthopoxvirus | 2236 | Semaphorin | 295 | VARV-KOR47-153 | 61041 | 94487028 | semaphorin-like protein |
| Variola virus strain Korea 1947 (Lee, Masterseed) | Orthopoxvirus | 2236 | Semaphorin | 295 | VARV-KOR47-154 | 61042 | 94487029 | semaphorin-like protein |

TABLE 10-continued

Viral Orthologous Clusters V2.0
(VOCs)
Semaphorin
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Korea 1947 (Lee, Masterseed) | Orthopoxvirus | 2236 | Semaphorin | 295 | VARV-KOR47-155 | 61043 | 94487030 | semaphorin-like protein |
| Variola virus strain Korea 1947 (Lee, Masterseed) | Orthopoxvirus | 2236 | Semaphorin | 295 | VARV-KOR47-156 | 61044 | 94487031 | type-II membrane protein |
| Variola virus strain Kuwait 1967 (K1629) | Orthopoxvirus | 2237 | Semaphorin | 295 | VARV-KWT67-153 | 61243 | 94487231 | semaphorin-like protein |
| Variola virus strain Kuwait 1967 (K1629) | Orthopoxvirus | 2237 | Semaphorin | 295 | VARV-KWT67-154 | 61244 | 94487232 | semaphorin-like protein |
| Variola virus strain Kuwait 1967 (K1629) | Orthopoxvirus | 2237 | Semaphorin | 295 | VARV-KWT67-155 | 61245 | 94487233 | semaphorin-like protein |
| Variola virus strain Nepal 1973 V73-175 | Orthopoxvirus | 2221 | Semaphorin | 295 | VARV-NPL73-153 | 57943 | 109725822 | semaphorin-like protein |
| Variola virus strain Nepal 1973 V73-175 | Orthopoxvirus | 2221 | Semaphorin | 295 | VARV-NPL73-154 | 57944 | 109725823 | semaphorin-like protein |
| Variola virus strain Nepal 1973 V73-175 | Orthopoxvirus | 2221 | Semaphorin | 295 | VARV-NPL73-155 | 57945 | 109725824 | type-II membrane protein |
| Variola virus strain Niger 1969 (001, importation from Nigeria) | Orthopoxvirus | 2222 | Semaphorin | 295 | VARV-NER69-155 | 58148 | 94487432 | semaphorin-like protein |
| Variola virus strain Niger 1969 (001, importation from Nigeria) | Orthopoxvirus | 2222 | Semaphorin | 295 | VARV-NER69-156 | 58149 | 94487433 | semaphorin-like protein |
| Variola virus strain Niger 1969 (001, importation from Nigeria) | Orthopoxvirus | 2222 | Semaphorin | 295 | VARV-NER69-157 | 58150 | 94487434 | semaphorin-like protein |
| Variola virus strain Sierra Leone 1969 (V68-258) | Orthopoxvirus | 2223 | Semaphorin | 295 | VARV-SLE68-154 | 58356 | 94488040 | semaphorin-like protein |
| Variola virus strain Sierra Leone 1969 (V68-258) | Orthopoxvirus | 2223 | Semaphorin | 295 | VARV-SLE68-155 | 58357 | 94488041 | semaphorin-like protein |
| Variola virus strain Sierra Leone 1969 (V68-258) | Orthopoxvirus | 2223 | Semaphorin | 295 | VARV-SLE68-156 | 58358 | 94488042 | semaphorin-like protein |
| Variola virus strain Somalia 1977 (V77-1252) | Orthopoxvirus | 2218 | Semaphorin | 295 | VARV-SOM77_1252-153 | 57341 | 94488245 | semaphorin-like protein |
| Variola virus strain Somalia 1977 (V77-1252) | Orthopoxvirus | 2218 | Semaphorin | 295 | VARV-SOM77_1252-154 | 57342 | 94488246 | semaphorin-like protein |
| Variola virus strain Somalia 1977 (V77-1252) | Orthopoxvirus | 2218 | Semaphorin | 295 | VARV-SOM77_1252-155 | 57343 | 94488247 | type-II membrane protein |
| Variola virus strain Somalia 1977 (V77-1605) | Orthopoxvirus | 2219 | Semaphorin | 295 | VARV-SOM77_1605-153 | 57541 | 94488445 | semaphorin-like protein |
| Variola virus strain Somalia 1977 (V77-1605) | Orthopoxvirus | 2219 | Semaphorin | 295 | VARV-SOM77_1605-154 | 57542 | 94488446 | semaphorin-like protein |
| Variola virus strain Somalia 1977 (V77-1605) | Orthopoxvirus | 2219 | Semaphorin | 295 | VARV-SOM77_1605-155 | 57543 | 94488447 | type-II membrane protein |
| Variola virus strain Somalia 1977 V77-2479 | Orthopoxvirus | 2220 | Semaphorin | 295 | VARV-SOM77_ali-153 | 57741 | 109726229 | semaphorin-like protein |
| Variola virus strain Somalia 1977 V77-2479 | Orthopoxvirus | 2220 | Semaphorin | 295 | VARV-SOM77_ali-154 | 57742 | 109726230 | semaphorin-like protein |
| Variola virus strain Somalia 1977 V77-2479 | Orthopoxvirus | 2220 | Semaphorin | 295 | VARV-SOM77_ali-155 | 57743 | 109726231 | type-II membrane protein |
| Variola virus strain South Africa 1965 (102 Natal, Ingwavuma) | Orthopoxvirus | 2210 | Semaphorin | 295 | VARV-ZAF65_102-153 | 55725 | 94487637 | semaphorin-like protein |
| Variola virus strain South Africa 1965 (102 Natal, Ingwavuma) | Orthopoxvirus | 2210 | Semaphorin | 295 | VARV-ZAF65_102-154 | 55726 | 94487638 | semaphorin-like protein |
| Variola virus strain South Africa 1965 (102 Natal, Ingwavuma) | Orthopoxvirus | 2210 | Semaphorin | 295 | VARV-ZAF65_102-155 | 55727 | 94487639 | type-II membrane protein |
| Variola virus strain South Africa 1965 (103 Tvaal, Nelspruit) | Orthopoxvirus | 2211 | Semaphorin | 295 | VARV-ZAF65_103-153 | 55926 | 94487838 | semaphorin-like protein |
| Variola virus strain South Africa 1965 (103 Tvaal, Nelspruit) | Orthopoxvirus | 2211 | Semaphorin | 295 | VARV-ZAF65_103-154 | 55927 | 94487839 | semaphorin-like protein |
| Variola virus strain South Africa 1965 (103 Tvaal, Nelspruit) | Orthopoxvirus | 2211 | Semaphorin | 295 | VARV-ZAF65_103-155 | 55928 | 94487840 | type-II membrane protein |
| Variola virus strain Sudan 1947 (Juba) | Orthopoxvirus | 2212 | Semaphorin | 295 | VARV-SDN47_jub-153 | 56127 | 94488645 | semaphorin-like protein |
| Variola virus strain Sudan 1947 (Juba) | Orthopoxvirus | 2212 | Semaphorin | 295 | VARV-SDN47_jub-154 | 56128 | 94488646 | semaphorin-like protein |
| Variola virus strain Sudan 1947 (Rumbec) | Orthopoxvirus | 2213 | Semaphorin | 295 | VARV-SDN47_rum-153 | 56327 | 94488846 | semaphorin-like protein |

TABLE 10-continued

Viral Orthologous Clusters V2.0
(VOCs)
Semaphorin
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Sudan 1947 (Rumbec) | Orthopoxvirus | 2213 | Semaphorin | 295 | VARV-SDN47_rum-154 | 56328 | 94488847 | semaphorin-like protein |
| Variola virus strain Sumatra 1970 V70-222 | Orthopoxvirus | 2208 | Semaphorin | 295 | VARV-SUM70_222-151 | 55321 | 109726430 | semaphorin-like protein |
| Variola virus strain Sumatra 1970 V70-222 | Orthopoxvirus | 2208 | Semaphorin | 295 | VARV-SUM70_222-152 | 55322 | 109726431 | semaphorin-like protein |
| Variola virus strain Sumatra 1970 V70-222 | Orthopoxvirus | 2208 | Semaphorin | 295 | VARV-SUM70_222-153 | 55323 | 109726432 | semaphorin-like protein |
| Variola virus strain Sumatra 1970 V70-228 | Orthopoxvirus | 2209 | Semaphorin | 295 | VARV-SUM70_228-151 | 55523 | 94489045 | semaphorin-like protein |
| Variola virus strain Sumatra 1970 V70-228 | Orthopoxvirus | 2209 | Semaphorin | 295 | VARV-SUM70_228-152 | 55524 | 94489046 | semaphorin-like protein |
| Variola virus strain Sumatra 1970 V70-228 | Orthopoxvirus | 2209 | Semaphorin | 295 | VARV-SUM70_228-153 | 55525 | 94489047 | semaphorin-like protein |
| Variola virus strain Syria 1972 V72-199 | Orthopoxvirus | 2206 | Semaphorin | 295 | VARV-SYR72-153 | 54919 | 109726635 | semaphorin-like protein |
| Variola virus strain Syria 1972 V72-199 | Orthopoxvirus | 2206 | Semaphorin | 295 | VARV-SYR72-154 | 54920 | 109726636 | semaphorin-like protein |
| Variola virus strain Syria 1972 V72-199 | Orthopoxvirus | 2206 | Semaphorin | 295 | VARV-SYR72-155 | 54921 | 109726637 | semaphorin-like protein |
| Variola virus strain Tanzania 1965 kembula | Orthopoxvirus | 2207 | Semaphorin | 295 | VARV-TZA65-153 | 55122 | 94489246 | semaphorin-like protein |
| Variola virus strain Tanzania 1965 kembula | Orthopoxvirus | 2207 | Semaphorin | 295 | VARV-TZA65-154 | 55123 | 94489247 | semaphorin-like protein |
| Variola virus strain Tanzania 1965 kembula | Orthopoxvirus | 2207 | Semaphorin | 295 | VARV-TZA65-155 | 55124 | 94489248 | type-II membrane protein |
| Variola virus strain United Kingdom 1946 Harvey | Orthopoxvirus | 2204 | Semaphorin | 295 | VARV-GBR44_harv-153 | 54518 | 94489446 | semaphorin-like protein |
| Variola virus strain United Kingdom 1946 Harvey | Orthopoxvirus | 2204 | Semaphorin | 295 | VARV-GBR44_harv-154 | 54519 | 94489447 | semaphorin-like protein |
| Variola virus strain United Kingdom 1946 Harvey | Orthopoxvirus | 2204 | Semaphorin | 295 | VARV-GBR44_harv-155 | 54520 | 94489448 | semaphorin-like protein |
| Variola virus strain United Kingdom 1946 Hinden (Middlesex) | Orthopoxvirus | 2205 | Semaphorin | 295 | VARV-GBR46_hind-152 | 54719 | 94489648 | semaphorin-like protein |
| Variola virus strain United Kingdom 1946 Hinden (Middlesex) | Orthopoxvirus | 2205 | Semaphorin | 295 | VARV-GBR46_hind-153 | 54720 | 94489649 | semaphorin-like protein |
| Variola virus strain United Kingdom 1946 Hinden (Middlesex) | Orthopoxvirus | 2205 | Semaphorin | 295 | VARV-GBR46_hind-154 | 54721 | 94489650 | semaphorin-like protein |
| Variola virus strain United Kingdom 1947 Higgins (Staffordshire) | Orthopoxvirus | 2202 | Semaphorin | 295 | VARV-GBR47_hig-153 | 54112 | 94489848 | semaphorin-like protein |
| Variola virus strain United Kingdom 1947 Higgins (Staffordshire) | Orthopoxvirus | 2202 | Semaphorin | 295 | VARV-GBR47_hig-154 | 54113 | 94489849 | semaphorin-like protein |
| Variola virus strain United Kingdom 1952 Butler | Orthopoxvirus | 2200 | Semaphorin | 295 | VARV-GBR52_but-157 | 53905 | 94490052 | semaphorin-like protein |
| Variola virus strain United Kingdom 1952 Butler | Orthopoxvirus | 2200 | Semaphorin | 295 | VARV-GBR52_but-158 | 53906 | 94490053 | semaphorin-like protein |
| Variola virus strain United Kingdom 1952 Butler | Orthopoxvirus | 2200 | Semaphorin | 295 | VARV-GBR52_but-159 | 53907 | 94490054 | semaphorin-like protein |
| Variola virus strain Yugoslavia 1972 V72-164 | Orthopoxvirus | 2196 | Semaphorin | 295 | VARV-YUG72-153 | 53296 | 94490257 | semaphorin-like protein |
| Variola virus strain Yugoslavia 1972 V72-164 | Orthopoxvirus | 2196 | Semaphorin | 295 | VARV-YUG72-154 | 53297 | 94490258 | semaphorin-like protein |
| Variola virus strain Yugoslavia 1972 V72-164 | Orthopoxvirus | 2196 | Semaphorin | 295 | VARV-YUG72-155 | 53298 | 94490259 | semaphorin-like protein |

TABLE 11

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Camelpox virus strain CMS | Orthopoxvirus | 1493 | TNF receptor (CrmB) | 642 | CMLV-CMS-002 | 41098 | 19717931 | 2L |

TABLE 11-continued

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Camelpox virus strain CMS | Orthopoxvirus | 1493 | TNF-alpha receptor (CPXV-GRI-K3R) | 742 | CMLV-CMS-009 | 41105 | 19717938 | 7L |
| Camelpox virus strain CMS | Orthopoxvirus | 1493 | TNF receptor (CrmB) | 642 | CMLV-CMS-265 | 41361 | 19718193 | R |
| Camelpox virus strain M96 | Orthopoxvirus | 1491 | TNF receptor (CrmB) | 642 | CMLV-M96-002 | 40708 | 18640447 | 2 |
| Camelpox virus strain M96 | Orthopoxvirus | 1491 | TNF-alpha receptor (CPXV-GRI-K3R) | 742 | CMLV-M96-007 | 40713 | 18640241 | 7 |
| Camelpox virus strain M96 | Orthopoxvirus | 1491 | TNF receptor (CrmB) | 642 | CMLV-M96-212 | 40918 | 18640444 | 210 |
| Canarypox virus strain ATCC VR111 | Avipoxvirus | 1506 | TNF receptor (CrmB) | 642 | CNPV-VR111-086 | 43559 | 40556024 | 86 |
| Cowpox virus strain Brighton Red | Orthopoxvirus | 1496 | TNF receptor (CrmB) | 642 | CPXV-BR-005 | 41704 | 20178588 | 5 |
| Cowpox virus strain Brighton Red | Orthopoxvirus | 1496 | TNF receptor (CrmB) | 642 | CPXV-BR-014 | 41713 | 20178382 | 014f |
| Cowpox virus strain Brighton Red | Orthopoxvirus | 1496 | TNF receptor (CrmC) | 712 | CPXV-BR-197 | 41896 | 20178552 | 191 |
| Cowpox virus strain Brighton Red | Orthopoxvirus | 1496 | TNF receptor (CrmD) | 752 | CPXV-BR-227 | 41926 | 20178580 | 221 |
| Cowpox virus strain Brighton Red | Orthopoxvirus | 1496 | TNF receptor (CrmB) | 642 | CPXV-BR-232 | 41931 | 20178584 | 226 |
| Cowpox virus strain GRI-90 | Orthopoxvirus | 1501 | TNF receptor (CrmB) | 642 | CPXV-GRI-002 | 42659 | 30519407 | D2L |
| Cowpox virus strain GRI-90 | Orthopoxvirus | 1501 | TNF receptor (CrmB) | 642 | CPXV-GRI-012 | 42669 | 1808601 | D12L |
| Cowpox virus strain GRI-90 | Orthopoxvirus | 1501 | TNF receptor (CrmC) | 712 | CPXV-GRI-180 | 42837 | 30519548 | A56R |
| Cowpox virus strain GRI-90 | Orthopoxvirus | 1501 | TNF receptor (CrmD) | 752 | CPXV-GRI-207 | 42864 | 30519575 | K2R |
| Cowpox virus strain GRI-90 | Orthopoxvirus | 1501 | TNF-alpha receptor (CPXV-GRI-K3R) | 742 | CPXV-GRI-208 | 42865 | 30519576 | K3R |
| Cowpox virus strain GRI-90 | Orthopoxvirus | 1501 | TNF receptor (CrmB) | 642 | CPXV-GRI-213 | 42870 | 30519581 | I4R |
| Cowpox virus strain Germany 91-3 | Orthopoxvirus | 2214 | TNF receptor (CrmB) | 642 | CPXV-GER91-002 | 56377 | 90660235 | TNF-alpha-receptor-like protein |
| Cowpox virus strain Germany 91-3 | Orthopoxvirus | 2214 | TNF receptor (CrmB) | 642 | CPXV-GER91-012 | 56387 | 90660245 | TNF-alpha-receptor-like protein |
| Cowpox virus strain Germany 91-3 | Orthopoxvirus | 2214 | TNF receptor (CrmC) | 712 | CPXV-GER91-179 | 56554 | 90660412 | secreted TNF-receptor-like protein |
| Cowpox virus strain Germany 91-3 | Orthopoxvirus | 2214 | TNF receptor (CrmD) | 752 | CPXV-GER91-209 | 56584 | 90660442 | Crm-B secreted TNF-alpha-receptor-like protein |
| Cowpox virus strain Germany 91-3 | Orthopoxvirus | 2214 | TNF receptor (CrmD) | 752 | CPXV-GER91-210 | 56585 | 90660443 | Crm-B secreted TNF-alpha-receptor-like protein |
| Cowpox virus strain Germany 91-3 | Orthopoxvirus | 2214 | TNF-alpha receptor (CPXV-GRI-K3R) | 742 | CPXV-GER91-211 | 56586 | 90660444 | TNF-alpha-receptor-like protein |
| Cowpox virus strain Germany 91-3 | Orthopoxvirus | 2214 | TNF receptor (CrmB) | 642 | CPXV-GER91-218 | 56593 | 90660451 | Crm-B secreted TNF-alpha-receptor-like protein |
| Deerpox virus strain W-1170-84 | Unclassified | 1516 | Secreted TNF binding protein | 725 | DPV-W1170_84-008 | 45291 | 0 | 8 |
| Deerpox virus strain W-1170-84 | Unclassified | 1516 | TNF receptor (CrmB) | 642 | DPV-W1170_84-016 | 45299 | 0 | 16 |

TABLE 11-continued

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Deerpox virus strain W-848-83 | Unclassified | 1515 | Secreted TNF binding protein | 725 | DPV-W848_83-008 | 45121 | 62637387 | 8 |
| Deerpox virus strain W-848-83 | Unclassified | 1515 | TNF receptor (CrmB) | 642 | DPV-W848_83-016 | 45129 | 62637395 | 16 |
| Ectromelia virus strain Moscow | Orthopoxvirus | 1492 | TNF receptor (CrmD) | 752 | ECTV-Mos-003 | 40922 | 22164610 | 3 |
| Ectromelia virus strain Moscow | Orthopoxvirus | 1492 | TNF receptor (CrmB) | 642 | ECTV-Mos-008 | 40927 | 22164615 | 8 |
| Ectromelia virus strain Moscow | Orthopoxvirus | 1492 | TNF receptor (CrmD) | 752 | ECTV-Mos-175 | 41094 | 22164605 | 170 |
| Ectromelia virus strain Naval | Orthopoxvirus | 1499 | TNF receptor (CrmD) | 752 | ECTV-Nav-003 | 42258 | 0 | 6_177 |
| Ectromelia virus strain Naval | Orthopoxvirus | 1499 | TNF receptor (CrmB) | 642 | ECTV-Nav-007 | 42262 | 0 | 12 |
| Ectromelia virus strain Naval | Orthopoxvirus | 1499 | TNF receptor (CrmD) | 752 | ECTV-Nav-180 | 42435 | 0 | E6 |
| Horsepox virus strain MNR-76 | Orthopoxvirus | 2230 | TNF receptor (CrmB) | 642 | HSPV-MNR76-003 | 59640 | 1.11E+08 | HSPV003 |
| Horsepox virus strain MNR-76 | Orthopoxvirus | 2230 | TNF receptor (CrmB) | 642 | HSPV-MNR76-011 | 59648 | 1.11E+08 | HSPV009 |
| Horsepox virus strain MNR-76 | Orthopoxvirus | 2230 | TNF receptor (CrmC) | 712 | HSPV-MNR76-198 | 59835 | 1.11E+08 | HSPV175 |
| Horsepox virus strain MNR-76 | Orthopoxvirus | 2230 | TNF receptor (CrmB) | 642 | HSPV-MNR76-234 | 59871 | 1.11E+08 | HSPV205 |
| Monkeypox Virus strain Walter Reed 267 | Orthopoxvirus | 1502 | TNF receptor (CrmB) | 642 | MPXV-WR267-002 | 42873 | 0 | 2 |
| Monkeypox Virus strain Walter Reed 267 | Orthopoxvirus | 1502 | TNF receptor (CrmB) | 642 | MPXV-WR267-177 | 43048 | 0 | 176 |
| Monkeypox virus strain COP-58 | Orthopoxvirus | 1520 | TNF receptor (CrmB) | 642 | MPXV-COP58-002 | 46307 | 59858808 | 2 |
| Monkeypox virus strain COP-58 | Orthopoxvirus | 1520 | TNF receptor (CrmB) | 642 | MPXV-COP58-176 | 46481 | 59858982 | 176 |
| Monkeypox virus strain Congo_2003_358 | Orthopoxvirus | 1524 | TNF receptor (CrmB) | 642 | MPXV-COG_2003_358-002 | 47061 | 68448878 | 2 |
| Monkeypox virus strain Congo_2003_358 | Orthopoxvirus | 1524 | TNF-alpha receptor (CPXV-GRI-K3R) | 742 | MPXV-COG_2003_358-192 | 47251 | 68449068 | 198 |
| Monkeypox virus strain Congo_2003_358 | Orthopoxvirus | 1524 | TNF receptor (CrmB) | 642 | MPXV-COG_2003_358-199 | 47258 | 68449075 | 205 |
| Monkeypox virus strain Liberia_1970_184 | Orthopoxvirus | 1525 | TNF receptor (CrmB) | 642 | MPXV-LBR_1970_184-002 | 47261 | 68449282 | 2 |
| Monkeypox virus strain Liberia_1970_184 | Orthopoxvirus | 1525 | TNF-alpha receptor (CPXV-GRI-K3R) | 742 | MPXV-LBR_1970_184-191 | 47450 | 68449471 | 198 |
| Monkeypox virus strain Liberia_1970_184 | Orthopoxvirus | 1525 | TNF receptor (CrmB) | 642 | MPXV-LBR_1970_184-197 | 47456 | 68449477 | 205 |
| Monkeypox virus strain Sierra Leone | Orthopoxvirus | 1521 | TNF receptor (CrmB) | 642 | MPXV-SLE-002 | 46484 | 58220472 | 2 |
| Monkeypox virus strain Sierra Leone | Orthopoxvirus | 1521 | TNF receptor (CrmB) | 642 | MPXV-SLE-176 | 46658 | 58220646 | 176 |
| Monkeypox virus strain USA_2003_039 | Orthopoxvirus | 1526 | TNF receptor (CrmB) | 642 | MPXV-USA_2003_039-002 | 47459 | 68449481 | 2 |
| Monkeypox virus strain USA_2003_039 | Orthopoxvirus | 1526 | TNF-alpha receptor (CPXV-GRI-K3R) | 742 | MPXV-USA_2003_039-191 | 47648 | 68449670 | 198 |
| Monkeypox virus strain USA_2003_039 | Orthopoxvirus | 1526 | TNF receptor (CrmB) | 642 | MPXV-USA_2003_039-197 | 47654 | 68449676 | 205 |
| Monkeypox virus strain USA_2003_044 | Orthopoxvirus | 1522 | TNF receptor (CrmB) | 642 | MPXV-USA_2003_044-002 | 46661 | 68448679 | 2 |
| Monkeypox virus strain USA_2003_044 | Orthopoxvirus | 1522 | TNF-alpha receptor (CPXV-GRI-K3R) | 742 | MPXV-USA_2003_044-191 | 46850 | 68448868 | 198 |

TABLE 11-continued

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Monkeypox virus strain USA_2003_044 | Orthopoxvirus | 1522 | TNF receptor (CrmB) | 642 | MPXV-USA_2003_044-197 | 46856 | 68448874 | 205 |
| Monkeypox virus strain Zaire | Orthopoxvirus | 1489 | TNF receptor (CrmB) | 642 | MPXV-ZAR-002 | 40363 | 17974915 | J2L |
| Monkeypox virus strain Zaire | Orthopoxvirus | 1489 | TNF-alpha receptor (CPXV-GRI-K3R) | 742 | MPXV-ZAR-186 | 40547 | 17975096 | K1R |
| Monkeypox virus strain Zaire | Orthopoxvirus | 1489 | TNF receptor (CrmB) | 642 | MPXV-ZAR-193 | 40554 | 17975103 | J2R |
| Monkeypox virus strain Zaire_1979-005 | Orthopoxvirus | 1523 | TNF receptor (CrmB) | 642 | MPXV-ZAR_1979_005-002 | 46859 | 68449079 | 2 |
| Monkeypox virus strain Zaire_1979-005 | Orthopoxvirus | 1523 | TNF-alpha receptor (CPXV-GRI-K3R) | 742 | MPXV-ZAR_1979_005-194 | 47051 | 68449271 | 198 |
| Monkeypox virus strain Zaire_1979-005 | Orthopoxvirus | 1523 | TNF receptor (CrmB) | 642 | MPXV-ZAR_1979_005-201 | 47058 | 68449278 | 205 |
| Myxoma virus strain Lausanne | Leporipoxvirus | 1479 | TNF receptor (M-T2) | 558 | MYXV-Lau-003 | 38428 | 9633794 | m002L |
| Myxoma virus strain Lausanne | Leporipoxvirus | 1479 | TNF receptor (M-T2) | 558 | MYXV-Lau-169 | 38593 | 9633635 | M_T2 |
| Rabbit fibroma virus strain Kasza | Leporipoxvirus | 1480 | TNF receptor (M-T2) | 558 | SFV-Kas-002 | 38597 | 6578530 | gp002L |
| Rabbit fibroma virus strain Kasza | Leporipoxvirus | 1480 | TNF receptor (M-T2) | 558 | SFV-Kas-165 | 38760 | 9633970 | s002R |
| Rabbitpox virus strain Utrecht | Orthopoxvirus | 1494 | TNF receptor (CrmC) | 712 | RPXV-Utr-163 | 41525 | 44971524 | 161 |
| Swinepox virus strain Nebraska 17077-99 | Suipoxvirus | 1490 | Secreted TNF binding protein | 725 | SWPV-Neb-003 | 40558 | 18640089 | 3 |
| Swinepox virus strain Nebraska 17077-99 | Suipoxvirus | 1490 | Secreted TNF binding protein | 725 | SWPV-Neb-149 | 40704 | 18640234 | 148 |
| Tanapox virus strain Kenya | Yatapoxvirus | 3496 | Secreted TNF binding protein | 725 | TANV-KEN-002 | 67458 | 1.47E+08 | 2L |
| Tanapox virus strain isolate TPV-RoC | Yatapoxvirus | 3497 | Secreted TNF binding protein | 725 | TANV-COD-002 | 67538 | 1.47E+08 | 2L |
| Taterapox virus strain Dahomey 1968 | Orthopoxvirus | 2195 | TNF receptor (CrmB) | 642 | TATV-DAH68-004 | 52922 | 1.13E+08 | TNF-alpha-receptor-like protein |
| Taterapox virus strain Dahomey 1968 | Orthopoxvirus | 2195 | TNF receptor (CrmB) | 642 | TATV-DAH68-005 | 52923 | 1.13E+08 | TNF-alpha-receptor-like protein |
| Taterapox virus strain Dahomey 1968 | Orthopoxvirus | 2195 | TNF receptor (CrmB) | 642 | TATV-DAH68-221 | 53139 | 1.13E+08 | TNF-alpha-receptor-like protein |
| Taterapox virus strain Dahomey 1968 | Orthopoxvirus | 2195 | TNF receptor (CrmB) | 642 | TATV-DAH68-222 | 53140 | 1.13E+08 | TNF-alpha-receptor-like protein |
| Vaccinia virus strain 3737 | Orthopoxvirus | 1528 | TNF receptor (CrmB) | 642 | VACV-3737-002 | 47790 | 88900618 | 193 |
| Vaccinia virus strain 3737 | Orthopoxvirus | 1528 | TNF receptor (CrmB) | 642 | VACV-3737-003 | 47791 | 88900619 | 2 |
| Vaccinia virus strain 3737 | Orthopoxvirus | 1528 | TNF receptor (CrmC) | 712 | VACV-3737-180 | 47968 | 88900796 | 207 |
| Vaccinia virus strain Acambis 2000 | Orthopoxvirus | 2161 | TNF receptor (CrmB) | 642 | VACV-Acam2000-002 | 51058 | 38348860 | 2 |
| Vaccinia virus strain Acambis 2000 | Orthopoxvirus | 2161 | TNF receptor (CrmB) | 642 | VACV-Acam2000-003 | 51059 | 38348861 | 3 |
| Vaccinia virus strain Acambis 2000 | Orthopoxvirus | 2161 | TNF receptor (CrmC) | 712 | VACV-Acam2000-188 | 51244 | 38349046 | 190 |
| Vaccinia virus strain Acambis 2000 | Orthopoxvirus | 2161 | TNF receptor (CrmB) | 642 | VACV-Acam2000-233 | 51289 | 38349091 | 239 |
| Vaccinia virus strain Acambis 2000 | Orthopoxvirus | 2161 | TNF receptor (CrmB) | 642 | VACV-Acam2000-234 | 51290 | 38349092 | 240 |

TABLE 11-continued

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Vaccinia virus strain Acambis 3 | Orthopoxvirus | 2162 | TNF receptor (CrmB) | 642 | VACV-Acam3-002 | 51293 | 37551437 | 2 |
| Vaccinia virus strain Acambis 3 | Orthopoxvirus | 2162 | TNF receptor (CrmB) | 642 | VACV-Acam3-003 | 51294 | 37551438 | 3 |
| Vaccinia virus strain Acambis 3 | Orthopoxvirus | 2162 | TNF receptor (CrmC) | 712 | VACV-Acam3-190 | 51481 | 37551624 | 190 |
| Vaccinia virus strain Acambis 3 | Orthopoxvirus | 2162 | TNF receptor (CrmB) | 642 | VACV-Acam3-227 | 51518 | 37551661 | 239 |
| Vaccinia virus strain Acambis 3 | Orthopoxvirus | 2162 | TNF receptor (CrmB) | 642 | VACV-Acam3-228 | 51519 | 37551662 | 240 |
| Vaccinia virus strain Acambis 3000 Modified Virus Ankara | Orthopoxvirus | 1510 | TNF receptor (CrmB) | 642 | VACV-Acam3000-002 | 44316 | 47088328 | 2 |
| Vaccinia virus strain Acambis 3000 Modified Virus Ankara | Orthopoxvirus | 1510 | TNF receptor (CrmB) | 642 | VACV-Acam3000-194 | 44508 | 47088518 | 192 |
| Vaccinia virus strain Copenhagen | Orthopoxvirus | 1485 | TNF receptor (CrmB) | 642 | VACV-Cop-004 | 39529 | 335321 | C22L |
| Vaccinia virus strain Copenhagen | Orthopoxvirus | 1485 | TNF receptor (CrmC) | 712 | VACV-Cop-224 | 39749 | 335536 | A53R |
| Vaccinia virus strain Copenhagen | Orthopoxvirus | 1485 | TNF receptor (CrmC) | 712 | VACV-Cop-225 | 39750 | 335537 | A_ORF_T |
| Vaccinia virus strain Copenhagen | Orthopoxvirus | 1485 | TNF receptor (CrmB) | 642 | VACV-Cop-264 | 39789 | 335576 | B28R |
| Vaccinia virus strain DUKE | Orthopoxvirus | 2458 | TNF receptor (CrmB) | 642 | VACV-DUKE-002 | 63382 | 90819654 | 2 |
| Vaccinia virus strain DUKE | Orthopoxvirus | 2458 | TNF receptor (CrmB) | 642 | VACV-DUKE-003 | 63383 | 90819655 | 3 |
| Vaccinia virus strain DUKE | Orthopoxvirus | 2458 | TNF receptor (CrmC) | 712 | VACV-DUKE-188 | 63568 | 90819840 | 188 |
| Vaccinia virus strain DUKE | Orthopoxvirus | 2458 | TNF receptor (CrmB) | 642 | VACV-DUKE-223 | 63603 | 90819875 | 223 |
| Vaccinia virus strain DUKE | Orthopoxvirus | 2458 | TNF receptor (CrmB) | 642 | VACV-DUKE-224 | 63604 | 90819876 | 224 |
| Vaccinia virus strain LC16m8 | Orthopoxvirus | 1517 | TNF receptor (CrmB) | 642 | VACV-LC16m8-004 | 45457 | 56713345 | m8LTR09L |
| Vaccinia virus strain LC16m8 | Orthopoxvirus | 1517 | TNF receptor (CrmB) | 642 | VACV-LC16m8-005 | 45458 | 56713346 | m8LTR08L |
| Vaccinia virus strain LC16m8 | Orthopoxvirus | 1517 | TNF receptor (CrmC) | 712 | VACV-LC16m8-240 | 45693 | 56713579 | m8229R |
| Vaccinia virus strain LC16m8 | Orthopoxvirus | 1517 | TNF receptor (CrmC) | 712 | VACV-LC16m8-241 | 45694 | 56713580 | m8230R |
| Vaccinia virus strain LC16m8 | Orthopoxvirus | 1517 | TNF-alpha receptor (CPXV-GRI-K3R) | 742 | VACV-LC16m8-269 | 45722 | 56713608 | m8259R |
| Vaccinia virus strain LC16m8 | Orthopoxvirus | 1517 | TNF receptor (CrmB) | 642 | VACV-LC16m8-280 | 45733 | 56713619 | m8RTR08R |
| Vaccinia virus strain LC16m8 | Orthopoxvirus | 1517 | TNF receptor (CrmB) | 642 | VACV-LC16m8-281 | 45734 | 56713620 | m8RTR09R |
| Vaccinia virus strain LC16mO | Orthopoxvirus | 1518 | TNF receptor (CrmB) | 642 | VACV-LC16mO-004 | 45741 | 56713629 | mOLTR09L |
| Vaccinia virus strain LC16mO | Orthopoxvirus | 1518 | TNF receptor (CrmB) | 642 | VACV-LC16mO-005 | 45742 | 56713630 | mOLTR08L |
| Vaccinia virus strain LC16mO | Orthopoxvirus | 1518 | TNF receptor (CrmC) | 712 | VACV-LC16mO-240 | 45977 | 56713863 | mO229R |
| Vaccinia virus strain LC16mO | Orthopoxvirus | 1518 | TNF receptor (CrmC) | 712 | VACV-LC16mO-241 | 45978 | 56713864 | mO230R |
| Vaccinia virus strain LC16mO | Orthopoxvirus | 1518 | TNF-alpha receptor (CPXV-GRI-K3R) | 742 | VACV-LC16mO-269 | 46006 | 56713892 | mO259R |
| Vaccinia virus strain LC16mO | Orthopoxvirus | 1518 | TNF receptor (CrmB) | 642 | VACV-LC16mO-280 | 46017 | 56713903 | mORTR08R |
| Vaccinia virus strain LC16mO | Orthopoxvirus | 1518 | TNF receptor (CrmB) | 642 | VACV-LC16mO-281 | 46018 | 56713904 | mORTR09R |
| Vaccinia virus strain Lister | Orthopoxvirus | 1519 | TNF receptor (CrmB) | 642 | VACV-Lister-004 | 46025 | 0 | m8LTR09L |
| Vaccinia virus strain Lister | Orthopoxvirus | 1519 | TNF receptor (CrmB) | 642 | VACV-Lister-005 | 46026 | 0 | m8LTR08L |
| Vaccinia virus strain Lister | Orthopoxvirus | 1519 | TNF receptor (CrmC) | 712 | VACV-Lister-240 | 46261 | 0 | m8229R |

TABLE 11-continued

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Vaccinia virus strain Lister | Orthopoxvirus | 1519 | TNF receptor (CrmC) | 712 | VACV-Lister-241 | 46262 | 0 | m8230R |
| Vaccinia virus strain Lister | Orthopoxvirus | 1519 | TNF-alpha receptor (CPXV-GRI-K3R) | 742 | VACV-Lister-269 | 46290 | 0 | m8259R |
| Vaccinia virus strain Lister | Orthopoxvirus | 1519 | TNF receptor (CrmB) | 642 | VACV-Lister-280 | 46301 | 0 | m8RTR08R |
| Vaccinia virus strain Lister | Orthopoxvirus | 1519 | TNF receptor (CrmB) | 642 | VACV-Lister-281 | 46302 | 0 | m8RTR09R |
| Vaccinia virus strain Lister_VACV107 | Orthopoxvirus | 2659 | TNF receptor (CrmB) | 642 | VACV-Lister_VACV107-002 | 64335 | 0 | List002* |
| Vaccinia virus strain Lister_VACV107 | Orthopoxvirus | 2659 | TNF receptor (CrmC) | 712 | VACV-Lister_VACV107-176 | 64509 | 88854255 | List172 |
| Vaccinia virus strain Lister_VACV107 | Orthopoxvirus | 2659 | TNF-alpha receptor (CPXV-GRI-K3R) | 742 | VACV-Lister_VACV107-199 | 64532 | 88854282 | List195 |
| Vaccinia virus strain Lister_VACV107 | Orthopoxvirus | 2659 | TNF receptor (CrmB) | 642 | VACV-Lister_VACV107-204 | 64537 | 0 | List200* |
| Vaccinia virus strain MVA-I721 | Orthopoxvirus | 2696 | TNF receptor (CrmB) | 642 | VACV-MVA_I721-056 | 65270 | 0 | 192 |
| Vaccinia virus strain MVA-I721 | Orthopoxvirus | 2696 | TNF receptor (CrmB) | 642 | VACV-MVA_I721-114 | 65328 | 0 | 2 |
| Vaccinia virus strain Western Reserve | Orthopoxvirus | 1500 | TNF receptor (CrmB) | 642 | VACV-WR-002 | 42439 | 66275799 | 2 |
| Vaccinia virus strain Western Reserve | Orthopoxvirus | 1500 | TNF receptor (CrmB) | 642 | VACV-WR-004 | 42441 | 66275801 | 4 |
| Vaccinia virus strain Western Reserve | Orthopoxvirus | 1500 | TNF receptor (CrmC) | 712 | VACV-WR-179 | 42618 | 66275976 | 179 |
| Vaccinia virus strain Western Reserve | Orthopoxvirus | 1500 | TNF receptor (CrmB) | 642 | VACV-WR-215 | 42654 | 66276012 | 215 |
| Vaccinia virus strain Western Reserve | Orthopoxvirus | 1500 | TNF receptor (CrmB) | 642 | VACV-WR-217 | 42656 | 66276014 | 217 |
| Variola major virus strain Bangladesh 1975 | Orthopoxvirus | 1481 | TNF receptor (CrmB) | 642 | VARV-BGD75maj-191 | 38952 | 439102 | G2R |
| Variola minor virus strain Garcia 1966 | Orthopoxvirus | 1482 | TNF receptor (CrmB) | 642 | VARV-Gar_1966-207 | 39160 | 5830759 | G2R |
| Variola virus strain Afghanistan 1970 Variolator 4 | Orthopoxvirus | 2197 | TNF receptor (CrmB) | 642 | VARV-AFG70-202 | 53546 | 1.1E+08 | Crm-B secreted TNF-alpha-receptor-like protein |
| Variola virus strain Bangladesh 1974 (Shahzaman) | Orthopoxvirus | 2216 | TNF receptor (CrmB) | 642 | VARV-BGD74_shz-197 | 56989 | 94484853 | Crm-B secreted TNF-alpha-receptor-like protein |
| Variola virus strain Bangladesh 1974 (Solaiman) | Orthopoxvirus | 2217 | TNF receptor (CrmB) | 642 | VARV-BGD74_sol-197 | 57187 | 94485051 | Crm-B secreted TNF-alpha-receptor-like protein |
| Variola virus strain Bangladesh 1974 (nur islam) | Orthopoxvirus | 2215 | TNF receptor (CrmB) | 642 | VARV-BGD74_nur-197 | 56791 | 94484655 | Crm-B secreted TNF-alpha-receptor-like protein |
| Variola virus strain Bangladesh 1975 v75-550 Banu | Orthopoxvirus | 2198 | TNF receptor (CrmB) | 642 | VARV-BGD75_Banu-200 | 53747 | 1.1E+08 | Crm-B secreted TNF-alpha-receptor-like protein |

TABLE 11-continued

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain Benin, Dahomey 1968 (v68-59) | Orthopoxvirus | 2224 | TNF receptor (CrmB) | 642 | VARV-BEN68-207 | 58617 | 94483844 | Crm-B secreted TNF-alpha-receptor-like protein |
| Variola virus strain Botswana 1972 (v72-143) | Orthopoxvirus | 2225 | TNF receptor (CrmB) | 642 | VARV-BWA72-201 | 58820 | 94484048 | Crm-B secreted TNF-alpha-receptor-like protein |
| Variola virus strain Botswana 1973 (v73-225) | Orthopoxvirus | 2226 | TNF receptor (CrmB) | 642 | VARV-BWA73-201 | 59022 | 94484250 | Crm-B secreted TNF-alpha-receptor-like protein |
| Variola virus strain Brazil 1966 (v66-39 Sao Paulo) | Orthopoxvirus | 2227 | TNF receptor (CrmB) | 642 | VARV-BRA66-209 | 59232 | 94484457 | Crm-B secreted TNF-alpha-receptor-like protein |
| Variola virus strain China Horn 1948 Sabin Lab July 1948 | Orthopoxvirus | 2203 | TNF receptor (CrmB) | 642 | VARV-CHN48-203 | 54363 | 1.1E+08 | Crm-B secreted TNF-alpha-receptor-like protein |
| Variola virus strain Congo 1970 v70-46 Kinshasa | Orthopoxvirus | 2229 | TNF receptor (CrmB) | 642 | VARV-COG70_46-201 | 59636 | 1.1E+08 | Crm-B secreted TNF-alpha-receptor-like protein |
| Variola virus strain Congo 9 1970 (v74-227 Gispen) | Orthopoxvirus | 2228 | TNF receptor (CrmB) | 642 | VARV-COG70_227-200 | 59434 | 94485252 | Crm-B secreted TNF-alpha-receptor-like protein |
| Variola virus strain Ethiopia 1972 (Eth16 R14-1X-72 Addis) | Orthopoxvirus | 2231 | TNF receptor (CrmB) | 642 | VARV-ETH72_16-202 | 60075 | 94485455 | Crm-B secreted TNF-alpha-receptor-like protein |
| Variola virus strain Ethiopia 1972 (Eth17 R14-1X-72 Addis) | Orthopoxvirus | 2232 | TNF receptor (CrmB) | 642 | VARV-ETH72_17-200 | 60276 | 94485657 | Crm-B secreted TNF-alpha-receptor-like protein |
| Variola virus strain Germany 1958 Heidelberg | Orthopoxvirus | 2233 | TNF receptor (CrmB) | 642 | VARV-DEU58-200 | 60477 | 1.1E+08 | Crm-B secreted TNF-alpha-receptor-like protein |
| Variola virus strain Guinea 1969 (005) | Orthopoxvirus | 2234 | TNF receptor (CrmB) | 642 | VARV-GIN69-205 | 60683 | 94485860 | Crm-B secreted TNF-alpha-receptor-like protein |
| Variola virus strain India 1953 (Kali-Muthu-M50 Madras) | Orthopoxvirus | 2238 | TNF receptor (CrmB) | 642 | VARV-IND53_mad-200 | 61490 | 94486063 | Crm-B secreted TNF-alpha-receptor-like protein |
| Variola virus strain India 1953 (New Delhi) | Orthopoxvirus | 2239 | TNF receptor (CrmB) | 642 | VARV-IND53_ndel-200 | 61691 | 94486265 | Crm-B secreted TNF-alpha-receptor-like protein |
| Variola virus strain India 1964 7124 Vellore | Orthopoxvirus | 2240 | TNF receptor (CrmB) | 642 | VARV-IND64_vel4-204 | 61897 | 1.1E+08 | Crm-B secreted TNF-alpha-receptor-like protein |

TABLE 11-continued

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain India 1964 7125 Vellore | Orthopoxvirus | 2241 | TNF receptor (CrmB) | 642 | VARV-IND64_vel5-202 | 62100 | 1.1E+08 | Crm-B secreted TNF-alpha-receptor-like protein |
| Variola virus strain India 3 Major 1967 | Orthopoxvirus | 1483 | TNF receptor (CrmB) | 642 | VARV-IND3_1967-199 | 39361 | 9627717 | G4R |
| Variola virus strain Iran 1972 2602 Tabriz | Orthopoxvirus | 2235 | TNF receptor (CrmB) | 642 | VARV-IRN72-202 | 60887 | 1.1E+08 | Crm-B secreted TNF-alpha-receptor-like protein |
| Variola virus strain Japan 1946 (Yamada MS-2(A) Tokyo) | Orthopoxvirus | 2243 | TNF receptor (CrmB) | 642 | VARV-JPN46_yam-200 | 62475 | 94486468 | Crm-B secreted TNF-alpha-receptor-like protein |
| Variola virus strain Japan 1951 (Harper, Masterseed) | Orthopoxvirus | 2244 | TNF receptor (CrmB) | 642 | VARV-JPN51_hrpr-199 | 62676 | 94486670 | Crm-B secreted TNF-alpha-receptor-like protein |
| Variola virus strain Japan 1951 (Stillwell, Masterseed) | Orthopoxvirus | 2245 | TNF receptor (CrmB) | 642 | VARV-JPN51_stwl-200 | 62878 | 94486872 | Crm-B secreted TNF-alpha-receptor-like protein |
| Variola virus strain Korea 1947 (Lee, Masterseed) | Orthopoxvirus | 2236 | TNF receptor (CrmB) | 642 | VARV-KOR47-201 | 61089 | 94487076 | Crm-B secreted TNF-alpha-receptor-like protein |
| Variola virus strain Kuwait 1967 (K1629) | Orthopoxvirus | 2237 | TNF receptor (CrmB) | 642 | VARV-KWT67-199 | 61289 | 94487276 | Crm-B secreted TNF-alpha-receptor-like protein |
| Variola virus strain Nepal 1973 V73-175 | Orthopoxvirus | 2221 | TNF receptor (CrmB) | 642 | VARV-NPL73-201 | 57991 | 1.1E+08 | Crm-B secreted TNF-alpha-receptor-like protein |
| Variola virus strain Niger 1969 (001, importation from Nigeria) | Orthopoxvirus | 2222 | TNF receptor (CrmB) | 642 | VARV-NER69-207 | 58200 | 94487481 | Crm-B secreted TNF-alpha-receptor-like protein |
| Variola virus strain Sierra Leone 1969 (V68-258) | Orthopoxvirus | 2223 | TNF receptor (CrmB) | 642 | VARV-SLE68-206 | 58408 | 94488089 | Crm-B secreted TNF-alpha-receptor-like protein |
| Variola virus strain Somalia 1977 (V77-1252) | Orthopoxvirus | 2218 | TNF receptor (CrmB) | 642 | VARV-SOM77_1252-199 | 57387 | 94488290 | Crm-B secreted TNF-alpha-receptor-like protein |
| Variola virus strain Somalia 1977 (V77-1605) | Orthopoxvirus | 2219 | TNF receptor (CrmB) | 642 | VARV-SOM77_1605-199 | 57587 | 94488490 | Crm-B secreted TNF-alpha-receptor-like protein |
| Variola virus strain Somalia 1977 V77-2479 | Orthopoxvirus | 2220 | TNF receptor (CrmB) | 642 | VARV-SOM77_ali-201 | 57789 | 1.1E+08 | Crm-B secreted TNF-alpha-receptor-like protein |

TABLE 11-continued

Viral Orthologous Clusters V2.0
(VOCs)
TNF receptor
Gene Results Table

| Genome name | Genus | Genome id | Ortholog Group Name | Ortholog Group ID | Gene number | Gene id | Genbank id | Genbank name |
|---|---|---|---|---|---|---|---|---|
| Variola virus strain South Africa 1965 (102 Natal, Ingwavuma) | Orthopoxvirus | 2210 | TNF receptor (CrmB) | 642 | VARV-ZAF65_102-200 | 55772 | 94487683 | Crm-B secreted TNF-alpha-receptor-like protein |
| Variola virus strain South Africa 1965 (103 Tvaal, Nelspruit) | Orthopoxvirus | 2211 | TNF receptor (CrmB) | 642 | VARV-ZAF65_103-200 | 55973 | 94487885 | Crm-B secreted TNF-alpha-receptor-like protein |
| Variola virus strain Sudan 1947 (Juba) | Orthopoxvirus | 2212 | TNF receptor (CrmB) | 642 | VARV-SDN47_jub-199 | 56173 | 94488691 | Crm-B secreted TNF-alpha-receptor-like protein |
| Variola virus strain Sudan 1947 (Rumbec) | Orthopoxvirus | 2213 | TNF receptor (CrmB) | 642 | VARV-SDN47_rum-200 | 56374 | 94488892 | Crm-B secreted TNF-alpha-receptor-like protein |
| Variola virus strain Sumatra 1970 V70-222 | Orthopoxvirus | 2208 | TNF receptor (CrmB) | 642 | VARV-SUM70_222-200 | 55370 | 1.1E+08 | Crm-B secreted TNF-alpha-receptor-like protein |
| Variola virus strain Sumatra 1970 V70-228 | Orthopoxvirus | 2209 | TNF receptor (CrmB) | 642 | VARV-SUM70_228-198 | 55570 | 94489091 | Crm-B secreted TNF-alpha-receptor-like protein |
| Variola virus strain Syria 1972 V72-199 | Orthopoxvirus | 2206 | TNF receptor (CrmB) | 642 | VARV-SYR72-202 | 54968 | 1.1E+08 | Crm-B secreted TNF-alpha-receptor-like protein |
| Variola virus strain Tanzania 1965 kembula | Orthopoxvirus | 2207 | TNF receptor (CrmB) | 642 | VARV-TZA65-200 | 55169 | 94489291 | Crm-B secreted TNF-alpha-receptor-like protein |
| Variola virus strain United Kingdom 1946 Harvey | Orthopoxvirus | 2204 | TNF receptor (CrmB) | 642 | VARV-GBR44_harv-201 | 54566 | 94489494 | Crm-B secreted TNF-alpha-receptor-like protein |
| Variola virus strain United Kingdom 1946 Hinden (Middlesex) | Orthopoxvirus | 2205 | TNF receptor (CrmB) | 642 | VARV-GBR46_hind-198 | 54765 | 94489693 | Crm-B secreted TNF-alpha-receptor-like protein |
| Variola virus strain United Kingdom 1947 Higgins (Staffordshire) | Orthopoxvirus | 2202 | TNF receptor (CrmB) | 642 | VARV-GBR47_hig-200 | 54159 | 94489894 | Crm-B secreted TNF-alpha-receptor-like protein |
| Variola virus strain United Kingdom 1952 Butler | Orthopoxvirus | 2200 | TNF receptor (CrmB) | 642 | VARV-GBR52_but-209 | 53957 | 94490101 | Crm-B secreted TNF-alpha-receptor-like protein |
| Variola virus strain Yugoslavia 1972 V72-164 | Orthopoxvirus | 2196 | TNF receptor (CrmB) | 642 | VARV-YUG72-200 | 53343 | 94490304 | Crm-B secreted TNF-alpha-receptor-like protein |
| Yaba monkey tumor virus strain Amano | Yatapoxvirus | 1503 | Secreted TNF binding protein | 725 | YMTV-Amano-002 | 43051 | 38229171 | 2L |
| Yaba-like Disease Virus strain Davis | Yatapoxvirus | 1487 | Secreted TNF binding protein | 725 | YLDV-Davis-002 | 40051 | 12084985 | 2L |

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A pharmaceutical composition comprising a humanized isolated antibody or functional fragment thereof immunologically specific for a viral interferon α/β binding protein, contained in a pharmaceutically acceptable carrier suitable for passive immunization into a human subject, said antibody cross reacting with and blocking the activity of an interferon α/β binding protein from a pox virus selected from the group consisting of monkey pox virus (MPXV), variola virus (VARV) and ectromelia virus (ECTV).

2. A method for passively immunizing a subject against pox infection comprising administering an effective amount of the composition of claim 1 to a subject in need thereof, said administration being effective to treat or attenuate said pox infection.

3. The method of claim 2, wherein said pox infection is selected from the group consisting of small pox infection and monkey pox infection, said method optionally comprising administration of an anti-viral agent.

* * * * *